(12) United States Patent
Awaji et al.

(10) Patent No.: US 8,357,522 B2
(45) Date of Patent: Jan. 22, 2013

(54) SEPARATING MATERIAL AND METHOD FOR COLLECTING CELL OR THE LIKE USING THE SAME

(75) Inventors: Hiroshi Awaji, Settsu (JP); Ashutosh Kumar, Settsu (JP); Akira Kobayashi, Takasago (JP); Naohiro Imai, Takasago (JP)

(73) Assignee: Kaneka Corporation, Osaka (JP)

( * ) Notice: Subject to any disclaimer, the term of this patent is extended or adjusted under 35 U.S.C. 154(b) by 897 days.

(21) Appl. No.: 12/302,881

(22) PCT Filed: May 25, 2007

(86) PCT No.: PCT/JP2007/060721
§ 371 (c)(1),
(2), (4) Date: Jun. 9, 2009

(87) PCT Pub. No.: WO2007/139028
PCT Pub. Date: Dec. 6, 2007

(65) Prior Publication Data
US 2009/0239300 A1    Sep. 24, 2009

(30) Foreign Application Priority Data

| May 29, 2006 | (JP) | 2006-148620 |
| May 29, 2006 | (JP) | 2006-149031 |
| Jun. 13, 2006 | (JP) | 2006-163955 |
| Jun. 29, 2006 | (JP) | 2006-179690 |

(51) Int. Cl.
*C12N 5/06* (2006.01)
*C07K 1/00* (2006.01)

(52) U.S. Cl. ..... 435/178; 435/377; 435/378; 435/308.1; 530/412; 530/396; 536/123.13; 536/123.1

(58) Field of Classification Search ............... 435/178, 435/377, 378, 308.1; 530/412, 396; 536/123.13, 536/123.1
See application file for complete search history.

(56) References Cited

U.S. PATENT DOCUMENTS

| 6,926,915 B1 | 8/2005 | Yura et al. |
| 2005/0214758 A1 | 9/2005 | Yura et al. |
| 2006/0194318 A1 | 8/2006 | Shankar et al. |
| 2008/0248011 A1 | 10/2008 | Nakagawa et al. |

FOREIGN PATENT DOCUMENTS

| JP | 08-119994 A | 5/1996 |
| JP | 11-315091 A | 11/1999 |
| WO | 00/58443 A1 | 10/2000 |
| WO | 02/055021 A3 | 7/2002 |
| WO | 03/004616 A2 | 1/2003 |
| WO | WO 03/004616 A2 * | 1/2003 |
| WO | 03/033522 A1 | 4/2003 |
| WO | WO 03/033522 A1 * | 4/2003 |
| WO | 03/050532 A1 | 6/2003 |
| WO | 2004/072262 A2 | 8/2004 |
| WO | 2005/070964 A1 | 8/2005 |

* cited by examiner

*Primary Examiner* — Robert D. Harlan
(74) *Attorney, Agent, or Firm* — Sughrue Mion, PLLC

(57) ABSTRACT

The present invention provides a novel material useful for selectively isolating a cell such as monocyte and the like or a protein from a body fluid and a production method thereof, a physiological material using the material and an isolation material using the physiological material, as well as a method of harvesting a cell such as monocyte and the like using the isolation material, a method of harvesting a protein and a method of preparing a dendritic cell.

8 Claims, No Drawings

SEPARATING MATERIAL AND METHOD FOR COLLECTING CELL OR THE LIKE USING THE SAME

TECHNICAL FIELD

The present invention relates to a novel material useful for selectively isolating a cell such as monocyte and the like from a body fluid or a protein contained in an animal or plant and a production method thereof, a physiological material using the material and an isolation material using the same, as well as a method of harvesting a cell such as monocyte and the like, a method of harvesting a protein by the use of the isolation material, and a method of preparing a dendritic cell.

BACKGROUND ART

In recent years, it has been clarified that sugar chain present in the cell surface is deeply involved in various vital phenomena (cell recognition, transduction of information, cell adhesion, differentiation and proliferation, canceration, virus infection, blood coagulation, immune reaction and the like). When the target molecule in the phenomenon is a sugar chain, the interaction is classified into a "sugar chain-sugar chain" interaction, and when the target molecule is a protein, it is classified into a "sugar chain-protein" interaction. In the former, cell surface sugar chains in a particular sugar chain structure combinatory relationship are bound to each other. In the latter, one of the cell surface sugar chains recognizes and binds to a sugar chain recognition protein on the other cell surface, where lectin, glycosyltransferase and glycohydrolase are said to be involved as the sugar chain recognition protein. Inspired by such vital phenomenon, the development and research of a physiological material (cell or protein isolation material, device, sensor), pharmaceutical products and the like, incorporating a sugar chain, has been actively performed (e.g., non-patent documents 1, 2 and 3).

For the development of a sugar chain-containing functional material that expresses a desired physiological function, the correlation between the structure and physiological activity of a sugar chain needs to be studied at molecular and functional group levels, as well as a technique to freely modify a sugar chain molecule and introduce same into a polymer is required.

With these backgrounds, various sugar chain-containing polymers have been reported. For example, as polymers incorporating a sugar chain such as monosaccharide, disaccharide, oligosaccharide and the like (hereinafter sugar chain polymer),
1. polyvinyl alcohol type (e.g., patent document 1)
2. polyacrylate type (e.g., patent document 2)
3. polystyrene type (e.g., patent documents 3-8)
4. polyether type (e.g., patent document 9)
5. polyethyleneimine type (e.g., patent documents 10 and 11)
6. polyamino acid type (e.g., patent documents 12-16)
7. polyurethane type (e.g., patent document 17)
and the like are known. Among these, patent document 5 discloses selective adhesion and collection of hepatocytes as well as cancer cell recognition using a sugar chain polymer-coated substrate.

In recent years, a cell treatment has been practiced wherein cells contained in body fluids such as blood, bone marrow and the like are isolated and transplanted for the purpose of regeneration of tissues such as blood vessel and the like as well as immunomodulation of cancer patients. Along therewith, various materials, devices and the like for selectively isolating cells useful for the treatment have been developed. Among the cells present in body fluids represented by blood, monocyte has blood vessel regeneration capability (non-patent documents 4, 5), and is drawing attention as a precursor cell of a dendritic cell to be used for a dendritic cell therapy, which is one of the cell immunity therapies (non-patent document 6). As a method for isolating monocytes from a body fluid such as blood and the like, the following have been reported.

Examples of a method of isolating peripheral blood monocytes include a density-gradient centrifugation method wherein the difference in the specific gravity of the cells is utilized for isolation, a method wherein a blood component containing monocytes is isolated from the peripheral blood by apheresis and the like, highly adhesive monocytes are attached to a physical and chemical instrument such as a polystyrene flask and the like, and non-adhesive cells are removed to isolate the monocytes, a method wherein monocytes are selectively isolated by utilizing magnetic beads bound with an antibody to the monocyte and the like. The isolated monocytes are cultured with cytokine such as IL-4, GM-CSF and the like to induce differentiation into dendritic cells, which are used as cancer treatment cells.

However, the method of isolating monocytes by the density-gradient centrifugation method is associated with many problems yet to be solved, such as a safety problem of the liquid to be used for density gradient (cytotoxicity and the like), an operability problem because of a long time required for centrifugation, washing operation and the like, much loss of cells, an open system operation allowing easy contamination and the like, isolation efficiency (insufficient removal of non-adhesive cells, contamination with lymphocytes) and the like.

Moreover, a method including isolation of mononuclear cells by the density-gradient centrifugation method, and selective attachment of monocytes to a physical and chemical instrument such as plastic dish and the like by utilizing the difference in the adhesion of monocytes and lymphocytes to a substrate is known. However, this method requires complicated operation, and the recovery rate and purity of the isolated monocytes are not sufficient.

The isolation method using magnetic beads with antibody can isolate monocytes at a comparatively high purity, but the cell treatment requires a long time, and also, is expensive.

In the elutriation method, a cell suspension is centrifuged in a chamber having a slope, while flowing a buffer in an opposite direction from the centrifugation to form a particular cell layer. This method affords high purity monocytes, but the apparatus is expensive, and requires a skillful operation technique. In addition, the cell isolation problematically requires a long time.

In recent years, moreover, a monocyte isolation method using a cell isolation filter has been reported.

For example, patent document 18 discloses a method of collecting nuclear cells by trapping nuclear cells on a filter that traps nuclear cells but passes red blood cells, and inducing a liquid current in the opposite direction from the first liquid flow direction. However, this document is directed to a filter for collecting nuclear cells, where selectivity to monocyte is absent.

In addition, patent document 19 discloses monocyte and/or monocyte-derived macrophage selective removal filter apparatus. However, this document is directed to a physical filtration filter wherein the average pore cross sectional area and bulk density of the filter were defined in consideration of the particle size of macrophage, which is clearly different from the present invention wherein monocytes are selectively isolated utilizing the affinity for the monocytes.

Patent document 20 also discloses that the monocyte trap rate increases by defining the packing density and fiber diameter of the filter. For the same reasons as mentioned above, it is clearly different from the present invention. In addition, the property is not sufficient because the monocyte recovery rate is about 50% and the purity is about 40%.

Lectin widely present in the biological world including animals, plants, microorganisms etc. is a generic term of proteins that recognize a sugar chain. Lectin specifically binds to a sugar chain having a particular structure, which is present in blood cell, cell surface and the like, and has an activity to aggregate blood cells and cells. For example, sword bean-derived concanavalin A (ConA) and wheat germ agglutinin (WGA) are known to aggregate malignant cells. As mentioned above, lectin is medically highly useful as a cell fractionation reagent, clinical diagnostic reagent, clinical therapeutic drug and the like, based on its sugar chain binding specificity, blood type specificity, anticancer effect and the like. At present, a wide variety of lectins are isolated from various individuals, and their functions are being strenuously examined. To further clarify the property of undeveloped lectin and develop practical use, a technique for efficient isolation and purification of useful lectin at a low cost is required (non-patent documents 7, 8).

As a conventional protein isolation method, a fractionation method utilizing difference in solubilities (salting out, fractional precipitation by organic solvent, acidic precipitation and isoelectric point precipitation), and fractionation by column chromatography (ion exchange chromatography, hydrophobic chromatography, gel filtration chromatography, affinity chromatography) are known. For isolation and purification of lectin, one kind of protein, from a naturally occurring substance such as pulse and the like, isolation from contaminating protein, fat, sugar, amino acid etc. is required, and as a method therefor, a combination of the above-mentioned methods (ion exchange and gel filtration chromatography after salting out) has been employed. However, such method cannot isolate lectin sufficiently, and high purity lectin cannot be obtained problematically. Therefore, for example, affinity chromatography using a carrier having a sugar such as maltose, lactose and the like immobilized thereon as a ligand (patent documents 21-24), and affinity chromatography using a methacrylate polymer bound with a sugar such as maltose, lactose (patent document 25), albumen-derived sugar chain (patent document 26) and the like have been utilized. As shown, various materials and methods for isolating lectin have been disclosed.

Nevertheless, since this method requires chemically binding a sugar ligand onto the carrier surface, the sugar density is not sufficient, lectin is not sufficiently isolated, and high purity lectin cannot be obtained problematically.

Sulfated sugar is known to have affinity for influenza virus and AIDS virus, and development of a new material capable of trapping viruses utilizing the principle and its production method is desired. With such backgrounds, various sulfated sugar chain-containing polymers have been reported. For example, a sulfated galactose-inducing polyacrylate type (e.g., patent document 27), sulfated sugar-inducing polyethylene type (e.g., patent document 28), sulfated glucosamine-inducing polyethylene type (e.g., patent document 29) and the like are known.

The biological functions such as recognition, adhesion and the like of cell, protein containing lectin or virus are expressed due to a "sugar chain-sugar chain interaction" or a "sugar chain-protein interaction" between a sugar chain aggregate (cluster) on the cell surface and a sugar chain aggregate complementary thereto, and the strength of the interaction is known to correlate with the sugar chain density. Since only one sugar chain such as monosaccharide, disaccharide, oligosaccharide and the like can be linearly introduced per repeat unit into the sugar chain polymers disclosed in the above-mentioned patent documents 1-17 and 25-29, the number of repeat units having a sugar chain introduced thereinto in a polymer chain needs to be increased so as to sufficiently express the biological function (recognition, adhesion and the like to cell, protein, containing lectin and virus) of sugar chain by increasing the sugar chain density in the sugar chain cluster. On the other hand, this may result in the degradation of the film forming capability, mechanical intensity and the like that skeleton polymers inherently show.

From the aspects of biocompatibility and blood compatibility, the polyurethane type sugar chain polymer disclosed in patent document 17 is preferable. However, since the production step for introducing a sugar chain into the side chain requires complicated protection and deprotection operations, the production cost may problematically increase.

patent document 1: JP-A-63-238105
patent document 2: JP-A-63-68603
patent document 3: JP-A-7-304788
patent document 4: JP-A-8-253495
patent document 5: JP-A-8-319317 (JP-B-3053764)
patent document 6: JP-A-8-253495
patent document 7: JP-A-2002-88094
patent document 8: JP-A-2005-112987
patent document 9: JP-A-5-140294
patent document 10: JP-A-5-140213
patent document 11: JP-A-2002-302511
patent document 12: JP-A-5-178986
patent document 13: JP-A-8-337566
patent document 14: JP-A-9-227600
patent document 15: JP-A-11-60603
patent document 16: JP-A-2003-73397
patent document 17: JP-A-11-71391
patent document 18: WO98/32840
patent document 19: JP-A-9-75076 (JP-B-3812909)
patent document 20: JP-A-2004-129550
patent document 21: JP-A-62-201641
patent document 22: JP-B-2660175
patent document 23: JP-A-10-504287
patent document 24: JP-B-3711356
patent document 25: JP-A-63-68603
patent document 26: JP-B-1995189
patent document 27: JP-A-11-315091
patent document 28: JP-A-2004-526691
patent document 29: JP-A-2005-15451
non-patent document 1: Design and Physiology of Sugar Chain Molecule, 2001, Japan Scientific Societies Press
non-patent document 2: Method of Studying Physiologically Active Sugar Chain, 1999, Japan Scientific Societies Press
non-patent document 3: Carbohydrate Engineering and Production Technique, 1993, Science Forum Inc.
non-patent document 4: Proc. Natl. Acad. Sci., vol. 100, No. 5: 2, 426-2431, 2003
non-patent document 5: Cardiovasc. Research, 49(3): 671-680, 2001
non-patent document 6: Cancer Res., vol. 59: 56-58. 1999
non-patent document 7: New Biochemical Experiment Course 1 Protein isolation, purification, properties, 1993, Ed. The Japanese Biochemical Society, Tokyo Kagaku Dozin Co., Ltd.
non-patent document 8: Lectin, N. Sharon•H. L is ed., translated by Toshiaki Ohsawa•Yukiko Konami, 1989, Japan Scientific Societies Press

DISCLOSURE OF THE INVENTION

Problems to be Solved by the Invention

An object of the present invention is to provide a novel material having superior film forming capability, which is expected to show various physiological functions such as biocompatibility, blood compatibility, affinity for cell or protein, and the like, and a convenient and low cost production method thereof, provide a physiological material containing the material and an isolation material using the same, and to provide a convenient and efficient method of harvesting a cell such as monocyte and the like or a protein as well as a convenient and efficient method of preparing a dendritic cell, using the isolation material.

Means of Solving the Problems

The present inventors have conducted intensive studies in an attempt to solve the above-mentioned problems and found that a cell such as monocyte and the like or a protein can be isolated conveniently and efficiently by the use of an isolation material containing, on at least a part of the surface, a substance having a sugar structure, and that a dendritic cell can be prepared conveniently and efficiently from a monocyte.

Furthermore, the present inventors have also found that, as the above-mentioned substance having a sugar structure, a sugar chain-containing polymer having a particular structure defined below particularly has superior film forming capability, is expected to have various physiological functions such as biocompatibility, blood compatibility, affinity for a cell or a protein and the like, and is useful for harvesting a cell such as monocyte and the like or a protein, and that the sugar chain-containing polymer can be produced by a convenient method at a low cost.

Accordingly, the present invention provides the following.

[1] A method of harvesting a monocyte, comprising performing
  1) a step for trapping a monocyte in an isolation material by contacting a body fluid with the isolation material comprising, on at least a part of a surface thereof, a substance having a sugar structure,
  2) a step for removing untrapped monocytes by washing the isolation material with a washing liquid, and
  3) a step for collecting a trapped monocyte from the isolation material, in this order.

[2] The method of the above-mentioned [1], wherein the monocyte is collected using a solution for cell collection, comprising one or more kinds of sugars selected from the group consisting of mannose, glucose, galactose and fucose, in the aforementioned step 3).

[3] A method of preparing a dendritic cell, comprising inducing further differentiation of a monocyte collected by the method of the above-mentioned [1] or [2] into a dendritic cell.

[4] A method of preparing a dendritic cell, comprising performing
  1) a step for trapping a monocyte in an isolation material by contacting a body fluid with the isolation material comprising, on at least a part of a surface thereof, a substance having a sugar structure,
  2) a step for removing untrapped monocytes by washing the isolation material with a washing liquid,
  3) a step for inducing further differentiation of a monocyte trapped by the isolation material to give a dendritic cell, and
  4) a step for collecting the dendritic cell after differentiation induction from the isolation material, in this order.

[5] A composition comprising a dendritic cell obtained by the method of the above-mentioned [3] or [4].

[6] A method of harvesting a protein, comprising performing
  1) a step for trapping a protein in an isolation material by contacting a protein-containing liquid with the isolation material comprising, on at least a part of a surface thereof, a substance having a sugar structure,
  2) a step for removing untrapped proteins by washing the isolation material with a washing liquid, and
  3) a step for collecting a trapped protein from the isolation material, in this order.

[7] The method of the above-mentioned [6], wherein the protein is lectin.

[8] The method of the above-mentioned [7], wherein the lectin is concanavalin A (ConA) or wheat germ agglutinin (WGA).

[9] A lectin-containing composition obtained by the method of the above-mentioned [6].

[10] The method of any one of the above-mentioned [1]-[4] and [6]-[8], wherein the substance having a sugar structure is a sugar chain-containing polymer having, as a partial structure, (i) a monosaccharide derivative, an oligosaccharide derivative and/or a polysaccharide derivative, each having a reactive functional group, or (ii) a monosaccharide derivative, an oligosaccharide derivative and/or a polysaccharide derivative.

[11] The method of the above-mentioned [10], wherein the sugar constituting the substance having a sugar structure is at least one sugar selected from the group consisting of mannose, glucose, galactose, lactose, fucose, trehalose, maltose and cyclo{→6)-α-D-glucopyranosyl-(1→3)-α-D-glucopyranosyl-(1→6)-α-D-glucopyranosyl-(1→3)-α-D-glucopyranosyl-(1→}.

[12] The method of the above-mentioned [10], wherein the substance having a sugar structure is a sugar chain-containing polymer having, as a partial structure, a monosaccharide derivative, an oligosaccharide derivative and/or a polysaccharide derivative.

[13] The method of the above-mentioned [12], wherein the sugar chain-containing polymer is a sugar residue-modified oligosaccharide-containing polyurethane represented by the following formula [1-1]:

$$\begin{aligned}&-\{[CO-NH-R^1-NH-CO]-[O-R^2-O]\}_m-\#\\&\qquad\qquad\qquad\qquad\qquad(O_2C-R^3-CO-NH-R^4)_p\\&\qquad\qquad\qquad\qquad\qquad|\\&\#-\{[CO-NH-R^1-NH-CO]-[O-OLS-O]\}_n-\\&\qquad\qquad\qquad\qquad\quad\diagup\qquad\diagdown\\&\qquad\qquad\qquad(HO_2C-R^3-CO_2)_q\quad(OH)_{r-p-q}\end{aligned}\qquad[1\text{-}1]$$

wherein $R^1$ is a divalent $C_{1-16}$ hydrocarbon group optionally having substituent(s), $R^2$ is a divalent group containing the same or different 1 to 100 units in total selected from a $C_{2-12}$ oxyalkylene unit and a divalent $C_{2-12}$ hydrocarbon unit optionally having substituent(s), $R^3$ is a $C_{2-4}$ alkylene group, $R^4$ is a monosaccharide- or disaccharide-derived sugar residue, OLS is an oligosaccharide skeleton having two primary hydroxyl groups, r shows the total number of secondary hydroxyl groups of oligosaccharide, p and q are each an integer within the range of $1 \leq p \leq r$, $0 \leq q \leq r-1$, and m and n are each a repeat unit number, m is an integer of 0-1000 and n is an integer of 1-1000, and n/(m+n) is a number within the range of 0.01-1.00.

[14] The method of the above-mentioned [12], wherein the sugar chain-containing polymer is a carboxyl group-modified oligosaccharide-containing polyurethane represented by the following formula [1-2]:

$$—\{[CO—NH—R^1—NH—CO]—[O—R^2—O]\}_m—\#$$
$$\#—\{[CO—NH—R^1—NH—CO]-[O\text{-}OLS\text{-}O]\}_n—$$
$$(HO_2C—R^3-CO_2)_{p+q} \quad (OH)_{r\text{-}p\text{-}q}$$

[1-2]

wherein
$R^1$ is a divalent $C_{1-16}$ hydrocarbon group optionally having substituent(s),
$R^2$ is a divalent group containing the same or different 1 to 100 units in total selected from a $C_{2-12}$ oxyalkylene unit and a divalent $C_{2-12}$ hydrocarbon unit optionally having substituent(s),
$R^3$ is a $C_{2-4}$ alkylene group,
OLS is an oligosaccharide skeleton having two primary hydroxyl groups,
r shows the total number of secondary hydroxyl groups of oligosaccharide,
p and q are each an integer within the range of $1 \leq p \leq r$, $0 \leq q \leq r-1$, and
m and n are each a repeat unit number, m is an integer of 0-1000 and n is an integer of 1-1000, and n/(m+n) is a number within the range of 0.01-1.00.

[15] The method of the above-mentioned [12], wherein the sugar chain-containing polymer is an acid-modified oligosaccharide-containing polyurethane represented by the following formula [2-1]:

$$—\{[CO—NH—R^1—NH—CO]—[O—R^2—O]\}_m—\#$$
$$(OXM)_s$$
$$\#—\{[CO—NH—R^1—NH—CO]—[O\text{-}OLS\text{-}O]\}_n—$$
$$(OH)_{r\text{-}s}$$

[2-1]

wherein
$R^1$ is a divalent $C_{1-16}$ hydrocarbon group optionally having substituent(s),
$R^2$ is a divalent group containing the same or different 1 to 100 units in total selected from a $C_{2-12}$ oxyalkylene unit and a divalent $C_{2-12}$ hydrocarbon unit optionally having substituent(s),
OLS is an oligosaccharide skeleton having two primary hydroxyl groups,
r shows the total number of secondary hydroxyl groups of oligosaccharide,
XM is an acid-containing group wherein M is a hydrogen atom, an alkali metal atom, an ammonium group or an organic amino group, and X is an acid-derived moiety,
shows the number of the secondary hydroxyl groups of an oligosaccharide modified with an acid-containing group, which is an integer within the range of $1 \leq s \leq r$, and
m and n are each a repeat unit number, m is an integer of 0-1000 and n is an integer of 1-1000, and n/(m+n) is a number within the range of 0.01-1.00.

[16] The method of the above-mentioned [12], wherein the sugar chain-containing polymer is an acid-modified sugar residue-modified oligosaccharide represented by the following formula [3-1]:

$$—\{[CO—NH—R^1—NH—CO]—[O—R^2—O]\}_m—\#$$
$$(O_2C\text{-}R^3\text{-}CO—NH—R^4\text{-}(XM))_p$$
$$\#—\{[CO—NH—R^1—NH—CO]-[O\text{-}OLS\text{-}O]\}_n—$$
$$(HO_2C—R^3\text{-}CO_2)_q \quad (OH)_{r\text{-}p\text{-}q}$$

[3-1]

wherein
$R^1$ is a divalent $C_{1-16}$ hydrocarbon group optionally having substituent(s),
$R^2$ is a divalent group containing the same or different 1 to 100 units in total selected from a $C_{2-12}$ oxyalkylene unit and a divalent $C_{2-12}$ hydrocarbon unit optionally having substituent(s),
$R^3$ is a $C_{2-4}$ alkylene group,
$R^4$ is a monosaccharide- or disaccharide-derived sugar residue,
XM is an acid-containing group wherein M is a hydrogen atom, an alkali metal atom, an ammonium group or an organic amino group, and X is an acid-derived moiety,
s shows the number of hydroxyl groups of a sugar residue $R^4$ modified with an acid-containing group, which is an integer within the range of $1 \leq s \leq 4$,
OLS is an oligosaccharide skeleton having two primary hydroxyl groups,
r shows the total number of secondary hydroxyl groups of oligosaccharide,
p and q are each an integer within the range of $1 \leq p \leq r$, $0 \leq q \leq r-1$, and
m and n are each a repeat unit number, m is an integer of 0-1000 and n is an integer of 1-1000, and n/(m+n) is a number within the range of 0.01-1.00.

[17] A sugar residue-modified oligosaccharide-containing polyurethane represented by the following formula [1-1]:

$$—\{[CO—NH—R^1—NH—CO]—[O—R^2—O]\}_m—\#$$
$$(O_2C\text{-}R^3—CO—NH—R^4)_p$$
$$\#—\{[CO—NH—R^1—NH—CO]-[O\text{-}OLS\text{-}O]\}_n—$$
$$(HO_2C—R^3\text{-}CO_2)_q \quad (OH)_{r\text{-}p\text{-}q}$$

[1-1]

wherein
$R^1$ is a divalent $C_{1-16}$ hydrocarbon group optionally having substituent(s),
$R^2$ is a divalent group containing the same or different 1 to 100 units in total selected from a $C_{2-12}$ oxyalkylene unit and a divalent $C_{2-12}$ hydrocarbon unit optionally having substituent(s),
$R^3$ is a $C_{2-4}$ alkylene group,
$R^4$ is a monosaccharide- or disaccharide-derived sugar residue,
OLS is an oligosaccharide skeleton having two primary hydroxyl groups,
r shows the total number of secondary hydroxyl groups of oligosaccharide,
p and q are each an integer within the range of $1 \leq p \leq r$, $0 \leq q \leq r-1$, and
m and n are each a repeat unit number, m is an integer of 0-1000 and n is an integer of 1-1000, and n/(m+n) is a number within the range of 0.01-1.00.

[18] The polyurethane of the above-mentioned [17], wherein $R^3$ is an ethylene group.

[19] The polyurethane of the above-mentioned [17], wherein $R^4$ is a sugar residue derived from glucose, mannose or galactose.

[20] The polyurethane of the above-mentioned [17], wherein the oligosaccharide is trehalose, maltose or lactose.

[21] The polyurethane of the above-mentioned [17], wherein the oligosaccharide is cyclo{→6)-α-D-glucopyranosyl-(1→3)-α-D-glucopyranosyl-(1→6)-α-D-glucopyranosyl-(1→3)-α-D-glucopyranosyl-(1→}.

[22] A carboxyl group-modified oligosaccharide-containing polyurethane represented by the following formula [1-2]:

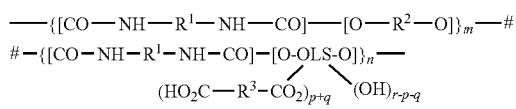

[1-2]

wherein $R^1$ is a divalent $C_{1-6}$ hydrocarbon group optionally having substituent(s), $R^2$ is a divalent group containing the same or different 1 to 100 units in total selected from a $C_{2-12}$ oxyalkylene unit and a divalent $C_{2-12}$ hydrocarbon unit optionally having substituent(s), $R^3$ is a $C_{2-4}$ alkylene group, OLS is an oligosaccharide skeleton having two primary hydroxyl groups, r shows the total number of secondary hydroxyl groups of oligosaccharide, p and q are each an integer within the range of $1 \leq p \leq r$, $0 \leq q \leq r-1$, and m and n are each a repeat unit number, m is an integer of 0-1000 and n is an integer of 1-1000, and n/(m+n) is a number within the range of 0.01-1.00.

[23] The polyurethane of the above-mentioned [22], wherein $R^3$ is an ethylene group.

[24] The polyurethane of the above-mentioned [22], wherein $R^4$ is derived from glucose, mannose or galactose sugar residue.

[25] The polyurethane of the above-mentioned [22], wherein the oligosaccharide is trehalose, maltose or lactose.

[26] The polyurethane of the above-mentioned [22], wherein the oligosaccharide is cyclo{→6)-α-D-glucopyranosyl-(1→3)-α-D-glucopyranosyl-(1→6)-α-D-glucopyranosyl-(1→3)-α-D-glucopyranosyl-(1→}.

[27] An acid-modified oligosaccharide-containing polyurethane represented by the following formula [2-1]:

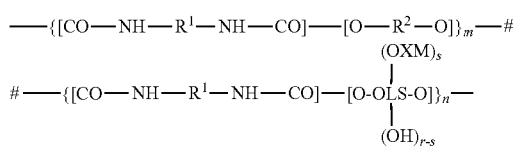

[2-1]

wherein $R^3$ is a divalent $C_{1-16}$ hydrocarbon group optionally having substituent(s), $R^2$ is a divalent group containing the same or different 1 to 100 units in total selected from a $C_{2-12}$ oxyalkylene unit and a divalent $C_{2-12}$ hydrocarbon unit optionally having substituent(s), OLS is an oligosaccharide skeleton having two primary hydroxyl groups, r shows the total number of secondary hydroxyl groups of oligosaccharide, XM is an acid-containing group wherein M is a hydrogen atom, an alkali metal atom, an ammonium group or an organic amino group, and X is an acid-derived moiety, s is the number of the secondary hydroxyl groups of an oligosaccharide modified with an acid-containing group, which is an integer within the range of $1 \leq s \leq r$, and m and n are each a repeat unit number, m is an integer of 0-1000 and n is an integer of 1-1000, and n/(m+n) is a number within the range of 0.01-1.00.

[28] The polyurethane of the above-mentioned [27], wherein X is $SO_3$ or $PO_3$.

[29] The polyurethane of the above-mentioned [27], wherein X is $SO_3$.

[30] The polyurethane of the above-mentioned [27], wherein $R^3$ is an ethylene group.

[31] The polyurethane of the above-mentioned [27], wherein $R^4$ is glucose, mannose or galactose.

[32] The polyurethane of the above-mentioned [27], wherein the oligosaccharide is trehalose, maltose or lactose.

[33] The polyurethane of the above-mentioned [27], wherein the oligosaccharide is cyclo{→6)-α-D-glucopyranosyl-(1→3)-α-D-glucopyranosyl-(1→6)-α-D-glucopyranosyl-(1→3)-α-D-glucopyranosyl-(1→}.

[34] An acid-modified sugar residue-modified oligosaccharide-containing polyurethane represented by the following formula [3-1]:

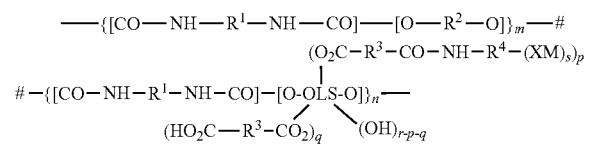

[3-1]

wherein $R^1$ is a divalent $C_{1-36}$ hydrocarbon group optionally having substituent(s), $R^2$ is a divalent group containing the same or different 1 to 100 units in total selected from a $C_{2-12}$ oxyalkylene unit and a divalent $C_{2-12}$ hydrocarbon unit optionally having substituent(s), $R^3$ is a $C_{2-4}$ alkylene group, $R^4$ is a monosaccharide- or disaccharide-derived sugar residue, XM is an acid-containing group wherein M is a hydrogen atom, an alkali metal atom, an ammonium group or an organic amino group, and X is an acid-derived moiety, s is the number of hydroxyl groups of a sugar residue $R^4$ modified with an acid-containing group, which is an integer within the range of $1 \leq s \leq 4$, OLS is an oligosaccharide skeleton having two primary hydroxyl groups, r shows the total number of secondary hydroxyl groups of oligosaccharide, p and q are each an integer within the range of $1 \leq p \leq r$, $0 \leq q \leq r-1$, and m and n are each a repeat unit number, m is an integer of 0-1000 and n is an integer of 1-1000, and n/(m+n) is a number within the range of 0.01-1.00.

[35] The polyurethane of the above-mentioned [34], wherein X is $SO_3$ or $PO_3$.

[36] The polyurethane of the above-mentioned [34], wherein X is $SO_3$.

[37] The polyurethane of the above-mentioned [34], wherein $R^3$ is an ethylene group.

[38] The polyurethane of the above-mentioned [34], wherein $R^4$ is glucose, mannose or galactose.

[39] The polyurethane of the above-mentioned [34], wherein the oligosaccharide is trehalose, maltose or lactose.

[40] The polyurethane of the above-mentioned [34], wherein the oligosaccharide is cyclo{→6)-α-D-glucopyranosyl-(1→3)-α-D-glucopyranosyl-(1→6)-α-D-glucopyranosyl-(1→3)-α-D-glucopyranosyl-(1→}.

[41] A method of harvesting a cell comprising performing
1) a step for trapping a cell on an isolation material by contacting a body fluid with the isolation material comprising, on at least a part of a surface thereof, a substance having a sugar structure,
2) a step for removing untrapped cells by washing the isolation material with a washing liquid, and
3) a step for collecting a trapped cell from the isolation material, in this order, wherein the substance having a sugar structure is a polyurethane of any one of the above-mentioned [17]-[40].

[42] A monocyte isolation material comprising, on at least a part of a surface thereof, a substance having a sugar structure, wherein the substance having a sugar structure is a sugar chain-containing polymer having, as a partial structure, (i) a monosaccharide derivative, an oligosaccharide derivative and/or a polysaccharide derivative, each having a reactive functional group, or (ii) a monosaccharide derivative, an oligosaccharide derivative and/or a polysaccharide derivative.

[43] The monocyte isolation material of the above-mentioned [42], wherein the sugar constituting the substance having a sugar structure is at least one sugar selected from the group consisting of mannose, glucose, galactose, lactose, fucose, trehalose, maltose and cyclo{→6)-α-D-glucopyranosyl-(1→3)-α-D-glucopyranosyl-(1→6)-α-D-glucopyranosyl-(1→3)-α-D-glucopyranosyl-(1→}.

[44] The monocyte isolation material of the above-mentioned [43], wherein the sugar constituting the substance having a sugar structure is at least one sugar selected from the group consisting of mannose, glucose, galactose, lactose and fucose.

[45] The monocyte isolation material of any one of the above-mentioned [42]-[44], having the form of a filter.

[46] A monocyte isolation device comprising a container provided with a liquid inlet and/or a liquid outlet, wherein the container comprises a monocyte isolation material of any one of the above-mentioned [42]-[45] in at least one part thereof.

[47] A physiological material comprising a polyurethane of any one of the above-mentioned [17]-[40].

[48] An isolation material comprising a polyurethane of any one of the above-mentioned [17]-[40] at least on a part of a surface thereof.

[49] The isolation material of the above-mentioned [48], which is a cell isolation material.

[50] The isolation material of the above-mentioned [49], which is a monocyte isolation material.

[51] The isolation material of the above-mentioned [48], which is a protein isolation material.

[52] The isolation material of the above-mentioned [51], which is a lectin isolation material.

[53] The isolation material of the above-mentioned [52], which is a concanavalin A (ConA) or wheat germ agglutinin (WGA) isolation material.

[54] The isolation material of the above-mentioned [48], which is a blood isolation material.

[55] The isolation material of any one of the above-mentioned [48]-[54], having the form of a filter.

[56] An isolation device comprising a container provided with a liquid inlet and/or a liquid outlet, wherein the container comprises an isolation material of the above-mentioned [48]-[55] in at least one part thereof.

[57] The isolation device of the above-mentioned [56], which is a cell isolation device.

[58] The isolation device of the above-mentioned [57], which is a monocyte isolation device.

[59] The isolation device of the above-mentioned [56], which is a protein isolation device.

[60] The isolation device of the above-mentioned [59], which is a lectin isolation device.

[61] The isolation device of the above-mentioned [60], which is a concanavalin A (ConA) or wheat germ agglutinin (WGA) isolation device.

[62] A method of producing a carboxyl group-modified oligosaccharide-containing polyurethane represented by the following formula [1-2]:

$$\text{---}\{[CO\text{---}NH\text{---}R^1\text{---}NH\text{---}CO]\text{---}[O\text{---}R^2\text{---}O]\}_m\text{---}\# \quad [1\text{-}2]$$
$$\#\text{---}\{[CO\text{---}NH\text{---}R^1\text{---}NH\text{---}CO]\text{---}[O\text{-}OLS\text{-}O]\}_n\text{---}$$
$$(HO_2C\text{---}R^3\text{---}CO_2)_{p+q} \quad (OH)_{r-p-q}$$

wherein
$R^1$ is a divalent $C_{1-16}$ hydrocarbon group optionally having substituent(s), $R^2$ is a divalent group containing the same or different 1 to 100 units in total selected from a $C_{2-12}$ oxyalkylene unit and a divalent $C_{2-12}$ hydrocarbon unit optionally having substituent(s), $R^3$ is a $C_{2-4}$ alkylene group, m and n are each a repeat unit number, m is an integer of 0-1000 and n is an integer of 1-1000, and n/(m+n) is a number within the range of 0.01-1.00, OLS is an oligosaccharide skeleton having two primary hydroxyl groups, r shows the total number of secondary hydroxyl groups of oligosaccharide, and p and q are as defined above, comprising reacting an oligosaccharide-containing polyurethane represented by the following formula [1-3]:

$$\text{---}\{[CO\text{---}NH\text{---}R^1\text{---}NH\text{---}CO]\text{---}[O\text{---}R^2\text{---}O]\}_m\text{---}\# \quad [1\text{-}3]$$
$$\#\text{---}\{[CO\text{---}NH\text{---}R^1\text{---}NH\text{---}CO]\text{---}[O\text{-}OLS\text{-}O]\}_n\text{---}$$
$$(OH)_r$$

wherein $R^1$, $R^2$, m, n, r and OLS are each as defined above, with an acid anhydride represented by the following formula [1-4]:

$$\begin{array}{c} CO-O \\ | \quad | \\ R^3-CO \end{array} \qquad [1\text{-}4]$$

wherein $R^3$ is as defined above.

[63] A method of producing a sugar residue-modified oligosaccharide-containing polyurethane represented by the following formula [1-1]

$$\begin{array}{c} -\!\!\{[CO-NH-R^1-NH-CO]-\![O-R^2-O]\}_m-\!\!\# \\ (O_2C-R^3-CO-NH-R^4)_p \\ | \\ \#-\!\{[CO-NH-R^1-NH-CO]-[O\text{-}OLS\text{-}O]\}_n-\!\! \\ (HO_2C-R^3-CO_2)_q \quad (OH)_{r\text{-}p\text{-}q} \end{array} \qquad [1\text{-}1]$$

wherein $R^1$ is a divalent $C_{1-16}$ hydrocarbon group optionally having substituent(s), $R^2$ is a divalent group containing the same or different 1 to 100 units in total selected from a $C_{2-12}$ oxyalkylene unit and a divalent $C_{2-12}$ hydrocarbon unit optionally having substituent(s), $R^3$ is a $C_{2-4}$ alkylene group, $R^4$ is a monosaccharide- or disaccharide-derived sugar residue, OLS is an oligosaccharide skeleton having two primary hydroxyl groups, r shows the total number of secondary hydroxyl groups of oligosaccharide, p and q are each an integer within the range of $1 \leq p \leq r$, $0 \leq q \leq r-1$, and m and n are each a repeat unit number, m is an integer of 0-1000 and n is an integer of 1-1000, and n/(m+n) is a number within the range of 0.01-1.00, comprising reacting a carboxyl group-modified oligosaccharide-containing polyurethane represented by the following formula [1-2]:

$$\begin{array}{c} -\!\!\{[CO-NH-R^1-NH-CO]-\![O-R^2-O]\}_m-\!\!\# \\ \#-\!\{[CO-NH-R^1-NH-CO]-[O\text{-}OLS\text{-}O]\}_n-\!\! \\ (HO_2C-R^3-CO_2)_{p+q} \quad (OH)_{r\text{-}p\text{-}q} \end{array} \qquad [1\text{-}2]$$

wherein $R^1$, $R^2$, $R^3$, p, q, r, m, n and OLS are each as defined above, with an aminated sugar represented by the following formula [1-5]:

$$R^4-NH_2 \qquad [1\text{-}5]$$

wherein $R^4$ is as defined above.

[64] A method of producing an acid-modified oligosaccharide-containing polyurethane represented by the following formula [2-1]:

$$\begin{array}{c} -\!\!\{[CO-NH-R^1-NH-CO]-\![O-R^2-O]\}_m-\!\!\# \\ (OXM)_s \\ | \\ \#-\!\{[CO-NH-R^1-NH-CO]-[O\text{-}OLS\text{-}O]\}_n-\!\! \\ | \\ (OH)_{r\text{-}s} \end{array} \qquad [2\text{-}1]$$

wherein $R^1$ is a divalent $C_{1-16}$ hydrocarbon group optionally having substituent(s), $R^2$ is a divalent group containing the same or different 1 to 100 units in total selected from a $C_{2-12}$ oxyalkylene unit and a divalent $C_{2-12}$ hydrocarbon unit optionally having substituent(s), OLS is an oligosaccharide skeleton having two primary hydroxyl groups, r shows the total number of secondary hydroxyl groups of oligosaccharide, s is as defined above, X is an acid-derived moiety, and m and n are each a repeat unit number, m is an integer of 0-1000 and n is an integer of 1-1000, and n/(m+n) is a number within the range of 0.01-1.00, comprising reacting an oligosaccharide-containing polyurethane represented by the following formula [1-3]:

$$\begin{array}{c} -\!\!\{[CO-NH-R^1-NH-CO]-\![O-R^2-O]\}_m-\!\!\# \\ \#-\!\{[CO-NH-R^1-NH-CO]-[O\text{-}OLS\text{-}O]\}_n-\!\! \\ | \\ (OH)_r \end{array} \qquad [1\text{-}3]$$

wherein $R^1$, $R^2$, OLS, r, m and n are as defined above, with an acid modifying reagent.

[65] The production method of the above-mentioned [64], wherein the acid modifying reagent is a sulfating reagent or a phosphorylation reagent.

[66] The production method of the above-mentioned [65], wherein the acid modifying reagent is a sulfating reagent.

[67] A method of producing an acid-modified sugar residue-modified oligosaccharide-containing polyurethane represented by the following formula [3-1]:

$$\begin{array}{c} -\!\!\{[CO-NH-R^1-NH-CO]-\![O-R^2-O]\}_m-\!\!\# \\ (O_2C-R^3-CO-NH-R^4-(XM)_s)_p \\ | \\ \#-\!\{[CO-NH-R^1-NH-CO]-[O\text{-}OLS\text{-}O]\}_n-\!\! \\ (HO_2C-R^3-CO_2)_q \quad (OH)_{r\text{-}p\text{-}q} \end{array} \qquad [3\text{-}1]$$

wherein $R^1$ is a divalent $C_{1-16}$ hydrocarbon group optionally having substituent(s), $R^2$ is a divalent group containing the same or different 1 to 100 units in total selected from a $C_{2-12}$ oxyalkylene unit and a divalent $C_{2-12}$ hydrocarbon unit optionally having substituent(s), $R^3$ is a $C_{2-4}$ alkylene group, $R^4$ is a monosaccharide- or disaccharide-derived sugar residue, XM is an acid-containing group wherein M is a hydrogen atom, an alkali metal atom, an ammonium group or an organic amino group, and X is an acid-derived moiety, s is the number of hydroxyl groups of a sugar residue $R^4$ modified with an acid-containing group, which is an integer within the range of $1 \leq s \leq 4$, OLS is an oligosaccharide skeleton having two primary hydroxyl groups, r shows the total number of secondary hydroxyl groups of oligosaccharide, p and q are each an integer within the range of $1 \leq p \leq r$, $0 \leq q \leq r-1$, m and n are each a repeat unit number, m is an integer of 0-1000 and n is an integer of 1-1000, $n/(m+n)$ is a number within the range of 0.01-1.00, comprising reacting a sugar residue-modified oligosaccharide-containing polyurethane represented by the following formula [1-1]:

$$[1\text{-}1]$$

$$—\{[CO—NH—R^1—NH—CO]—[O—R^2—O]\}_m—\#$$
$$(O_2C—R^3—CO—NH—R^4)_p$$
$$\#—\{[CO—NH—R^1-NH—CO]-[O\text{-}OLS\text{-}O]\}_n—$$
$$(HO_2C—R^3\text{-}CO_2)_q \quad (OH)_{r\text{-}p\text{-}q}$$

wherein $R^1$ is a divalent $C_{1\text{-}16}$ hydrocarbon group optionally having substituent(s), $R^2$ is a divalent group containing the same or different 1 to 100 units in total selected from a $C_{2\text{-}12}$ oxyalkylene unit and a divalent $C_{2\text{-}12}$ hydrocarbon unit optionally having substituent(s), $R^3$ is a $C_{2\text{-}4}$ alkylene group, $R^4$ is a monosaccharide- or disaccharide-derived sugar residue, OLS is an oligosaccharide skeleton having two primary hydroxyl groups, r shows the total number of secondary hydroxyl groups of oligosaccharide, p and q are each an integer within the range of $1 \leq p \leq r$, $0 \leq q \leq r-1$, m and n are each a repeat unit number, m is an integer of 0-1000 and n is an integer of 1-1000, $n/(m+n)$ is a number within the range of 0.01-1.00, with an acid modifying reagent.

[68] The production method of the above-mentioned [67], wherein the acid modifying reagent is a sulfating reagent or a phosphorylation reagent.

[69] The production method of the above-mentioned [68], wherein the acid modifying reagent is a sulfating reagent.

BEST MODE FOR CARRYING OUT THE INVENTION

The present invention is specifically explained in the following.

The isolation material to be used for the method of the present invention characteristically contains a substance having a sugar structure on at least a part of the surface. In the present invention, "contains a substance having a sugar structure on at least a part of the surface" encompasses both cases where 1) the isolation material itself is constituted with a substance having a sugar structure, and 2) the substrate of the isolation material is different from the substance having a sugar structure, and the entirety or a part of the surface of the isolation material is constituted with a substance having a sugar structure.

The "substance having a sugar structure" to be used in the method of the present invention is not particularly limited as long as it contains monosaccharide, oligosaccharide and/or polysaccharide structures as a partial structure, which can be formed into an isolation material by itself, or immobilized or coated on the surface of a substrate of the isolation material. For example, a monosaccharide derivative, an oligosaccharide derivative and/or a polysaccharide derivative, each having a reactive functional group, a sugar chain-containing polymer having, as a partial structure, a monosaccharide, an oligosaccharide and/or a polysaccharide, and the like can be mentioned.

While the kind of sugar in a substance having a sugar structure is not particularly limited, monosaccharides such as mannose, glucose, galactose, fucose and the like, and oligosaccharide or polysaccharide containing these sugar units are preferable. Examples thereof include mannose, glucose, galactose, lactose, fucose, trehalose, maltose, cyclo{1→6)-α-D-glucopyranosyl-(1→3)-α-D-glucopyranosyl-(1→6)-α-D-glucopyranosyl-(1→3)-α-D-glucopyranosyl-(1→} and the like.

The kind of sugar may be single or plural. The sugar structure means a partial structure or derivative of these sugars. When the sugar of the sugar structure is oligosaccharide or polysaccharide, it may have a straight chain structure or a branched structure. The terminal sugar of a sugar structure preferably has a structure selected from glucose, galactose and fucose. The terminal sugar here means a sugar on the terminal at the nonreducing terminal side.

In the isolation material of the present invention, when a substance having a sugar structure is immobilized on a substrate of the isolation material, the immobilizing method includes an ion bond method, a covalent bond method and the like. As the immobilization method, various known methods can be used without any particular limitation. In this case, a monosaccharide derivative, an oligosaccharide derivative and a polysaccharide derivative, each having a reactive functional group, are preferably used as substances having a sugar structure. The reactive functional group of a monosaccharide derivative, an oligosaccharide derivative and/or a polysaccharide derivative is not particularly limited as long as it can chemically bind to a substrate of the isolation material directly or via a spacer. For example, a hydroxyl group, an amino group, an aldehyde group, a carboxyl group, a thiol group, a silanol group, an amide group, an epoxy group, a halogen group, a succinoylimide group, an acid anhydride group and the like can be mentioned. When a monosaccharide derivative, an oligosaccharide derivative and/or a polysaccharide derivative, each having a reactive functional group is immobilized on an isolation material, a reactive group may be introduced onto the surface of a substrate of the isolation material. For introduction of a reactive group, for example, immobilization of halogen or pseudohalogen as disclosed in JP-A-2-261833, introduction of an epoxy group as disclosed in JP-A-6-219051 and JP-B-1887096, and the like are preferably utilized. In addition, a substance having a sugar structure or a precursor thereof can also be immobilized by graft polymerization onto a substrate of the isolation material. In this case, monosaccharide, oligosaccharide and/or polysaccharide derivative, having, as a reactive functional group, a styrene group, a methacryl group, a vinyl group, an acrylic group and the like capable of graft polymerization can be used as a substance having a sugar structure. As an immobilization method therefor, known methods using radiation or electron beam can be employed without any particular limitation.

In the isolation material to be used in the present invention, when a substrate of the isolation material is coated with a substance having a sugar structure, a sugar chain-containing polymer having monosaccharide, oligosaccharide and/or polysaccharide as a partial structure is preferably used as the substance having a sugar structure. Examples of such sugar chain-containing polymer include synthetic polymers represented by polyurethane, polystyrene, polyethylene, polyolefin, polyacrylamide, polyester, nylon, polyimide, aramid, polyamide, acrylic resin and the like, natural polymers represented by chitin, chitosan, acetyl cellulose, cellulose, rayon, agarose, alginic acid and the like, into which at least one kind of monosaccharide, oligosaccharide and/or polysaccharide structure has been introduced, and the like.

While the method of coating a substrate of the isolation material with a substance having a sugar structure is not particularly limited, for example, coating methods including immersing a substrate of the isolation material into a liquid containing a substance having a sugar structure which forms a coating layer, spraying the solution on a substrate of the isolation material, injecting the solution on a substrate of the isolation material and the like can be mentioned. The substrate after a coating treatment may be used after removing the remaining solution by washing, or used after drying without washing. Alternatively, the substrate may be used after washing but without drying, and known methods can be used without any particular limitation. Moreover, a coating layer may be formed by applying a solution containing a substance having a sugar structure and a polymerizable compound in combination, and crosslinking the solution.

The form of the isolation material of the present invention is not particularly limited and may be, for example, a tool having a flat plate structure such as petri dish, flask, plate, bag, cartridge, cassette and the like, a structure having continuous pores (e.g., filter) such as non-woven fabric, fiber, porous material, spherical carrier and the like, and the like.

When a substrate of the isolation material to be used in the present invention is petri dish, flask, plate, bag, cartridge, cassette and the like, its form and size are not particularly limited. The materials thereof are not particularly limited. However, an inert polymer, or a metal material such as bioaffinity metal, alloy thereof and the like, and the like are preferably used. Alternatively, a material coated or plated with such inert polymer, bioaffinity metal and the like may be used.

Examples of the inert polymer include acrylonitrile polymers such as acrylonitrile-butadiene-styrene copolymer and the like, halogenated polymers such as polytetrafluoroethylene, polychlorotrifluoroethylene, tetrafluoroethylene, polyhexafluoropropylene and the like, polyamide, polysulfone, polycarbonate, polyethylene, polypropylene, vinyl chloride-acrylic copolymer, carbonate-acrylonitrile-butadiene-styrene copolymer, styrene-butadiene copolymer, polystyrene and the like.

Examples of the metal material include stainless steel, titanium, platinum, tantalum, gold, alloys thereof, as well as gold-plated alloy iron, platinum-plated alloy iron, cobalt chromium alloy, titanium nitride-coated stainless steel and the like.

Among these, a germproof or sterile material is particularly preferable. Specifically, glass, polypropylene, polyvinyl chloride, polycarbonate, polysulphone, polymethylpentene and the like coated with silicon can be mentioned.

When a substrate of the isolation material to be used in the present invention is petri dish, flask, plate, bag, cartridge, cassette and the like, a material having a gas permeable structure is also used preferably. Examples of the material having a gas permeable structure include a material having an ultrafine pore structure or a slit structure of the level permitting suppression of contamination, a material inherently having high gas permeability and the like. Examples of the material inherently having high gas permeability include, but are not limited to, polymethylpentene, cyclic polyolefin, olefin type thermoplastic elastomer, styrene type thermoplastic elastomer, polyamide type thermoplastic elastomer and the like.

A substrate of the isolation material to be used in the present invention may be a non-woven fabric or a porous material. In this case, an average pore size of the substrate is, for example, preferably within the range of 9 µm-80 µm. While the material of the substrate is not particularly limited, it is, for example, a synthetic polymer such as polyurethane, polystyrene, polyethylene, polyolefin, polyacrylamide, polyester, nylon, polyimide, aramid, polyamide, acrylic resin and the like, a natural polymer such as chitin, chitosan, acetyl cellulose, cellulose, rayon, agarose, alginic acid and the like, an inorganic material such as hydroxyapatite, glass, alumina and the like, a metal such as stainless, titanium and the like, and the like.

The porous state form may be any form such as sponge-like, felt-like, cotton-like, fiber-like, particles-like, pipy, discotic and cylindrical shape forms and the like. When a substrate of the isolation material is a spherical carrier, its particle size is preferably 10 µm-2000 µm, more preferably 70 µm-1000 µm, from treatment efficiency. Examples of the material of the spherical carrier include, but are not limited to, inorganic carriers such as glass beads, silica gel and the like, synthetic polymer compounds such as crosslinked polyvinyl alcohol, crosslinked polyacrylate, crosslinked polyacrylamide, crosslinked polystyrene, ethylene-vinyl acetate copolymer saponifiable substance, crosslinked polyacrylic acid, crosslinked polymethacrylic acid, polymethyl methacrylate, polyacrylamide grafted polyethylene and the like, organic carrier comprised of polysaccharides such as crystalline cellulose, crosslinked cellulose, cellulose derivatives, crosslinked agarose, crosslinked dextrin, chitin, chitosan and the like, composite carriers obtained by combining them, such as organic-organic, organic-inorganic composite carriers and the like, and the like.

The above-mentioned isolation material may be directly used as a harvesting method of cell, protein and the like, or can also be used in the form of an isolation device.

In the present invention, the "isolation device" means a device wherein the aforementioned isolation material is contained at least in one part of a container having a liquid inlet and/or a liquid outlet. The isolation material preferably used for the isolation device of the present invention is a structure having continuous pores, such as non-woven fabric, fiber, porous material, spherical carrier, filter and the like. The isolation device of the present invention refers to a device wherein such isolation material structure is mounted on or filled in a container suitable for the form thereof, such as column, bag, cassette and the like, or housed in an incubator such as flask, bag and the like, and the like. Preferably, the aforementioned isolation material is filled in the aforementioned container.

The form, material and size of the container are not particularly limited, and any form such as dish/bottle, bag, tube, column, cassette, flask and the like may be employed. Examples of the isolation device of the present invention include an isolation device in the form of a column of an about 0.1-500 ml transparent or translucent cylindrical container having a diameter of about 0.1-10 cm filled with a structure having continuous pores such as spherical carrier etc., and the like.

The device is preferably mounted on or filled in a container having a body fluid inlet and a body fluid outlet to divide the body fluid inlet from the body fluid outlet to give a filter or a cross-flow module. When a non-woven fabric or a porous material is mounted on or filled in a container, it may form a single layer or a laminate of a plurality thereof, or it may also be combined with a material having a surface not constituted with a substance having a sugar structure and then mounted on or filled in a container.

Such isolation device is useful for harvesting, for example, cell (e.g., monocyte and the like), protein (e.g., lectin such as ConA (concanavalin A), WGA (wheat germ agglutinin) etc., and the like) and the like.

While the material of the container for the isolation device of the present invention is not particularly limited, inert polymer or a metal material such as a bioaffinity metal or an alloy thereof etc., and the like are used. Alternatively, a material coated or plated with such inert polymer or bioaffinity metal may be used.

Examples of the inert polymer include acrylonitrile polymers such as acrylonitrile-butadiene-styrene copolymer and the like, halogenated polymers such as polytetrafluoroethylene, polychlorotrifluoroethylene, tetrafluoroethylene, polyhexafluoropropylene and the like, polyamide, polysulfone, polycarbonate, polyethylene, polypropylene, vinyl chloride-acrylic copolymer, carbonate-acrylonitrile-butadiene-styrene copolymer, styrene-butadiene copolymer, polystyrene and the like.

Examples of the metal material include stainless steel, titanium, platinum, tantalum, gold, and alloys thereof, as well as gold-plated alloy iron, platinum-plated alloy iron, cobalt chromium alloy, titanium nitride-coated stainless steel and the like.

Among these, a germproof or sterile material is particularly preferable. Specific examples include glass, polypropylene, polyvinyl chloride, polycarbonate, polysulphone, polymethylpentene and the like coated with silicon.

[Cell Harvesting Method]

A cell harvesting method using the isolation material of the present invention is explained in detail in the following.

A method of harvesting a cell in the present invention includes contacting the aforementioned isolation material of the present invention with a body fluid, and specifically includes the following steps 1)-3) in this order:

1) step for trapping a cell (e.g., monocyte and the like) in an isolation material by contacting a body fluid with the isolation material containing, on at least a part of the surface, a substance having a sugar structure, 2) a step for removing untrapped cells by washing the isolation material with a washing liquid, and 3) a step for collecting a trapped cell from the isolation material.

In the above-mentioned method, the isolation material can also be used in the form of the aforementioned isolation device.

In the method of the present invention, the "body fluid" encompasses, but is not limited to, blood (e.g., peripheral blood, cord blood, peripheral blood induced by cytokines (e.g., G-CSF and the like) and the like), bone marrow, lymph, pleural fluid, ascites, synovia and the like harvested from a living organism, for example, mammals (human, monkey, rat, mouse, dog, cat, rabbit, bovine, swine, sheep, goat, horse and the like, preferably human) sample, as well as apheresis products, centrifugation treatment liquid, cell suspension (e.g., including cell suspension containing cells subjected to a specific gravity density centrifugation treatment using, when desired, ficoll, percoll, vacutainer tube, lymphoprep, HES (hydroxyethylstarch) and the like) and the like, of these body fluids.

The method of the present invention is particularly suitable for blood as a body fluid.

A body fluid can be harvested from a test sample by any method known in the field. For collection of a body fluid, heparin, low molecular weight heparin, nafamostat mesylate, gabexate mesylate, aragatroban, a citric acid-containing anticoagulant such as acid citrate dextrose liquid (ACD liquid), citrate phosphate dextrose liquid (CPD liquid) and the like, and the like may be used as a generally used anticoagulant. Among these, citric acid-containing anticoagulant and heparin are most preferable.

Each step of the method of the present invention is explained in detail in the following by referring to each representative embodiment using an isolation material and an isolation device.

<When isolation material or a substrate thereof takes the form of petri dish, flask, plate, bag, cartridge, cassette and the like>

Step 1)

In step 1), a cell is trapped in an isolation material by contacting a body fluid with an isolation material containing a substance having a sugar structure in at least one part of a surface. To be specific, a target body fluid is injected into the isolation material of the present invention using a petri dish, a flask, a plate, a bag, a cartridge, a cassette and the like as a substrate, and the material is stood or shaken for 5 min-120 min to contact the body fluid with the isolation material, whereby cell is trapped in the isolation material. For stable trapping of the cell and reduced damage on the cell, the contact (standing or shaking) time is more preferably 15 min-90 min.

Step 2)

In step 2), the isolation material is washed with a washing liquid to remove untrapped cells. While a method of removing the untrapped cells is not particularly limited, for example, a method wherein a body fluid is first removed by suction with a pipette, a syringe and the like or decantation and the like, saline, culture medium, buffered solution and the like are injected again in the isolation material to wash away the attached cells, and finally, the supernatant is removed by the aforementioned suction or decantation and the like, and the like can be mentioned. When removal of the untrapped cells is insufficient, the method may be repeated several times.

Step 3)

In step 3), the trapped cell is collected from the isolation material. The trapped cell can be collected, for example, by contacting a collection liquid containing saline, a medium, a cell preservation solution and the like, a divalent cation chelating agent such as acid citrate dextrose liquid (ACD liquid), citrate phosphate dextrose liquid (CPD liquid) and the like, a sugar-containing cell collection liquid and the like with the isolation material after washing in the above-mentioned step 2).

While the kind of the collection liquid is not particularly limited, from the aspects of cell recovery rate, a cell collection liquid containing the same kind of sugar as the sugar structure constituting a part of the isolation material, for example, a cell collection liquid containing sugar such as mannose, glucose, galactose, fucose or a mixture thereof is preferably used. The sugar concentration of a sugar-containing cell collection liquid may be any from 0.01% (W/V) to the saturated solubility of the sugar at 37° C. From the aspects of collection efficiency, it is preferably 0.1% (W/V)-half the saturated solubility, more preferably 0.5% (W/V)-⅕ of the saturated solubility. In addition, the sugar-containing cell collection liquid may contain, where necessary, a divalent cation chelating agent such as acid citrate dextrose liquid (ACD liquid), citrate phosphate dextrose liquid (CPD liquid) and the like.

The cells are contacted with the above-mentioned cell collection liquid for about 3 min-30 min while standing or shaking them. After contact for a given time, cells can be collected by pipetting, application of vibration, pushing the collection liquid swiftly while preventing damage on the trapped cells (for example, flashing and the like) and the like. The means for pushing may be, but not limited to, air, inert gas, saline and the like. In this case, to increase collection efficiency, cooling down to 4° C. or heating up to 37° C. may be concurrently performed. When the cell recovery rate is insufficient, the above-mentioned collection operation may be repeated.

<When an isolation device comprising an isolation material having a structure with continuous pores such as non-woven fabric, fiber, porous material, spherical carrier, filter and the like in at least one part of a container is used>

Here, a case using an isolation material in the form of an isolation device is particularly explained.

Step 1)

In step 1), a cell is trapped in an isolation material by contacting a body fluid with a device comprising the above-mentioned isolation material in at least one part of a container having a liquid inlet and/or a liquid outlet.

When the above-mentioned isolation device is used, "contacting a body fluid with an isolation device" means passing a body fluid through an isolation device. Here, passing a liquid means introducing a body fluid from a liquid inlet of an isolation device, transporting the fluid in a given direction and discharging the fluid from a liquid outlet. The means for introducing a body fluid into an isolation device may be, but not limited to, a method including use of a machine such as a syringe pump, a peristaltic pump and the like, manual liquid passage using a syringe, a free fall treatment utilizing difference in height and the like. The liquid passage rate is preferably 0.1 ml/min-100 ml/min, and a body fluid may be passed through the device once, or plural times by a circulation treatment.

Step 2)

In step 2), the isolation device is washed with a washing liquid to remove untrapped cells. When the above-mentioned isolation device is used, untrapped cells are removed from the isolation material by passing a washing liquid through the isolation device from a liquid inlet (same direction as body fluid flow entry direction) or a liquid outlet (opposite direction to body fluid flow entry direction). Specific examples of the washing liquid include, but are not limited to, saline, Ringer's solution, buffer such as phosphate buffer and the like, cell culture medium such as RPMI1640 and the like. The means for introducing a washing liquid may be, but is not limited to, a method including use of a machine such as a syringe pump, a peristaltic pump and the like, manual liquid passage using a syringe, a free fall treatment utilizing difference in height and the like. The flow rate of liquid passage using a pump is about 0.1 ml/min-100 ml/min. While the amount of the washing liquid varies depending on the isolation material used for an isolation device and the content volume of the isolation device, washing with a volume of about 1- to 5-fold the content volume is preferable.

Step 3)

In step 3), the trapped cell is collected from the isolation device. To be specific, the trapped cell is collected, for example, by passing a collection liquid containing saline, a medium, a cell preservation solution and the like, a collection liquid containing a divalent cation chelating agent such as acid citrate dextrose liquid (ACD liquid), citrate phosphate dextrose liquid (CPD liquid) and the like, a sugar-containing cell collection liquid, and the like through the above-mentioned isolation device.

Particularly, in view of cell collection efficiency, a cell collection liquid containing the same kind of sugar as the sugar structure constituting a part of the isolation material in a separation device, for example, a collection liquid containing mannose, glucose, galactose, fucose or a mixture thereof is preferably used. When a sugar-containing cell collection liquid is used as a collection liquid, the sugar concentration of a collection liquid may be any from 0.01% (W/V) to the saturated solubility of the sugar at 37° C. From the aspects of collection efficiency, it is preferably 0.1% (W/V)-half the saturated solubility, more preferably 0.5% (W/V)-⅕ of the saturated solubility. In addition, the sugar-containing cell collection liquid may contain a divalent cation chelating agent such as acid citrate dextrose liquid (ACD liquid), citrate phosphate dextrose liquid (CPD liquid) and the like. The above-mentioned isolation device is preferably contacted with the collection liquid for about 3 min-30 min and the contact method may be a leaving method, a circulation method and the like. The flow rate during circulation is preferably 0.1 ml/min-200 ml/min. In this case, to increase collection efficiency, cooling down to 4° C. or heating up to 37° C. may be concurrently performed. When the cell collection is insufficient, the above-mentioned collection operation may be repeated.

The method of the present invention is particularly suitable for harvesting a monocyte. Monocyte is a monocyte type cell derived from a hematopoietic stem cell, and used for the fields of regenerative medicine and cell medicine such as vascular regeneration, differentiation induction into dendritic cells and the like.

When monocytes are collected by the method of the present invention, the obtained monocytes can be used as the cells for vascular regeneration and the like. Alternatively, the monocytes harvested by the method of the present invention can also be used as a precursor cell in the below-mentioned "method of preparing a dendritic cell".

[Method of Preparing a Dendritic Cell]

The present invention also relates to a preparation method of dendritic cell and the dendritic cell obtained the method.

The method of preparing a dendritic cell of the present invention includes a method including a step wherein the monocytes trapped in the isolation material by the above-mentioned method of the present invention are collected from the isolation material and differentiation induction thereof into dendritic cells is induced, and a method including a step wherein the monocytes trapped in the isolation material are, without collection, induced in situ to differentiate into dendritic cells.

In the present invention, dendritic cell means immature dendritic cell obtained by inducing monocyte with cytokines such as IL-4, GM-CSF and the like to differentiate thereinto, mature dendritic cell obtained by inducing immature dendritic cell by adding cytokines such as TNFα, IL-β, IL-6, PGE2 and the like to differentiate thereinto, antigen-presenting dendritic cell (e.g., dendritic cell presenting cancer antigen and the like) obtained via a step of acquiring an antigen-presenting capability (e.g., addition of cancer antigen), and the like.

A method of preparing the dendritic cell of the present invention is explained in detail the following.

<Method of collecting trapped monocytes from the isolation material of the present invention and inducing them to differentiate into dendritic cells>

In this method, dendritic cells can be prepared by harvesting monocytes using the aforementioned method of the present invention, which is followed by induction of differentiation.

A step for inducing the monocytes to differentiate into dendritic cells can be performed, for example, as in the following.

Monocytes are placed in a container generally used for cell culture such as petri dish, flask and the like, and a culture medium containing cytokines such as GM-CSF, IL-4 and the like is added. By culturing the cells for about 1 week, the monocytes can be induced to differentiate into immature dendritic cells. By further culturing the cells in a culture medium containing cytokines such as IL-1β, PGE2, IL-6, TNF-α and the like for about 1 week, immature dendritic cells can be induced to differentiate into mature dendritic cells.

Where necessary, the cells may be induced to differentiate into antigen-presenting dendritic cells (e.g., dendritic cells presenting cancer antigen and the like) via a step of acquiring an antigen-presenting capability (e.g., addition of cancer antigen), and the like.

The obtained dendritic cell can be collected by, for example, a general collection means such as pipetting and the like.

<Method of inducing in situ the monocytes trapped in the isolation material to differentiate into dendritic cells without collection>

A preferable embodiment of this method includes the following steps 1)-4) in this order:

1) a step for trapping monocytes in an isolation material by contacting a body fluid with an isolation material containing, on at least a part of the surface, a substance having a sugar structure, 2) a step for removing untrapped monocytes by washing the isolation material with a washing liquid, 3) a step for inducing further differentiation of the monocytes trapped by the isolation material to give dendritic cells, and 4) a step for collecting the dendritic cells after induced to differentiate into from the isolation material.

Also in this method, the isolation material can be used in the form of an isolation device as mentioned above.

The above-mentioned steps 1) and 2) can be performed according to steps 1) and 2) of the aforementioned "cell harvesting method". Steps 3) and 4) are explained in detail in the following.

When an isolation material is in the form of petri dish, flask, plate, bag, cartridge, cassette and the like Step 3)

In step 3), monocytes trapped in the isolation material are further induced to differentiate into dendritic cells.

To be specific, untrapped cells are removed by washing in step 2), a culture medium containing cytokines such as GM-CSF, IL-4 and the like is added to monocytes trapped in the isolation material, and the monocytes are cultured for about 1 week to differentiated monocytes trapped in the isolation material into immature dendritic cells. Thereafter, the immature dendritic cells are cultured in a culture medium containing cytokines such as IL-1β, PGE2, IL-6, TNF-α and the like for about 1 week to induce differentiation into mature dendritic cells.

Where necessary, the cells may be induced to differentiate into antigen-presenting dendritic cells (e.g., dendritic cells presenting cancer antigen and the like) via a step of acquiring an antigen-presenting capability (e.g., addition of cancer antigen), and the like.

Step 4)

In step 4), the dendritic cell after differentiation induction is collected from the isolation material. The dendritic cell can be collected by a pipetting operation, use of a cell collection liquid containing a divalent cation chelating agent such as an acid citrate dextrose liquid (ACD liquid), a citrate phosphate dextrose liquid (CPD liquid) and the like, and the like, which are generally employed therefor. To realize a higher recovery rate, a collection method using a sugar-containing collection liquid is advantageous. As a preferable sugar-containing collection liquid, a cell collection liquid containing the same kind of sugar as the sugar structure constituting a part of the isolation material, for example, a cell collection liquid containing mannose, glucose, galactose, fucose or a mixture thereof is used. The sugar concentration of a sugar-containing collection liquid may be any from 0.01% (W/V) to the saturated solubility of the sugar at 37° C. From the aspects of collection efficiency, it is preferably 0.1% (W/V)-half the saturated solubility, more preferably 0.5% (W/V)-⅕ of the saturated solubility. In addition, the sugar-containing cell collection liquid may contain, where necessary, a divalent cation chelating agent such as acid citrate dextrose liquid (ACD liquid), citrate phosphate dextrose liquid (CPD liquid) and the like.

The dendritic cell is contacted with the above-mentioned cell collection liquid for about 3 min-30 min by leaving or shaking. After contact for a given time, dendritic cells can be collected by pipetting, application of vibration, pushing the collection liquid swiftly while preventing damage on the dendritic cells (for example, flashing and the like) and the like. The means for pushing out may be, but not limited to, air, inert gas, saline and the like. In this case, to increase collection efficiency, cooling down to 4° C. or heating up to 37° C. may be concurrently performed. When collection of the dendritic cell is insufficient, the above-mentioned collection operation may be repeated.

When isolation device comprised of a container packed with an isolation material comprised of a structure having continuous pores such as non-woven fabric, fiber, porous material, spherical carrier, filter and the like is used Step 3)

In step 3), monocytes trapped in the above-mentioned isolation device are further induced to differentiate into dendritic cells. After removing the untrapped monocytes in step 2), a culture medium containing cytokines such as GM-CSF, IL-4 and the like is passed through an isolation device, after which the monocytes are cultured in a culture medium containing cytokines such as GM-CSF, IL-4 and the like for about 1 week, whereby the monocytes are differentiated into immature dendritic cells. Thereafter, a culture medium containing cytokines such as IL-1β, PGE2, IL-6, TNF-α and the like is further passed, the cells are cultured in a culture medium containing cytokines such as IL-1β, PGE2, IL-6, TNF-α and the like for about 1 week to induce differentiation of the immature dendritic cells into mature dendritic cells.

Where necessary, the cells may be induced to differentiate into antigen-presenting dendritic cells (e.g., dendritic cells presenting cancer antigen and the like) via a step of acquiring an antigen-presenting capability by passing or contacting a culture medium containing an antigen (e.g., cancer antigen).

Step 4)

In step 4), the dendritic cell after differentiation induction in the above-mentioned step 3) is collected from the isolation device. The dendritic cell after differentiation induction can be collected by passing a collection liquid generally used or passing a cell collection liquid containing a divalent cation chelating agent such as an acid citrate dextrose liquid (ACD liquid), a citrate phosphate dextrose liquid (CPD liquid) and the like through the isolation device. To realize a higher recovery rate, a collection method using a sugar-containing collection liquid is advantageous. As a preferable sugar-containing collection liquid, a cell collection liquid containing the same kind of sugar as the sugar structure constituting a part of the isolation device, for example, a collection liquid containing mannose, glucose, galactose, fucose or a mixture thereof is used. The sugar concentration of a sugar-containing collection liquid may be any from 0.01% (W/V) to the saturated solubility of the sugar at 37° C. From the aspects of collection efficiency, it is preferably 0.1% (W/V)-half the saturated solubility, more preferably 0.5% (W/V)-⅕ of the saturated solubility. In addition, the sugar-containing cell collection liquid may contain, where necessary, a divalent cation chelating agent such as acid citrate dextrose liquid (ACD liquid), citrate phosphate dextrose liquid (CPD liquid) and the like.

The dendritic cell is preferably contacted with the above-mentioned cell collection liquid for about 3 min-30 min. The contact method may be a method wherein a collection liquid is passed through an isolation device, and the isolation device is maintained for a given time under leaving or shaking, a method wherein a collection liquid is circulated through an isolation device and the like. The flow rate during circulation is preferably 0.1 ml/min-200 ml/min. A method of collecting dendritic cells after a contact for a given time may be a method of collecting dendritic cells by application of vibration, pushing the collection liquid swiftly while preventing damage on the dendritic cells (for example, flashing and the like) and the like. The means for pushing out dendritic cells may be, but not limited to, air, inert gas, saline and the like. In this case, to increase collection efficiency, cooling down to 4° C. or heating up to 37° C. may be concurrently performed. When collection of the dendritic cell is insufficient, the above-mentioned collection operation may be repeated.

<Protein Harvesting Method>

A method of harvesting protein using the isolation material or isolation device of the present invention is explained in detail in the following.

The method of harvesting protein of the present invention includes performing 1) a step for trapping a protein in an isolation material by contacting a protein-containing liquid with an isolation material containing, on at least a part of the surface, a substance having a sugar structure, 2) a step for removing untrapped proteins and substances other than proteins by washing the isolation material with a washing liquid, and 3) a step for collecting the trapped protein from the isolation material, in this order.

First, a protein-containing liquid is prepared as follows. A material containing protein is disrupted in Tris buffer (pH 7.4), centrifuged and the supernatant is collected. A 45% saturated ammonium sulfate is added thereto and sufficiently dissolved, and the mixture is left standing for 1 hr or longer, centrifuged to collect the precipitate, and dialyzed against 0.01M Tris buffer (pH 7.4). The dialysate is subjected to ion exchange chromatography to collect the object protein fraction, which is then contacted with the isolation material of the present invention, containing, on at least a part of the surface, a substance having a sugar structure.

When isolation material or its substrate has a form of petri dish, flask, plate, bag, cartridge, cassette and the like Step 1)

In step 1), proteins are trapped in an isolation material by contacting a protein-containing liquid with an isolation material containing a substance having a sugar structure in at least one part of a surface. To be specific, a target protein-containing liquid is injected into the isolation material of the present invention using a petri dish, a flask, a plate, a bag, a cartridge, a cassette and the like as a substrate, and the material is left standing or shaken for 5 min-120 min to contact the protein-containing liquid with the isolation material, whereby proteins are trapped in the isolation material. For stable trapping of the protein and reduced damage on the protein, the contact (standing or shaking) time is more preferably 15 min-90 min.

Step 2)

In step 2), the isolation material is washed with a washing liquid to remove untrapped proteins. While a method of removing the untrapped proteins is not particularly limited, for example, a method wherein a protein-containing liquid is first removed by suction with a pipette, a syringe and the like or decantation and the like, a buffered solution and the like are injected again into the isolation material to wash away the attached proteins, and finally, the supernatant is removed by the aforementioned suction or decantation and the like, and the like can be mentioned. When removal of the untrapped proteins is insufficient, the method may be repeated several times.

Step 3)

In step 3), the trapped proteins are collected from the isolation material. The trapped proteins can be collected, for example, by contacting a sugar-containing solution and the like with the isolation material after washing in the above-mentioned step 2).

While the kind of the collection liquid is not particularly limited, from the aspects of protein recovery rate, a solution containing the same kind of sugar as the sugar structure constituting a part of the isolation material, for example, a solution containing mannose, glucose, galactose, fucose or a mixture thereof is preferably used. The sugar concentration of a sugar-containing solution may be any from 0.01% (W/V) to the saturated solubility of the sugar at 37° C. From the aspects of collection efficiency, it is preferably 0.1% (W/V)-half the saturated solubility, more preferably 0.5% (W/V)-⅕ of the saturated solubility. In addition, the sugar-containing solution preferably contains a buffer such as a phosphate buffer and the like.

The protein is contacted with the above-mentioned cell collection liquid for about 3 min-30 min while leaving or shaking them. After contact for a given time, the protein can be collected by pipetting, application of vibration, pushing the collection liquid swiftly while preventing damage on the dendritic cells (for example, flashing and the like) and the like. The means for pushing may be, but not limited to, air, inert gas, saline and the like. In this case, to increase collection efficiency, cooling down to 4° C. may be concurrently performed. When recovery rate of the protein is insufficient, the above-mentioned collection operation may be repeated. When isolation device comprised of a container having, in at least one part thereof, an isolation material comprised of a structure having continuous pores such as non-woven fabric, fiber, porous material, spherical carrier, filter and the like is used Use of an isolation material in the form of an isolation device is particularly explained here.

Step 1)

In step 1), proteins are trapped in an isolation material by contacting a protein-containing liquid with a device comprising the above-mentioned isolation material in at least one part of a container having a liquid inlet and/or a liquid outlet.

When the above-mentioned isolation device is used, "contacting a protein-containing liquid with an isolation device" means passing a protein-containing liquid through an isolation device. Here, passing a liquid means introducing a protein-containing liquid from a liquid inlet of an isolation device, transporting the liquid in a given direction and discharging the liquid from a liquid outlet. The means for introducing a protein-containing liquid into an isolation device may be, but not limited to, a method including use of a machine such as a syringe pump, a peristaltic pump and the like, manual liquid passage using a syringe, a free fall treatment utilizing difference in height and the like. The liquid passage rate is preferably 0.1 ml/min-100 ml/min, and the liquid may be passed through the device once, or plural times by a circulation treatment.

Step 2)

In step 2), the isolation device is washed with a washing liquid to remove untrapped proteins. When the above-mentioned isolation device is used, untrapped proteins are removed from the isolation material by passing a washing liquid through the isolation device from a liquid inlet in the same direction as protein-containing liquid flow entry direction. Specific examples of the washing liquid include, but are not limited to, buffers such as Tris buffer, phosphate buffer and the like. The means for introducing a washing liquid may be, but is not limited to, a method including use of a machine such as a syringe pump, a peristaltic pump and the like, manual liquid passage using a syringe, a free fall treatment utilizing difference in height and the like. The flow rate of liquid passage using a pump is about 0.1 ml/min-100 ml/min. While the amount of the washing liquid varies depending on the isolation material used for an isolation device and the content volume of the isolation device, washing with a volume of about 1- to 5-fold the content volume is preferable.

Step 3)

In step 3), trapped proteins are collected from an isolation device. Specifically, proteins are collected by passing a sugar-containing solution and the like through the above-mentioned isolation device. Particularly, from the aspects of protein collection efficiency, a collection liquid containing the same kind of sugar as the sugar structure constituting a part of the isolation material in the isolation device, for example, a collection liquid containing mannose, glucose, galactose, fucose or a mixture thereof is preferably used. The sugar concentration of a sugar-containing solution may be any from 0.01% (W/V) to the saturated solubility of the sugar at 37° C. From the aspects of collection efficiency, it is preferably 0.1% (W/V)-half the saturated solubility, more preferably 0.5% (W/V)-⅕ of the saturated solubility. In addition, the sugar-containing solution preferably contains a buffer such as a phosphate buffer and the like. The above-mentioned isolation device is preferably contacted with the collection liquid for about 3 min-30 min, and the contact method may be leaving method, circulation method and the like. The flow rate during circulation is preferably 0.1 ml/min-200 ml/min. In this case, to increase collection efficiency, cooling down to 4° C. may be concurrently performed. When collection of the protein is insufficient, the above-mentioned collection operation may be repeated.

The method of the present invention is particularly suitable for harvesting lectin. Lectin is a generic term of proteins that recognize a sugar chain. Lectin specifically binds to a sugar chain having a particular structure, which is present in blood cell, cell surface and the like, and coagulates blood cells and cells. Lectin harvested in the present invention can be used as a cell fractionation reagent, a clinical diagnostic reagent, a clinical therapeutic drug and the like, based on its sugar chain binding specificity, blood type specificity, anticancer effect and the like. For such uses, lectin may be collected from an isolation device by the above-mentioned method and used, or directly used as a lectin-isolation device composition.

Now, a sugar residue-modified oligosaccharide-containing polyurethane represented by the formula [1-1], a carboxyl group-modified oligosaccharide-containing polyurethane represented by the formula [1-2], an acid-modified oligosaccharide-containing polyurethane represented by the formula [2-1] and an acid-modified sugar residue-modified oligosaccharide represented by the formula [3-1] of the present invention, which are used as sugar chain-containing polymers in the method of the present invention, as well as an oligosaccharide-containing polyurethane represented by the formula [1-3] used as an intermediate in the present invention are each explained in detail hereunder.

In the above-mentioned formulas [1-1], [1-2], [1-3], [2-1] and [3-1], $R^1$ is a divalent $C_{1-16}$ hydrocarbon group optionally having substituent(s).

Examples of the "divalent $C_{1-16}$ hydrocarbon group" of the above-mentioned "divalent $C_{1-16}$ hydrocarbon group optionally having substituent(s)" include (1) a straight chain or branched chain divalent $C_{1-16}$ aliphatic hydrocarbon group [e.g., a straight chain or branched chain $C_{1-16}$ alkylene group (e.g., methylene, ethylene, tetramethylene, pentamethylene, hexamethylene, octamethylene, hexadecamethylene etc.), a straight chain or branched chain $C_{2-16}$ alkenylene group (e.g., vinylene, propenylene etc.), $C_{3-16}$ cycloalkylene (e.g., cyclohexylene) and the like], (2) a divalent $C_{6-14}$ aromatic hydrocarbon group [e.g., a $C_{6-14}$ arylene group (e.g., phenylene, naphthylene, biphenylene etc.) and the like], (3) a hydrocarbon group having 7 to 16 carbon atoms, which contains at least one group selected from the aforementioned straight chain or branched chain divalent $C_{1-16}$ aliphatic hydrocarbon group and at least one group selected from the divalent $C_{6-14}$ aromatic hydrocarbon group (e.g., a group represented by the formula

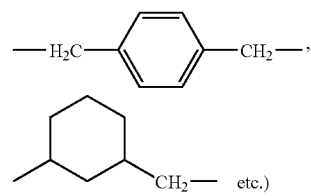

and the like.

Examples of the "substituent" of the above-mentioned "divalent $C_{1-16}$ hydrocarbon group optionally having substituent(s)" include (1) a $C_{1-6}$ alkyl group (e.g., methyl etc.);

(2) a $C_{3-8}$ cycloalkyl group (e.g., cyclohexyl etc.);

(3) a $C_{6-14}$ aryl group (e.g., phenyl etc.); and the like. The same or different, 1 to 8, preferably 1 to 4, of these substituents may be present at substitutable position(s) of the above-mentioned "divalent $C_{1-6}$ hydrocarbon group".

Specific examples of $R^1$ include a tetramethylene group, a pentamethylene group, a hexamethylene group, an octamethylene group, a hexadecamethylene group, a vinylene group, a propenylene group, a phenylene group, a naphthylene group, a phenylmethylene group, a phenylethylene group, a biphenyl group, a bisphenylmethylene group, a bisphenylethylene group, a phenylene group (e.g., paraphenylene group), a xylylene group, a tetramethylxylylene group, a tolylene group, dicyclohexylmethylene group,
a group represented by the formula

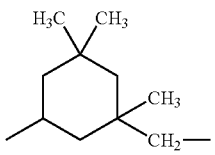

and the like, and a bisphenylmethylene group, a phenylmethylene group and a hexamethylene group are preferable.

In the formulas [1-1], [1-2], [1-3], [2-1] and [3-1], $R^2$ is a divalent group containing the same or different 1 to 100 units in total selected from a $C_{2-12}$ oxyalkylene unit and a divalent $C_{2-12}$ hydrocarbon unit optionally having substituent(s).

Examples thereof include a divalent group containing the same or different 1 to 100 units in total selected from $C_{2-12}$ oxyalkylene, a divalent group containing the same or different 1 to 100 units in total selected from divalent $C_{2-12}$ hydrocarbon unit optionally having substituent(s), and a divalent group containing the same or different 1 to 100 units in total selected from a $C_{2-12}$ oxyalkylene unit and a divalent $C_{2-12}$ hydrocarbon unit optionally having substituent(s).

The above-mentioned "divalent group containing the same or different 1 to 100 units in total selected from a $C_{2-12}$ oxyalkylene unit and a divalent $C_{2-12}$ hydrocarbon unit optionally having substituent(s)" is, for example, a divalent group containing the same or different 1 to 100 units in total selected from a unit represented by the formula $—(BO)_{h-1}—B—$ and a unit represented by the formula $-(E)_i-$, wherein B is at least one kind of $C_{2-12}$ alkylene unit, E is at least one kind of the same or different unit selected from a divalent $C_{2-12}$ hydrocarbon unit optionally having substituent(s), and h and i are each an integer of $1 \leq h \leq 100$ and $1 \leq i \leq 100$, respectively.

In the above-mentioned unit represented by the formula $—(BO)_{h-1}—B—$, the "$C_{2-12}$ alkylene group" for B may be a straight chain or branched, and when a plurality of B are present in the unit ($2 \leq h \leq 100$), B may be one kind or two or more kinds. Specific examples of, BO include an alkyleneoxy group such as an ethyleneoxy group, a propyleneoxy group, a trimethylenoxy group, a butyleneoxy group, a tetramethyleneoxy group and the like, and specific examples of the unit represented by the formula $—(BO)_{h-1}—B—$ include a unit represented by the formula $CH_2—CH_2—O—CH_2—CH_2—CH_2—$ and the like.

In the above-mentioned unit represented by the formula $-(E)_i-$, the divalent hydrocarbon unit of the "divalent $C_{2-12}$ hydrocarbon unit optionally having substituent(s)" for E may be a straight chain or branched, and a saturated group or an unsaturated group and, for example, $C_{2-12}$ alkylene (e.g., ethylene, trimethylene, tetramethylene, hexamethylene, nonamethylene etc.), $C_{2-12}$ alkenylene (e.g., butadienylene, butenylene etc.) and the like can be mentioned. Examples of the "substituent" that the "divalent $C_{2-12}$ hydrocarbon unit" optionally has include a halogen atom (e.g., fluorine atom etc.), a $C_{1-6}$ alkyl group (e.g., methyl etc.) and the like. When a plurality of E are present in the unit ($2 \leq i \leq 100$), E may be one kind or two or more kinds.

Specific examples of such unit represented by the formula $-(E)_i-$ include an ethylene group, a trimethylen group, a tetramethylene group, a hexamethylene group, a nonamethylene group, a $—CH_2—CF_2—CF_2—CF_2—CF_2—CH_2—$ group, a butadienylene group, a hydrogenated butadienylene group, a divalent group such as a group derived by eliminating one hydrogen atom from each of the carbon atoms on both chain ends of hydrogenated isoprene and the like, and the like.

In addition, $R^2$ may further contain, in addition to the unit selected from a unit represented by the above-mentioned formula $—(BO)_{h-1}—B—$ wherein B and h are as defined above and/or a unit represented by the formula $-(E)_i-$ wherein E and i are as defined above, other repeat unit [for example, repeat unit such as alkylene ester groups (e.g., ethyleneadipate group, propyleneadipate group, butyleneadipate group, hexamethyleneadipate group, neopentyladipate group and the like), alkylenecarbonate groups (e.g., hexamethylenecarbonate group and the like), a ring-opening caprolactone group, a poly(dimethylsiloxy)dimethylsilyl group and the like].

Specific examples of $R^2$ containing such unit include a divalent group derived by eliminating OH from both ends of polyethylene adipatediol and the like, a poly(dimethylsiloxy) dimethylsilyl-n-propylbisethoxy group and the like.

As specific examples of $R^2$, a divalent group having a repeat unit such as an ethyleneoxy group, a propyleneoxy group, an ethyleneadipate group, a propyleneadipate group, a hexamethylenecarbonate group, a ring-opening caprolactone group and the like, a trimethylen group, a tetramethylene group, a $—CH_2—CF_2—CF_2—CF_2—CF_2—CH_2—$ group, a hydrogenated butadienylene group, a divalent group derived by eliminating one hydrogen atom from each of the carbon atoms on both chain ends of hydrogenated isoprene, a polydimethyl siloxy dimethylsilyl-n-propylbisethoxy group and the like are preferable.

In the formulas [1-1], [1-2], [1-4] and [3-1], $R^3$ is a $C_{2-4}$ alkylene group.

Specific examples include an ethylene group, a trimethylen group, a tetramethylene group and the like. Of these, an ethylene group and a trimethylen group are preferable, and an ethylene group is more preferable.

In the formulas [1-1], [1-5] and [3-1], $R^4$ is a monosaccharide- or disaccharide-derived sugar residue. The sugar residue is a residue obtained by removing a certain hydroxyl group from sugar. Examples of the monosaccharide and disaccharide usable for $R^4$ include glucose, mannose, galactose, lactose and the like.

Of these, preferred as $R^4$ is a sugar residue derived from glucose, mannose or galactose, and a sugar residue derived from glucose is more preferable.

In the formulas [1-1], [1-2], [1-3], [2-1] and [3-1], OLS is the skeleton of oligosaccharide. The skeleton of oligosaccharide is a residue obtained by removing all hydroxyl group moieties from oligosaccharide. The oligosaccharide to be used in the present invention is not particularly limited as long as it is an oligosaccharide having two primary hydroxyl groups, which may be any of disaccharide, trisaccharide and tetrasaccharide. Specific examples include disaccharides such as trehalose, maltose, lactose, cellobiose and the like, cyclic tetrasaccharides such as cyclo{→6)-α-D-glucopyranosyl-(1→3)-α-D-glucopyranosyl-(1→6)-α-D-glucopyranosyl-(1→3)-α-D-glucopyranosyl-(1→} etc., and the like. Of these, disaccharides such as trehalose, maltose, lactose and the like are preferable from the aspects of cost and reactivity.

In the formulas [1-1], [1-2], [1-3], [2-1] and [3-1], r shows the total number of secondary hydroxyl groups of oligosaccharide. For example, when OLS is disaccharide, trisaccharide or tetrasaccharide, r is 6, 9 or 12, respectively, and when OLS is cyclic tetrasaccharide, r is 10.

In the formula [1-1], p shows the number of the secondary hydroxyl groups modified with diacid and amino sugar (group represented by the formula $—O_2C—R^3—CO—NH—R^4$; $R^3$ and $R^4$ are as defined above) of oligosaccharide, which is an integer within the range of $1 \leq p \leq r$.

In the formula [1-1], q shows the number of the secondary hydroxyl groups modified with diacid (group represented by the formula $HO_2C—R^3—CO_2—$; $R^3$ is as defined above) of oligosaccharide, which is an integer within the range of $0 \leq q \leq r-1$.

In the formula [1-2], p+q shows the number of the secondary hydroxyl groups modified with diacid (group represented by the formula $HO_2C—R^3—CO_2—$; $R^3$ is as defined above) of oligosaccharide, which is each an integer within the range of $1 \leq p \leq r$, $0 \leq q \leq r-1$.

In the formulas [1-1], [1-2], [1-3], [2-1] and [3-1], m and n are numbers of repeat units, m is an integer of 0-1000 and n is an integer of 1-1000, n/(m+n) is a number within the range of 0.01-1.00, preferably within the range of 0.02-0.80 from the aspects of the balance of water absorbability, polymer strength and polymer formability. The arrangement of repeat units in the formulas [1-1], [1-2], [1-3], [2-1] and [3-1] can be either of regular and irregular.

In the formula [2-1], s shows the number of the secondary hydroxyl groups of an oligosaccharide modified with an acid-containing group, which is an integer within the range of $1 \leq s \leq r$. Here, the "acid-containing group" is a group represented by the formula XM in the formula [2-1] wherein X and M are as defined above.

While the acid-derived moiety for the above-mentioned X may be of any kind as long as polyurethane represented by the formula [2-1] has desired properties, $SO_3$ or $PO_3$ is preferable and $SO_3$ is more preferable.

Examples of the alkali metal atom for the above-mentioned M include a sodium atom, a potassium atom, a lithium atom and the like, with preference given to a sodium atom and a potassium atom.

Examples of the organic amino group for the above-mentioned M include an amino group 1 to 3 $C_{1-6}$ alkyl groups [for example, mono-$C_{1-6}$ alkylamino group (e.g., monomethylamino group, monoethylamino group, monopropylamino group, monobutylamino group, monopentylamino group, monohexylamino group), a di-$C_{1-6}$ alkylamino group [for example, dimethylamino group, diethylamino group, dipropylamino group (e.g., di-n-propylamino group, di-iso-propylamino group), dibutylamino group], tri-$C_{1-6}$ alkylamino group (e.g., trimethylamino group, triethylamino group)], a $C_{6-14}$ aromatic amino group [for example, a $C_{6-14}$ aralkylamino group (e.g., benzylamino group), a $C_{6-14}$ aromatic heterocyclic amino group (e.g., pyridyl group)] and the like, and preferred are a dimethylamino group, a trimethylamino group, a triethylamino group, a pyridyl group and a benzylamino group.

In the formula [3-1], p shows the number of the secondary hydroxyl groups modified with an acid-containing group (group represented by the formula $—O_2C—R^3—CO—NH—R^4—(XM)_s$; $R^3$, $R^4$, X, M and s are as defined above) of oligosaccharide modified with diacid and amino sugar. Here, the "acid-containing group" is a group represented by the formula XMa in the formula [3-1] wherein X and M are as defined above.

While the acid-derived moiety for the above-mentioned X may be of any kind as long as polyurethane represented by the formula [3-1] has desired properties, $SO_3$ or $PO_3$ is preferable and $SO_3$ is more preferable.

Examples of the alkali metal atom for the above-mentioned M include a sodium atom, a potassium atom, a lithium atom and the like, with preference given to a sodium atom and a potassium atom.

Examples of the organic amino group for the above-mentioned M include an amino group having 1 to 3 $C_{1-6}$ alkyl groups [for example, mono-$C_{1-6}$ alkylamino group (e.g., monomethylamino group, monoethylamino group, monopropylamino group, monobutylamino group, monopentylamino group, monohexylamino group), di-$C_{1-6}$ alkylamino group [for example, dimethylamino group, diethylamino group, dipropylamino group (e.g., di-n-propylamino group, di-iso-propylamino group), dibutylamino group], tri-$C_{1-6}$ alkylamino group (e.g., trimethylamino group, triethylamino group)], a $C_{6-14}$ aromatic amino group [for example, $C_{6-14}$ aralkylamino group (e.g., benzylamino group), $C_{6-14}$ aromatic heterocycleamino group (e.g., pyridyl group)] and the like, and preferred are a dimethylamino group, a trimethylamino group, a triethylamino group, a pyridyl group and a benzylamino group.

The production methods of the sugar residue-modified oligosaccharide-containing polyurethane represented by the formula [1-1], the carboxyl group-modified oligosaccharide-containing polyurethane represented by the formula [1-2], and the oligosaccharide-containing polyurethane (intermediate) represented by the formula [1-3] in the present invention are each explained below.

<Production Method of Oligosaccharide-Containing Polyurethane (Intermediate) Represented by the Formula [1-3]>

In the present invention, the oligosaccharide-containing polyurethane represented by the formula [1-3] can be obtained by reacting an oligosaccharide represented by the formula [1-6]:

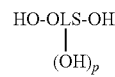

[1-6]

wherein OLS and p are as defined above and, where necessary, a diol represented by the following formula [1-7]:

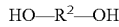

[1-7]

wherein $R^2$ is as defined above, with a diisocyanate represented by the following formula [1-8]:

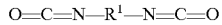

[1-8]

wherein $R^1$ is as defined above.

In this case, the oligosaccharide represented by the formula [1-6] may be mixed, where necessary, with the diol represented by the formula [1-7] and the mixture is reacted with the diisocyanate represented by the formula [1-8] (one-shot method), or the diisocyanate represented by the formula [1-8] may be reacted, where necessary, with the diol represented by the formula [1-7] to give a prepolymer, which is then reacted with the oligosaccharide represented by the formula [1-6] (Prepolymer Method 1), or the oligosaccharide represented by the formula [1-6] may be reacted with the diisocyanate represented by the formula [1-8] to give a prepolymer, which is then reacted, where necessary, with the diol represented by the formula [1-7] (Prepolymer Method 2).

In the above-mentioned reactions, the oligosaccharide represented by the formula [1-6], the diisocyanate represented by the formula [1-8] and the diol represented by the formula [1-7] each may be one kind or a mixture of two or more kinds.

Examples of the diisocyanate of the aforementioned formula [1-8] to be used in the present invention include tetramethylenediisocyanate, pentamethylenediisocyanate, hexamethylenediisocyanate, octamethylenediisocyanate, hexadecamethylenediisocyanate, vinylenediisocyanate, propenylenediisocyanate, naphthylenediisocyanate, phenylmethanediisocyanate, diphenylmethanediisocyanate, phenylethanediisocyanate, diphenylethanediisocyanate, phenylenediisocyanate (e.g., paraphenylenediisocyanate), biphenyldiisocyanate, xylylenediisocyanate, tetramethylxylylenediisocyanate, tolylenediisocyanate, isophoronediisocyanate, dicyclohexylmethanediisocyanate and the like.

The diol represented by the formula [1-7] is not particularly limited as long as it has a primary hydroxyl group. Specific examples include low molecular weight diols such as ethylene glycol, 1,3-propanediol, 1,4-butanediol, 1,6-hexanediol, 1,9-nonanediol, 2,2,3,3,4,4,5,5-octafluoro-1,6-hexanediol and the like; high molecular weight diols, for example, polyether diols such as polyethylene glycol, polytetramethylene ether glycol, polypropylene glycol, ethyleneoxide-propyleneoxide copolymer, tetrahydrofuran-ethylene oxide copolymer, tetrahydrofuran-propylene oxide copolymer and the like, polyester diols such as polyethylene adipate glycol, polydiethylene adipate glycol, polypropylene adipate glycol, polybutylene adipate glycol, polyhexamethylene adipate glycol, polyneopentyladipate glycol, polycaprolactone glycol and the like, polycarbonate diols such as polyhexamethylenecarbonate glycol and the like, polyolefin glycols such as polybutadiene glycol, hydrogenated polybutadiene glycol, hydrogenated polyisoprene glycol and the like, silicone diols such as bis(hydroxyethoxy-n-propyldimethylsilyl)polydimethyl siloxane and the like, and the like; and the like.

The solvent used for producing the oligosaccharide-containing polyurethane represented by the above-mentioned formula [1-3] may be any as long as it can dissolve the reaction product and the resulting polyurethane. Specific examples include organic solvents such as dimethyl sulfoxide (DMSO), N-methyl-2-pyrrolidone (NMP), N,N-dimethylformamide (DMF), N,N-dimethylacetamide (DMAc) and the like, alone or a mixed solvent thereof.

For production of the oligosaccharide-containing polyurethane represented by the above-mentioned formula [1-3], for example, the oligosaccharide represented by the aforementioned formula [1-6] and, where necessary, the diol represented by the formula [1-7] are added to a solution containing the diisocyanate represented by the formula [1-8] while passing a dry inert gas such as nitrogen and the like.

The molar ratio of the above-mentioned reaction components charged is, for example, compound represented by the formula [1-8]: compound represented by the formula [1-7]: compound represented by the formula [1-6] preferably 3:0.01-2.99:0.01-3, more preferably 3:0.2-2.5:0.5-2.8.

The reaction temperature of the above-mentioned reaction is preferably 10-150° C., more preferably 20-120° C., and the reaction time is preferably 1-10 hr, more preferably 2-6 hr.

After completion of the reaction, the oligosaccharide-containing polyurethane represented by the formula [1-3]

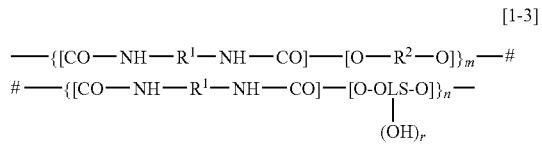

wherein $R^1$, $R^2$, OLS, m, n and r are as defined above, can be obtained. The polyurethane can be purified by, for example, feeding the reaction solution into a single or mixed solvent of methanol, acetone, water and the like, filtration, washing and, where necessary, repeating reprecipitation purification to give a solid content, which is dried under reduced pressure at room temperature −100° C. for about 1-24 hr.

<Production Method of Carboxyl Group-Modified Oligosaccharide-Containing Polyurethane Represented by the Formula [1-2]>

The production method of the carboxyl group-modified oligosaccharide-containing polyurethane represented by the formula [1-2] is explained below.

A carboxyl group-modified oligosaccharide-containing polyurethane represented by the formula [1-2]

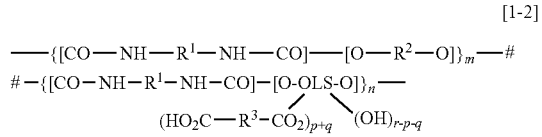

wherein $R^1$, $R^2$, $R^3$, OLS, m, n, p, q and r are as defined above, can be produced by reacting the oligosaccharide-containing polyurethane represented by the above-mentioned formula [1-3] with an acid anhydride represented by the formula [1-4]

wherein $R^3$ is are as defined above, and entirely or partially modifying the secondary hydroxyl group of oligosaccharide.

The above-mentioned reaction is generally performed in a solvent. The solvent for carboxyl group modification may be any as long as it can dissolve the reaction product and the resulting polyurethane. Specific examples include organic solvents such as dimethyl sulfoxide (DMSO), N-methyl-2-pyrrolidone (NMP), N,N-dimethylformamide (DMF), N,N-dimethylacetamide (DMAc) and the like, alone or a mixed solvent thereof.

As the acid anhydride represented by the above-mentioned formula [1-4], a dibasic anhydride such as succinic anhydride, glutaric anhydride, adipic anhydride and the like is preferably used, and succinic anhydride is most preferable. The acid anhydride may be used alone or as a mixture of two or more kinds. The amount thereof to be used when a hydroxyl group of straight chain oligosaccharide in polyurethane is to be partially modified is 1- to (r−1)-fold mol relative to the number of secondary hydroxyl groups (r) of oligosaccharide in polyurethane, and the amount when the aforementioned hydroxyl group is to be completely modified is r- to 2r-fold mol, preferably 1.2r- to 1.5r-fold mol.

In the above-mentioned reaction, where necessary, 4-dimethylaminopyridine or imidazole is preferably used in a proportion of 3-10 mol %, more preferably 5 mol %, as a catalyst.

The reaction temperature of the above-mentioned reaction is 20-100° C., preferably 50-90° C., and the reaction time is 1-24 hr, preferably 2-20 hr.

After completion of the reaction, a carboxyl group-modified oligosaccharide-containing polyurethane represented by the formula [1-2] of the present invention can be obtained. The polyurethane can be purified by, for example, feeding the reaction solution into a single or mixed solvent of methanol, acetone, water and the like to allow precipitation of a polymer, filtering, washing and, where necessary, repeating reprecipitation purification to give a solid content, which can be dried under reduced pressure at room temperature –100° C. for about 1-24 hr.

<Production Method of Sugar Residue-Modified Oligosaccharide-Containing Polyurethane Represented by the formula [1-1]>

A sugar residue-modified oligosaccharide-containing polyurethane represented by the formula [1-1]

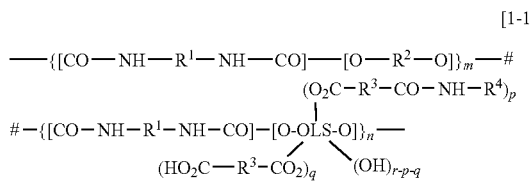

wherein $R^1$, $R^2$, $R^3$, $R^4$, p, q, r, m, n and OLS are each as defined above, can be obtained by reacting a carboxyl group-modified oligosaccharide-containing polyurethane represented by the above-mentioned formula [1-2] with an aminated sugar represented by the following formula [1-5]:

wherein $R^4$ is as defined above.

As the aminated sugar represented by the formula [1-5], for example, glucose amine, mannose amine, lactose amine, galactose amine and the like are preferable. Of these, glucose amine and mannose amine are more preferable, and glucose amine is most preferable from the aspects of cost. In addition, the aminated sugar may be used alone or as a mixture of two or more kinds. The amount thereof to be used is adjusted according to the object number of aminated sugar modifications relative to the number of carboxyl groups (p+q) in polyurethane represented by [1-2]. When the number of the aminated sugar modifications is 1 or 2, the amount is 1- or 2-fold mol relative to the number of carboxyl groups (p+q), and when the number of aminated sugar modifications is not less than 3, the amount is 3-fold or more relative to the number of carboxyl groups (p+q).

The above-mentioned reaction is generally performed in a solvent. The solvent may be any as long as it can dissolve the reaction product and the resulting polyurethane. Specific examples include organic solvents such as dimethyl sulfoxide (DMSO), N-methyl-2-pyrrolidone (NMP), N,N-dimethylformamide (DMF), N,N-dimethylacetamide (DMAc) and the like, alone or a mixed solvent thereof, and further, a mixed solvent thereof with methanol, ethanol, water.

The above-mentioned reaction is preferably performed in the presence of a condensation agent. As the condensation agent, 1-ethyl-3-(3-dimethylaminopropyl)carbodiimide (EDC)/N-hydroxysuccinimide (NHS) mixture, dicyclohexylcarbodiimide (DCC), 4(4,6-dimethoxy-1,3,5-triazin-2-yl)-4-methylmorpholinium chloride (DMT-MM) and the like are used. An EDC/NHS mixture and DMT-MM are most preferable. The amount thereof to be used is 0.5- to 1.5-fold mol, preferably 0.8- to 1.2-fold mol, relative to the aminated sugar.

The reaction temperature of the above-mentioned reaction is 20-60° C., preferably 30-50° C., and the reaction time is 5-36 hr, preferably 10-20 hr.

After completion of the reaction, a sugar residue-modified oligosaccharide-containing polyurethane represented by the formula [1-1] of the present invention can be obtained. The polyurethane can be purified by, for example, evaporating the reaction solvent, feeding a single or mixed solvent of methanol, water and the like to the concentrate to wash the polymer, filtering, and, where necessary, repeating reprecipitation purification to give a solid content, which can be dried under reduced pressure at room temperature –100° C. for about 1-24 hr.

Since the sugar residue-modified oligosaccharide-containing polyurethane represented by the above-mentioned formula [1-1] and the carboxyl group-modified oligosaccharide-containing polyurethane represented by the formula [1-2] of the present invention have the above-mentioned structure, the density of the sugar aggregate formed by a substance having a sugar structure, which is introduced into the polymer chain, increases. Therefore, they have superior physiological functions (e.g., function of trapping monocyte, lymphocyte, granulocyte, stem cell, virus, protein and the like, and the like) for various components derived from living organisms, and can be used as various physiological materials. The physiological material here is, for example, a composition containing a polyurethane represented by the above-mentioned formula [1-1] or a polyurethane represented by the formula [1-2] of the present invention in the form of a solution, a suspension, a paste, a polymer blend and the like appropriate for use as a substrate of the isolation material. Examples thereof include, but are not limited to, a solution or suspension wherein polyurethane is dissolved or suspended in an organic solvent (DMSO, NMP, DMF, DMAc and the like, alone or a mixed solvent thereof, water etc.), polymer blend of polyurethane and any polymer inactive to the polyurethane and the like.

The physiological material of the present invention can be used for various applications such as for contact with a body fluid such as blood and the like, an isolation material to harvest monocyte, lymphocyte, granulocyte, stem cell, virus, protein (lectin and the like) and the like from a body fluid, an isolation device and an isolation filter (e.g., blood isolation filter, monocyte isolation filter, lymphocyte isolation filter, granulocyte isolation filter, stem cell isolation filter, virus isolation filter, protein isolation filter (e.g., lectin isolation filter and the like) and the like) using the material, and the like.

<Production Method of Acid-Modified Oligosaccharide-Containing Polyurethane Represented by the Formula [2-1]>

The acid-modified oligosaccharide-containing polyurethane of the present invention represented by the formula [2-1]

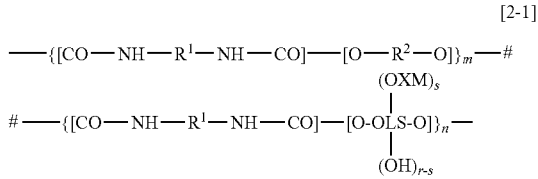

wherein each symbol is as defined above, can be obtained by reacting the oligosaccharide-containing polyurethane represented by the above-mentioned formula [1-3] with an acid modifying reagent.

As the acid modifying reagent, for example, when X is $SO_3$, trimethylaminesulfur trioxide complex, triethylaminesulfur trioxide complex, dimethylformamidesulfur trioxide complex, pyridinesulfur trioxide complex, chlorosulfonate and the like are used, and when X is $PO_3$, orthophosphoric acid, polyphosphoric acid, diphosphorus pentoxide, phosphorus oxychloride and the like are used.

The above-mentioned reaction is generally performed in a solvent. As the solvent, dimethylformamide, pyridine, dimethyl sulfoxide (DMSO) and the like are generally used. The reaction temperature is generally 0° C.-80° C., and the reaction time is generally 5 min-24 hr. Where necessary, the obtained compound is treated with an ion exchange resin ($Na^+$ type and the like) to convert M to an alkali metal atom (e.g., sodium atom and the like) and the like.

Since the sulfated oligosaccharide-containing polyurethane represented by the above-mentioned formula [2-1] of the present invention have the above-mentioned structure, the density of the sugar aggregate formed by a substance having a sugar structure, which is introduced into the polymer chain, increases. Therefore, they have superior physiological functions (e.g., function of trapping virus, protein and the like, and the like) for various components derived from living organisms, and can be used as various physiological materials. The physiological material here is, for example, a composition containing a sulfated oligosaccharide-containing polyurethane represented by the above-mentioned formula [2-1] of the present invention in the form of a solution, a suspension, a paste, a polymer blend and the like appropriate for use as a substrate of the isolation material. Examples thereof include, but are not limited to, a solution or suspension wherein polyurethane is dissolved or suspended in an organic solvent (DMSO, NMP, DMF, DMAc and the like, alone or a mixed solvent thereof, water etc.), polymer blend of polyurethane and any polymer inactive to the polyurethane and the like.

The physiological material of the present invention can be used for applications such as for contact with blood and the like, an isolation material to harvest monocyte, lymphocyte, granulocyte, stem cell, virus, protein (lectin and the like) and the like from a body fluid, an isolation device and an isolation filter (e.g., blood isolation filter, monocyte isolation filter, lymphocyte isolation filter, granulocyte isolation filter, stem cell isolation filter, virus isolation filter, protein isolation filter (e.g., lectin isolation filter and the like) and the like) using the material, and the like.

<Production Method of Acid-Modified Sugar Residue-Modified Oligosaccharide-Containing Polyurethane Represented by the Formula [3-1]>

An acid-modified sugar residue-modified oligosaccharide-containing polyurethane represented by the formula [3-1] of the present invention

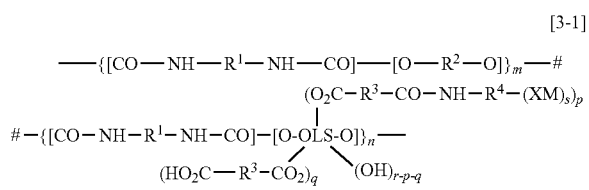

[3-1]

wherein each symbol is as defined above, can be obtained by reacting the sugar residue-modified oligosaccharide-containing polyurethane represented by the above-mentioned formula [1-1] with an acid modifying reagent.

As the acid modifying reagent, for example, when X is $SO_3$, trimethylaminesulfur trioxide complex, triethylaminesulfur trioxide complex, dimethylformamidesulfur trioxide complex, pyridinesulfur trioxide complex, chlorosulfonic acid and the like are used, and when X is $PO_3$, orthophosphoric acid, polyphosphoric acid, diphosphorus pentoxide, phosphorus oxychloride and the like are used.

The above-mentioned reaction is generally performed in a solvent. As the solvent, dimethylformamide, pyridine, dimethyl sulfoxide (DMSO) and the like are generally used. The reaction temperature is generally 0° C.-80° C., and the reaction time is generally 5 min-24 hr. Where necessary, the obtained compound is treated with an ion exchange resin ($Na^+$ type and the like) to convert M to an alkali metal atom (e.g., sodium atom and the like) and the like.

Since the acid-modified sugar residue-modified oligosaccharide-containing polyurethane represented by the above-mentioned formula [3-1] of the present invention have the above-mentioned structure, the density of the sugar aggregate formed by a substance having a sugar structure, which is introduced into the polymer chain, increases. Therefore, they have superior physiological functions (e.g., function of trapping virus, protein and the like, and the like) for various components derived from living organisms, and can be used as various physiological materials. The physiological material here is, for example, a composition containing an acid-modified sugar residue-modified oligosaccharide-containing polyurethane represented by the above-mentioned formula [3-1] of the present invention in the form of a solution, a suspension, a paste, a polymer blend and the like appropriate for use as a substrate of the isolation material. Examples thereof include, but are not limited to, a solution or suspension wherein polyurethane is dissolved or suspended in a solvent (organic solvent such as DMSO, NMP, DMF, DMAc and the like, alone or a mixed solvent thereof, water etc.), polymer blend of polyurethane and any polymer inactive to the polyurethane and the like.

The physiological material of the present invention can be used for applications such as for contact with blood and the like, an isolation material to harvest monocyte, lymphocyte, granulocyte, stem cell, virus, protein (lectin and the like) and the like from a body fluid, an isolation device and an isolation filter (e.g., blood isolation filter, monocyte isolation filter, lymphocyte isolation filter, granulocyte isolation filter, stem cell isolation filter, virus isolation filter, protein isolation filter (e.g., lectin isolation filter and the like) and the like) using the material, and the like.

EXAMPLES

Example A

Harvesting Method of Monocyte and Preparation Method of Dendritic Cell

The present invention is explained in more detail by referring to the following Examples, which are not to be construed as limitative.

Example A1

(1) Preparation of Cell Isolation Material

A mannobiose-bound polystyrene derivative (Poly[N-p-vinylbenzyl-O-β-D-mannopyranosyl-(1→4)-D-mannamide], manufactured by SEIKAGAKU CORPORATION) was dissolved in distilled water at a concentration of 0.1% (W/V). The solution (1 ml) was added to a commercially available 1 ml polystyrene petri dish (diameter 35 mm), and left standing at room temperature for about 1 hr. Then, the supernatant polymer was removed, and saline (1 ml) was added. Excess mannobiose-bound polystyrene derivative was washed, and the supernatant was removed. This operation was repeated 3 times to give a mannobiose-bound polystyrene derivative coated petri dish.

(2) Isolation of Monocyte

A winged injection needle was punctured into an upper arm of a healthy subject, and the blood (about 7.5 ml) was drawn in a lymphocyte isolation tube (vacutainer tube, manufactured by Becton, Dickinson and Company). After blood sampling, 3.8% citric acid solution was added to the vacutainer tube such that blood:citric acid=10:1, and the vacutainer tube was immediately centrifuged at 3000 rpm for 20 min at room temperature. The plasma component was collected, and the mononuclear cell layer was separately collected in a container. Saline (40 ml) was added, and the mixture was centrifuged at 1500 rpm for 5 min at 4° C. This operation was repeated several times to wash the mononuclear cells. The washed mononuclear cells were re-suspended in the plasma collected above to give a mononuclear cell suspension having a given concentration.

Then, the prepared mononuclear cell suspension (1 ml, number of nuclear cells $2.0 \times 10^6$ cells) were added to the mannobiose-bound polystyrene derivative coating petri dish of (1), and the mixture was left standing in an incubator at 37° C., 5% $CO_2$ for 30 min. After a predetermined time, the supernatant was collected, and the petri dish was washed 3 times with saline (1 ml). Then, 10% mannose solution (1 ml) was added, and the mixture was left standing in an incubator at 37° C., 5% $CO_2$ for 15 min. The monocytes attached to the petri dish were collected by pipetting. The collection rate of the monocytes was determined by the following formula.

Monocyte collection rate (%)=(number of monocytes collected from the petri dish/number of monocytes before inoculation)×100   formula (1)

The number of monocytes was determined by measuring the number of leukocytes in the cell suspension collected from the petri dish by a blood cell counter (KX-21NV, manufactured by Sysmex Corporation), labeling the cell suspension with CD14-PE fluorescence antibody (manufactured by Japan Becton, Dickinson and Company), determining the monocyte ratio by a flow cytometer (BD FACS Canto, manufactured by Japan Becton, Dickinson and Company), and multiplying the number of leukocytes by the monocyte ratio. The number of monocytes before inoculation was also determined by performing a similar operation for a cell suspension before inoculation as a target.

The purity of the monocyte was determined by labeling the cell suspension collected from the petri dish with a CD14-PE fluorescence antibody (manufactured by Japan Becton, Dickinson and Company), and measuring by a flow cytometer (BD FACS Canto, manufactured by Japan Becton, Dickinson and Company). As a result, the monocyte recovery rate was 78% and the purity was 96%, and the monocyte was found to have been selectively isolated and collected.

Example A2

In the same manner as in Example A1 except that a lactose-bound polystyrene derivative (nonreducing terminal sugar is galactose, manufactured by SEIKAGAKU CORPORATION) was used instead of the mannobiose-bound polystyrene derivative, the recovery rate and purity of the monocyte were measured. As a result, the recovery rate of monocyte was 81% and the purity thereof was 73%, and the monocyte was found to have been selectively isolated and collected.

Example A3

In the same manner as in Example A1 except that a maltose-bind polystyrene derivative (nonreducing terminal sugar is galactose, manufactured by SEIKAGAKU CORPORATION) was used instead of the mannobiose-bound polystyrene derivative, the recovery rate and purity of the monocyte were measured. As a result, the recovery rate of monocyte was 76% and the purity thereof was 71%, and the monocyte was found to have been selectively isolated and collected.

Comparative Example A1

In the same manner as in Example A1 except that a polystyrene petri dish free of polymer coating was used, the collection rate and purity of the monocyte and the recovery rate of the dendritic cell were measured. As a result, the recovery rate of monocyte was 56% and the purity thereof was 46%.

The above results are summarized in Table A1.

TABLE A1

| | Isolation/collection of monocyte using cell isolation device | |
|---|---|---|
| | Recovery rate (%) of monocyte | Purity (%) of monocyte |
| Ex. A1 | 78 | 96 |
| Ex. A2 | 81 | 73 |
| Ex. A3 | 76 | 71 |
| Com. Ex. A1 | 56 | 46 |

Example A4

Preparation of Dendritic Cell:

A mononuclear cell suspension (1 ml, the number of nuclear cells $2.0 \times 10^6$ cells) prepared according to the method of Example A1(1) was added to a mannobiose-bound polystyrene derivative coated petri dish prepared according to the method of Example A1(1), and the mixture was left standing in an incubator at 37° C., 5% $CO_2$ for 30 min. After 30 min, the supernatant was removed, saline (1 ml) was added, the petri dish was stirred slowly, and the supernatant was removed. Untrapped cells were washed by repeating the washing operation 5 times. Then AIM-V (manufactured by GIBCO) medium (1.5 ml) prepared to IL-4: 500 IU/ml, GM-CSF: 500 IU/ml was added, and the cells were cultured for 6 days.

Collection of Dendritic Cell:

After culture for 6 days, the cells floating in the petri dish supernatant were collected, 10% mannose solution (1 ml) was further added to the petri dish, and the mixture was left standing in an incubator at 37° C., 5% $CO_2$ for 15 min. After 15 min, the cells trapped in the petri dish were collected by a pipetting operation, combined with the cells collected earlier, and the total number of the collected cells was determined by a blood cell counting chamber.

Identification of Dendritic Cell:

The cell suspension obtained by a dendritic cell collection operation were taken by 200 μl in a polypropylene test tube, 10 μl each of anti-CD14 antibody (PE-labeled), and anti-HLA-DR antibody (FITC-labeled, manufactured by Becton, Dickinson and Company) was added, and the mixture was left standing in a dark and cold place for 20 min. After a predetermined time, the mixture was centrifuged at 1500 rpm for 5 min, and the supernatant was removed. Then phosphate buffer (1 ml) was added, and the measurement was performed by a flow cytometer. As a result of the measurement, surface antigen CD14+ and HLA-DR+ was taken as monocyte, CD14– and HLA-DR+ was taken as dendritic cell, and the positive rate of each cell was determined.

The recovery rate of the dendritic cell was measured by the following formulas (2) and (3).

$$\text{number of dendritic cells collected from the petri dish} = \text{total number of cells collected from the petri dish} \times \text{dendritic cell positive rate} \quad \text{formula (2)}$$

$$\text{recovery rate (\%) of dendritic cell} = (\text{number of dendritic cells collected from the petri dish}/\text{number of monocytes trapped in petri dish}) \times 100 \quad \text{formula (3)}$$

As a result, the recovery rate of the dendritic cell was 47.6%.

Comparative Example A2

In the same manner as in Example A4 except that a polystyrene petri dish free of coating with a mannobiose-bound polystyrene derivative polymer was used, the recovery rate of dendritic cell was measured. As a result, the recovery rate of dendritic cell was 23.6%.

The above results are summarized in Table A2.

TABLE A2

| Recovery rate of dendritic cell using cell isolation device | |
|---|---|
| | Recovery rate (%) of dendritic cell |
| Ex. A4 | 47.6 |
| Com. Ex. A2 | 23.6 |

Example A5

1. Preparation of Mannose Amine-Immobilized Cell Isolation Material

Cellulose acetate was dissolved in a mixed solvent of dimethyl sulfoxide and propylene glycol, the solution was prepared into droplets by the method (vibration method) described in JP-A-63-117039, coagulated to give cellulose acetate spherical particles. The obtained spherical particles had a particle size of about 400 μm. The particles were mixed with 4N aqueous sodium hydroxide solution at a sedimentation volume ratio of 1:1 (V/V) to allow contact at 10° C.-15° C. for 120 min for hydrolysis. The obtained porous cellulose carrier (40 ml by sedimentation volume) was separated, 40 ml of reverse osmosis water (Yamato Pure line RO21, manufactured by Yamato Scientific Co., Ltd.) was added, and the inside temperature was raised to 40° C. 2N NaOH (24 ml) was added, and the mixture was shaken at 40° C. for 30 min. Then, epichlorohydrin (8.2 ml) was added, and the mixture was reacted at 40° C. for 2 hr. After completion of the reaction, carrier was washed with water (about 4 L) to give an epoxydized carrier (epoxy introduction amount; 32.9 μmol/g). Then, mannose amine (manufactured by Sigma Ltd., molecular weight about 215, 0.783 g) was dissolved in 0.5M sodium hydrogen carbonate buffer (51 ml) adjusted to pH 10.5. The epoxydized carrier (51 ml by sediment volume) was added, and the mixture was reacted at 37° C. for 16 hr to immobilize mannose amine. After completion of the reaction, the carrier was washed until the washing liquid was neutralized to give a mannose amine-immobilized carrier. Reverse osmosis water was added to the mannose amine-immobilized carrier (51 ml by sedimentation volume) to the total amount of 102 ml. Monoethanolamine (510 μl) was added thereto, and the mixture was reacted at 45° C. for 2 hr. After completion of the reaction, the carrier was washed until the washing liquid was neutralized. By this reaction, unreacted epoxy group was blocked.

2. Contact Conditions of Blood-Granulocyte Adsorption Column

The obtained above-mentioned mannose amine-immobilized carrier was washed with heparin (heparin sodium injection, manufactured by Mitsubishi Tanabe Pharma Corporation) added saline (prepared to the heparin final concentration of 5 IU/ml) for heparin equilibration. Then mannose amine-immobilized carrier was defoamed, and 1.0 ml by sedimentation volume was filled in a mini column (acrylic, inner diameter 10 mm, height 10 mm). A polyvinyl chloride tube (inner diameter 1 mm, outer diameter 3 mm, length 50 cm) was mounted on the column entry side, and a similar polyvinyl chloride tube (length 20 cm) was mounted on the column exit side.

The mononuclear cell suspension (5 ml, total number of nuclear cells $6.0 \times 10^5$ cells) prepared according to the method described in Example A1(1) was passed through the mini column at a flow rate of 0.2 ml/min. The time point when the mononuclear cell suspension was discharged from the column exit side was taken as the start point, and the tip of the tube on the column exit side was returned to the cell pool container and the perfusion was performed for 60 min.

[Measurement of Number of Blood Cells]

After a predetermined time, the cell suspension on the column exit side was harvested, the number of leukocytes was measured by a blood cell counting apparatus (KX-21NV manufactured by SYSMEX CORPORATION), and the monocyte ratio was determined by a flow cytometer (FACS-Canto, Becton, Dickinson and Company). The results are shown in Table 3.

As a result, the number of lymphocyte did not change. However, since the number of monocytes drastically decreased after the column treatment, it was found that the monocytes were selectively trapped by the cell isolation material in the column. The results are shown in Table A3.

TABLE 3

Table A3: Changes of numbers of various cells before and after treatment with cell isolation material packed column (treatment time 60 min)

| | number of nuclear cells ($\times 10\uparrow 5$ cells) | positive rate (%) | | number of cells ($\times 10\uparrow 5$ cells) | |
|---|---|---|---|---|---|
| | | monocyte | lymphocyte | monocyte | lymphocyte |
| before treatment | 30 | 27.0 | 70.8 | 8.0 | 21 |

TABLE 3-continued

Table A3: Changes of numbers of various cells before and after treatment with cell isolation material packed column (treatment time 60 min)

| | number of nuclear cells ($\times 10^5$ cells) | positive rate (%) | | number of cells ($\times 10^5$ cells) | |
|---|---|---|---|---|---|
| | | monocyte | lymphocyte | monocyte | lymphocyte |
| after treatment | 25 | 10.8 | 88.0 | 2.5 | 22 |

Example B

Production of Sugar Residue-Modified Oligosaccharide-Containing Polyurethane and Carboxyl Group-Modified Oligosaccharide-Containing Polyurethane, and Evaluation of Physiological Activities Thereof Now the production methods of a sugar residue-modified oligosaccharide-containing polyurethane and a carboxyl group-modified oligosaccharide-containing polyurethane of the present invention are explained in detail based on the Examples, which are not to be construed as limitative.

The monomer compounds to be used for polymerization are abbreviated as follows.

OLS=oligosaccharide skeleton
TRE=trehalose
CTS=cyclic tetrasaccharide: cyclo{→6)-α-D-glucopyranosyl-(1→3)-α-D-glucopyranosyl-(1→6)-α-D-glucopyranosyl-(1→3)-α-D-glucopyranosyl-(1→)
MDI=methanediphenyldiisocyanate
PPG4=polypropylene glycol (molecular weight 400)
PPG7=polypropylene glycol (molecular weight 700)
SUC=succinic anhydride
GluA=glucose amine
2-ManA=mannose amine

Synthetic Example B1

Synthesis of MDI-PPG4-TRE (Molar Ratio 2/1/1) Polyurethane (Prepolymer Method 1)

Methane diphenyl diisocyanate (5.85 g) and dimethylacetamide (65 ml) were added to a 4-mouth flask (purged with nitrogen gas) equipped with a mechanical stirrer. Polypropylene glycol (average molecular weight 400, 4.68 g) was added at room temperature with stirring, and the mixture was reacted for 1 hr. Then, trehalose (4.00 g) was added to the reaction mixture, and the mixture was reacted at said temperature for 4 hr. The reaction solution was concentrated and poured into water (500 ml) to allow precipitation of a product, which was collected by filtration, washed with water and vacuum dried to give a product (yield 81%).

The product was confirmed to be the object product by proton NMR.
proton NMR proton (solvent: dimethyl sulfoxide)
1.05, 1.20; $CH_3$—
3.20-3.80; —O—CH—$CH_2$—O—, —$CH_2$—, —CH—
3.86; —$CH_2$—
4.30-5.00; —O—CH—O—, —OH
7.16, 7.43; —$C_6H_4$—
8.65, 9.60; —NH—CO—

Synthetic Example B2

Synthesis of MDI-PPG7-TRE (Molar Ratio 2/1/1) Polyurethane (Prepolymer Method 1)

Methane diphenyl diisocyanate (4.39 g) and dimethylacetamide (65 ml) were added to a 4-mouth flask (purged with nitrogen gas) equipped with a mechanical stirrer. Polypropylene glycol (average molecular weight 700, 6.14 g) was added at room temperature with stirring, and the mixture was reacted for 1 hr. Then, trehalose (3.00 g) was added to the reaction mixture, and the mixture was reacted at said temperature for 4 hr. The reaction solution was concentrated and poured into water (500 ml) to allow precipitation of a product, which was collected by filtration, washed with water and vacuum dried to give a product (yield 87%).

The product was confirmed to be the object product by proton NMR.
proton NMR proton (solvent: dimethyl sulfoxide)
1.05, 1.20; $CH_3$—
3.20-3.80; —O—CH—$CH_2$—O—, —$CH_2$—, —CH—
3.86; —$CH_2$—
4.30-5.00; —O—CH—O—, —OH
7.16, 7.43; —$C_6H_4$—
8.65, 9.60; —NH—CO—

Synthetic Example B3

Synthesis of MDI-PPG4-CTS (Molar Ratio 2/1/1) Polyurethane (Prepolymer Method 1)

Methane diphenyl diisocyanate (11.59 g) and dimethylacetamide (150 ml) were added to a 4-mouth flask (purged with nitrogen gas) equipped with a mechanical stirrer. Polypropylene glycol (average molecular weight 400, 9.26 g) was added at room temperature with stirring, and the mixture was reacted for 1 hr. Then, cyclic tetrasaccharide (15.00 g) was added to the reaction mixture, and the mixture was reacted at said temperature for 6 hr. The reaction solution was concentrated and poured into water (1000 ml) to allow precipitation of a product, which was collected by filtration, washed with water and vacuum dried to give a product (yield 70%).

The product was confirmed to be the object product by proton NMR.
proton NMR proton (solvent: dimethyl sulfoxide)
1.05, 1.20; $CH_3$—
3.20-3.80; —O—CH—$CH_2$—O—, —$CH_2$—, —CH—
3.86; —$CH_2$—
4.30-5.00; —O—CH—O—, —OH
7.16, 7.43; —$C_6H_4$—
8.65, 9.60; —NH—CO—

Synthetic Example B4

Synthesis of MDI-PPG7-CTS (Molar Ratio 2/1/1) Polyurethane (Prepolymer Method 1)

Methane diphenyl diisocyanate (7.7 g) and dimethylacetamide (175 ml) were added to a 4-mouth flask (purged with nitrogen gas) equipped with a mechanical stirrer. Polypropylene glycol (average molecular weight 700, 10.80 g) was added at room temperature with stirring, and the mixture was reacted for 1 hr. Then, cyclic tetrasaccharide (10.00 g) was added to the reaction mixture, and the mixture was reacted at said temperature for 6 hr. The reaction solution was concentrated and poured into water (1000 ml) to allow precipitation of a product, which was collected by filtration, washed with water and vacuum dried to give a product (yield 73%).

The product was confirmed to be the object product by proton NMR.

proton NMR proton (solvent: dimethyl sulfoxide)
1.05, 1.20; $CH_3$—
3.20-3.80; —O—CH—$CH_2$—O—, —$CH_2$—, —CH—
3.86; —$CH_2$—
4.30-5.00; —O—CH—O—, —OH
7.16, 7.43; —$C_6H_4$—
8.65, 9.60; —NH—CO—

Example B1

Synthesis of MDI-PPG4-TRE (Molar Ratio 2/1/1)-3SUC Polyurethane

Polyurethane (1.00 g) in Synthetic Example B1 and dimethylformamide (25 ml) were added to a 4-mouth flask (purged with nitrogen gas) equipped with a mechanical stirrer. Succinic anhydride (0.24 g) and 4-dimethylaminopyridine (0.025 g) were added at room temperature with stirring, and the mixture was reacted at 70° C. for 5 hr. The reaction solution was concentrated and poured into water (75 ml) to allow precipitation of a product. 1M Hydrochloric acid (3 drops) was added, and the precipitate was collected by filtration, washed with water and vacuum dried to give a product (yield 95%). The product was confirmed to be the object product by proton NMR.

proton NMR proton (solvent: dimethyl sulfoxide)
1.05, 1.20; $CH_3$—
2.60; —OCO—$CH_2$—$CH_2$—COO—
3.20-3.80; —O—CH—$CH_2$—O—, —$CH_2$—, —CH—
3.86; —$CH_2$—
4.30-5.00; —O—CH—O—, —OH
7.16, 7.43; —$C_6H_4$—
8.65, 9.60; —NH—CO—

Example B2

Synthesis of MDI-PPG4-TRE (Molar Ratio 2/1/1)-3SUC-1ManA Polyurethane

Polyurethane (1.00 g) in Example B1 and dimethylformamide (30 ml) were added to a 4-mouth flask (purged with nitrogen gas) equipped with a mechanical stirrer. 1-Ethyl-3-(3-dimethylaminopropyl)carbodiimide hydrochloride (0.57 g), N-hydroxysuccinimide (0.34 g) and triethylamine (0.59 g) were added and dissolved by stirring at room temperature. Then, D-mannose amine hydrochloride (0.53 g) was added to the solution, and the mixture was reacted at said temperature for 24 hr. The reaction solution was concentrated and poured into water (75 ml) to allow precipitation of a product, which was collected by filtration, washed with water and vacuum dried to give a product (yield 96%).

The product was confirmed to be the object product by proton NMR.

proton NMR proton (solvent: dimethyl sulfoxide)
1.05, 1.20; $CH_3$—
2.50-2.60; —OCO—$CH_2$—$CH_2$—COO—
3.20-3.80; —O—CH—$CH_2$—O—, —$CH_2$—, —CH—
3.86; —$CH_2$—
4.30-5.00; —O—CH—O—, —OH
6.50; —NH—CO—
7.16, 7.43; —$C_6H_4$—
8.65, 9.60; —NH—CO—

Example B3

Synthesis of MDI-PPG4-TRE (Molar Ratio 2/1/1)-5SUC Polyurethane

Polyurethane (1.00 g) in Synthetic Example B1 was dissolved in dimethylformamide (25 ml) to a 4-mouth flask (purged with nitrogen gas) equipped with a mechanical stirrer at room temperature. Then, dimethylaminopyridine (0.025 g) was added to the reaction mixture, succinic anhydride (0.966 g) was added with stirring, and the mixture was reacted at 70° C. for 5 hr. The reaction solution was concentrated and poured into water (75 ml) to allow precipitation of a product, and 1M-hydrochloric acid (3 drops) was added. The precipitate was collected by filtration, washed with water and vacuum dried at 80° C. to give a product (yield 91%).

The product was confirmed to be the object product by proton NMR.

Example B4

Synthesis of MDI-PPG4-TRE (Molar Ratio 2/1/1)-5SUC-1ManA Polyurethane

Polyurethane (1.00 g) in Example B3 and dimethylformamide (35 ml) were added to a 4-mouth flask (purged with nitrogen gas) equipped with a mechanical stirrer. 1-Ethyl-3-(3-dimethylaminopropyl)carbodiimide hydrochloride (0.83 g), N-hydroxysuccinimide (0.49 g) and triethylamine (0.86 g) were added and dissolved by stirring at room temperature. Then, D-mannose amine hydrochloride (0.46 g) was added to the solution, and the mixture was reacted at said temperature for 24 hr. The reaction solution was concentrated and poured into acetone (100 ml) to allow precipitation of a product, which was collected by filtration, vacuum dried, washed with water and vacuum dried to give a product (yield 91%).

The product was confirmed to be the object product by proton NMR.

Example B5

Synthesis of MDI-PPG4-TRE (Molar Ratio 2/1/1)-5SUC-2ManA Polyurethane

Polyurethane (1.00 g) in Example B3 and dimethylformamide (35 ml) were added to a 4-mouth flask (purged with nitrogen gas) equipped with a mechanical stirrer. 1-Ethyl-3-(3-dimethylaminopropyl)carbodiimide hydrochloride (0.83 g), N-hydroxysuccinimide (0.49 g) and triethylamine (0.86 g) were added and dissolved by stirring at room temperature. Then, D-mannose amine hydrochloride (0.93 g) was added to the solution, and the mixture was reacted at said temperature for 24 hr. The reaction solution was concentrated and poured into acetone (100 ml) to allow precipitation of a product, which was collected by filtration, vacuum dried, washed with water and vacuum dried to give a product (yield 91%).

The product was confirmed to be the object product by proton NMR.

Example B6

Synthesis of MDI-PPG4-TRE (Molar Ratio 2/1/1)-5SUC-2GluA Polyurethane

Polyurethane (1.00 g) in Example B3 and dimethylformamide (35 ml) were added to a 4-mouth flask (purged with nitrogen gas) equipped with a mechanical stirrer. 1-Ethyl-3-(3-dimethylaminopropyl)carbodiimide hydrochloride (0.83 g), N-hydroxysuccinimide (0.49 g) and triethylamine (0.86 g) were added at room temperature with stirring, and the mixture was reacted for 1 hr. Then, D-glucose amine hydrochloride (1.24 g) was added to the solution, and the mixture was reacted at said temperature for 24 hr. The reaction solution was concentrated and poured into acetone (100 ml) to allow precipitation of a product, which was collected by filtration, vacuum dried, washed with water and vacuum dried to give a product (yield 96%).

The product was confirmed to be the object product by proton NMR.

proton NMR proton (solvent: dimethyl sulfoxide)
1.05, 1.20; $CH_3$—
2.50-2.60; —OCO—$CH_2$—$CH_2$—COO—
3.20-3.80; —O—CH—$CH_2$—O—, —$CH_2$—, —CH—
3.86; —$CH_2$—
4.30-5.00; —O—CH—O—, —OH
6.50; —NH—CO—
7.16, 7.43; —$C_6H_4$—
8.65, 9.60; —NH—CO—

Example B7

Synthesis of MDI-PPG7-TRE (Molar Ratio 2/1/1)-3SUC Polyurethane

Polyurethane (1.00 g) in Example B7 and dimethylacetamide (30 ml) were added to a 4-mouth flask (purged with nitrogen gas) equipped with a mechanical stirrer. 1-Ethyl-3-(3-dimethylaminopropyl)carbodiimide hydrochloride (0.47 g), N-hydroxysuccinimide (0.28 g) and triethylamine (0.82 g) were added at room temperature with stirring, and the mixture was reacted for 1 hr. Then, D-mannose amine hydrochloride (0.53 g) was added to the reaction mixture, and the mixture was reacted at said temperature for 24 hr. The reaction solution was concentrated and poured into acetone (100 ml) to allow precipitation of a product, which was collected by filtration, vacuum dried, washed with water and vacuum dried to give a product (yield 85%).

The product was confirmed to be the object product by proton NMR.

Example B8

Synthesis of MDI-PPG7-TRE (Molar Ratio 2/1/1)-3SUC-1ManA Polyurethane

Polyurethane (1.00 g) in Example B7 and dimethylacetamide (30 ml) were added to a 4-mouth flask (purged with nitrogen gas) equipped with a mechanical stirrer. 1-Ethyl-3-(3-dimethylaminopropyl)carbodiimide hydrochloride (0.47 g), N-hydroxysuccinimide (028 g) and triethylamine (0.82 g) were added at room temperature with stirring, and the mixture was reacted for 1 hr. Then, D-mannose amine hydrochloride (0.53 g) was added to the reaction mixture, and the mixture was reacted at said temperature for 24 hr. The reaction solution was concentrated and poured into acetone (100 ml) to allow precipitation of a product, which was collected by filtration, vacuum dried, washed with water and vacuum dried to give a product (yield 85%).

The product was confirmed to be the object product by proton NMR.

Example B9

Synthesis of MDI-PPG4-CTS (Molar Ratio 2/1/1)-2SUC Polyurethane

Polyurethane (0.80 g) in Synthetic Example B3 and dimethylformamide (25 ml) were added to a 4-mouth flask (purged with nitrogen gas) equipped with a mechanical stirrer. Succinic anhydride (0.90 g) and 4-dimethylaminopyridine (0.025 g) were added at room temperature with stirring, and the mixture was reacted at 70° C. for 5 hr. The reaction solution was concentrated, poured into water (75 ml) to allow precipitation of a product, and 1M hydrochloric acid (3 drops) was added. The precipitate was collected by filtration, washed with water and vacuum dried to give a product (yield 73%).

The product was confirmed to be the object product by proton NMR.

proton NMR proton (solvent: dimethyl sulfoxide)
1.05, 1.20; $CH_3$—
2.60; —OCO—$CH_2$—$CH_2$—COO—
3.20-3.80; —O—CH—$CH_2$—O—, —$CH_2$—, —CH—
3.86; —$CH_2$—
4.30-5.00; —O—CH—O—, —OH
7.16, 7.43; —$C_6H_4$—
8.65, 9.60; —NH—CO—

Example B10

Synthesis of MDI-PPG4-CTS (Molar Ratio 2/1/1)-2SUC-1.4GluA Polyurethane

Polyurethane (0.60 g) in Example B9 and dimethylformamide (30 ml) were added to a 4-mouth flask (purged with nitrogen gas) equipped with a mechanical stirrer. 1-Ethyl-3-(3-dimethylaminopropyl)carbodiimide hydrochloride (0.35 g), N-hydroxysuccinimide (0.21 g) and triethylamine (0.52 g) were added and dissolved by stirring at room temperature. Then, D-glucose amine hydrochloride (1.24 g) was added to the reaction mixture, and the mixture was reacted at said temperature for 24 hr. The reaction solution was filtered, concentrated and poured into acetone (100 ml) to allow precipitation of a product, which was filtered and vacuum dried to give a product (yield 67%).

The product was confirmed to be the object product by proton NMR.

proton NMR proton (solvent: dimethyl sulfoxide)
1.05, 1.20; $CH_3$—
2.50-2.60; —OCO—$CH_2$—$CH_2$—COO—
3.20-3.80; —O—CH—$CH_2$—O—, —$CH_2$—, —CH—
3.86; —$CH_2$—
4.30-5.00; —O—CH—O—, —OH
6.50; —NH—CO—
7.16, 7.43; —$C_6H_4$—
8.65, 9.60; —NH—CO—

Example B11

Synthesis of MDI-PPG4-CTS (Molar Ratio 2/1/1)-3SUC Polyurethane

Polyurethane (0.800 g) in Synthetic Example B3 and dimethylformamide (25 ml) were added to a 4-mouth flask (purged with nitrogen gas) equipped with a mechanical stirrer. Succinic anhydride (0.26 g) and 4-dimethylaminopyridine (0.25 g) were added at room temperature with stirring, and the mixture was reacted at 70° C. for 5 hr. The reaction solution was concentrated, poured into water (75 ml) to allow precipitation of a product, and 1M hydrochloric acid (3 drops) was added. The precipitate was collected by filtration, washed with water and vacuum dried to give a product (yield 70%).

The product was confirmed to be the object product by proton NMR.

proton NMR proton (solvent: dimethyl sulfoxide)
1.05, 1.20; $CH_3$—
2.60; —OCO—$CH_2$—$CH_2$—COO—
3.20-3.80; —O—CH—$CH_2$—O—, —$CH_2$—, —CH—
3.86; —$CH_2$—
4.30-5.00; —O—CH—O—, —OH
7.16, 7.43; —$C_6H_4$—
8.65, 9.60; —NH—CO—

Example B12

Synthesis of MDI-PPG4-CTS (Molar Ratio 2/1/1)-3SUC-2.4GluA Polyurethane

Polyurethane (0.35 g) in Example B11 and dimethylformamide (30 ml) were added to a 4-mouth flask (purged with nitrogen gas) equipped with a mechanical stirrer. 1-Ethyl-3-(3-dimethylaminopropyl)carbodiimide hydrochloride (0.29 g), N-hydroxysuccinimide (0.17 g) and triethylamine (0.30 g) were added at room temperature with stirring, and the mixture was reacted for 1 hr. Then, D-glucose amine hydrochloride (0.33 g) was added to the reaction mixture, and the mixture was reacted at said temperature for 24 hr. The reaction solution was filtered, concentrated and poured into acetone (100 ml) to allow precipitation of a product, which was collected by filtration, vacuum dried, washed with water and vacuum dried to give a product (yield 70%).

The product was confirmed to be the object product by proton NMR.

Example B13

Synthesis of MDI-PPG4-CTS (Molar Ratio 2/1/1)-5SUC Polyurethane

Polyurethane (0.80 g) in Synthetic Example B3 and dimethylformamide (25 ml) were added to a 4-mouth flask (purged with nitrogen gas) equipped with a mechanical stirrer. Succinic anhydride (0.23 g) and 4-dimethylaminopyridine (0.025 g) were added at room temperature with stirring, and the mixture was reacted at 70° C. for 5 hr. The reaction solution was concentrated, poured into water (75 ml) to allow precipitation of a product, and 1M hydrochloric acid (3 drops) was added. The precipitate was collected by filtration, washed with water and vacuum dried to give a product (yield 60%).

The product was confirmed to be the object product by proton NMR.

Example B14

Synthesis of MDI-PPG4-CTS (Molar Ratio 2/1/1)-5SUC-2GluA Polyurethane

Polyurethane (0.50 g) in Example B13 and dimethylacetamide (30 ml) were added to a 4-mouth flask (purged with nitrogen gas) equipped with a mechanical stirrer. 1-Ethyl-3-(3-dimethylaminopropyl)carbodiimide hydrochloride (0.38 g), N-hydroxysuccinimide (0.23 g) and triethylamine (0.53 g) were added at room temperature with stirring, and the mixture was reacted for 1 hr. Then, D-glucose amine hydrochloride (0.57 g) was added to the reaction mixture, and the mixture was reacted at said temperature for 24 hr. The reaction solution was filtered, concentrated and poured into acetone (100 ml) to allow precipitation of a product, which was collected by filtration, vacuum dried, washed with water and vacuum dried to give a product (yield 98%).

The product was confirmed to be the object product by proton NMR.

Example B15

Synthesis of MDI-PPG4-CTS (Molar Ratio 2/1/1)-5SUC-4GluA Polyurethane

Polyurethane (0.80 g) in Example B13 and dimethylformamide (30 ml) were added to a 4-mouth flask (purged with nitrogen gas) equipped with a mechanical stirrer. 1-Ethyl-3-(3-dimethylaminopropyl)carbodiimide hydrochloride (1.02 g), N-hydroxysuccinimide (0.60 g) and triethylamine (0.70 g) were added at room temperature with stirring, and the mixture was reacted for 1 hr. Then, D-glucose amine hydrochloride (1.15 g) was added to the reaction mixture, and the mixture was reacted at said temperature for 24 hr. The reaction solution was filtered, concentrated and poured into acetone (100 ml) to allow precipitation of a product, which was collected by filtration, vacuum dried, washed with water and vacuum dried to give a product (yield 71%).

The product was confirmed to be the object product by proton NMR.

Example B16

Synthesis of MDI-PPG4-CTS (Molar Ratio 2/1/1)-5SUC-3ManA Polyurethane

Polyurethane (1.00 g) in Example B13 and dimethylformamide (30 ml) were added to a 4-mouth flask (purged with nitrogen gas) equipped with a mechanical stirrer. 1-Ethyl-3-(3-dimethylaminopropyl)carbodiimide hydrochloride (0.64 g), N-hydroxysuccinimide (0.38 g) and triethylamine (0.66 g) were added and dissolved at room temperature by stirring. Then, D-mannose amine hydrochloride (0.72 g) was added to the solution, and the mixture was reacted at said temperature for 24 hr. The reaction solution was filtered, concentrated and poured into acetone (100 ml) to allow precipitation of a product, which was collected by filtration, vacuum dried, washed with water and vacuum dried to give a product (yield 99%).

The product was confirmed to be the object product by proton NMR.

proton NMR proton (solvent: dimethyl sulfoxide)
1.05, 1.20; $CH_3$—
2.50-2.60; —OCO—$CH_2$—$CH_2$—COO—
3.20-3.80; —O—CH—$CH_2$—O—, —$CH_2$—, —CH—
3.86; —$CH_2$—
4.30-5.00; —O—CH—O—, —OH
6.50; —NH—CO—
7.16, 7.43; —$C_6H_4$—
8.65, 9.60; —NH—CO—

Example B17

Synthesis of MDI-PPG7-CTS (Molar Ratio 2/1/1)-5SUC Polyurethane

Polyurethane (1.00 g) in Synthetic Example 4 and dimethylformamide (30 ml) were added to a 4-mouth flask (purged with nitrogen gas) equipped with a mechanical stirrer. Succinic anhydride (0.21 g) and 4-dimethylaminopyridine (0.025 g) were added at room temperature with stirring, and the mixture was reacted at 70° C. for 5 hr. The reaction solution was concentrated, poured into water (75 ml) to allow precipitation of a product, and 1M hydrochloric acid (3 drops) was added. The precipitate was collected by filtration, washed with water and vacuum dried to give a product (yield 87%).

Example B18

Synthesis of MDI-PPG7-CTS (Molar Ratio 2/1/1)-5SUC-2GluA Polyurethane

Polyurethane (5.00 g) in Example B17 and dimethylformamide (175 ml) were added to a 4-mouth flask (purged with nitrogen gas) equipped with a mechanical stirrer. 1-Ethyl-3-(3-dimethylaminopropyl)carbodiimide hydrochloride (5.62 g), N-hydroxysuccinimide (3.37 g) and triethylamine (5.86 g) were added at room temperature with stirring, and the mixture was reacted for 1 hr. Then, D-glucose amine hydrochloride (6.32 g) was added to the reaction mixture, and the mixture was reacted at said temperature for 24 hr. The reaction solution was filtered, concentrated and poured into acetone (300 ml) to allow precipitation of a product, which was collected by filtration, vacuum dried, washed with water and vacuum dried to give a product (yield 73%).

The product was confirmed to be the object product by proton NMR.
proton NMR proton (solvent: dimethyl sulfoxide)
1.05, 1.20; $CH_3$—
2.50-2.60; —OCO—$CH_2$—$CH_2$—COO—
3.20-3.80; —O—CH—$CH_2$—O—, —$CH_2$—, —CH—
3.86; —$CH_2$—
4.30-5.00; —O—CH—O—, —OH
6.50; —NH—CO—
7.16, 7.43; —$C_6H_4$—
8.65, 9.60; —NH—CO—

Example B18'

Synthesis of MDI-PPG7-CTS (Molar Ratio 2/1/1)-5SUC-2GluA Polyurethane (Another Method Using Condensation Agent DMT-MM Method)

Polyurethane (1.50 g) in Example B17, dimethylformamide (10 ml), and then methanol (30 ml) were added to a 4-mouth flask (purged with nitrogen gas) equipped with a mechanical stirrer. 4(4,6-dimethoxy-1,3,5-triazin-2-yl)-4-methylmorphorinium chloride (DMT-MM) (1.62 g)/methanol (5 ml) solution was added at room temperature with stirring. Then, D-glucose amine hydrochloride (1.26 g)/water (10 ml)) solution and then triethylamine (1.50 g) were added to the reaction mixture, and the mixture was reacted at room temperature for 9 hr. The reaction solution was filtered, concentrated and poured into methanol (300 ml) to allow precipitation of a product, which was collected by filtration, washed with methanol and vacuum dried to give a product (yield 50%).

The product was confirmed to be the object product by proton NMR.

Example B19

Synthesis of MDI-PPG7-CTS (Molar Ratio 2/1/1)-5SUC-3GluA Polyurethane

Polyurethane (10.00 g) in Example B17 and dimethylformamide (300 ml) were added to a 4-mouth flask (purged with nitrogen gas) equipped with a mechanical stirrer. 1-Ethyl-3-(3-dimethylaminopropyl)carbodiimide hydrochloride (10.83 g), N-hydroxysuccinimide (6.49 g) and triethylamine (11.28 g) were added at room temperature with stirring, and the mixture was reacted for 1 hr. Then, D-glucose amine hydrochloride (12.16 g) was added to the reaction mixture, and the mixture was reacted at said temperature for 24 hr. The reaction solution was filtered, concentrated and poured into acetone (900 ml) to allow precipitation of a product, which was collected by filtration, vacuum dried, washed with water and vacuum dried to give a product (yield 90%).

The product was confirmed to be the object product by proton NMR.

Example B20

Synthesis of MDI-PPG7-CTS (Molar Ratio 2/1/1)-5SUC-2ManA Polyurethane

Polyurethane (1.00 g) in Example B17 and dimethylformamide (40 ml) were added to a 4-mouth flask (purged with nitrogen gas) equipped with a mechanical stirrer. 1-Ethyl-3-(3-dimethylaminopropyl)carbodiimide hydrochloride (0.50 g), N-hydroxysuccinimide (0.30 g) and triethylamine (0.52 g) were added at room temperature with stirring, and the mixture was reacted for 1 hr. Then, D-mannose amine hydrochloride (0.56 g) was added to the reaction mixture, and the mixture was reacted at said temperature for 24 hr. The reaction solution was concentrated, filtered, concentrated and poured into acetone (200 ml) to allow precipitation of a product, which was collected by filtration, vacuum dried, washed with water and vacuum dried to give a product (yield 80%).

The product was confirmed to be the object product by proton NMR.
proton NMR proton (solvent: dimethyl sulfoxide)
1.05, 1.20; $CH_3$
2.50-2.60; —OCO—$CH_2$—$CH_2$—COO—
3.20-3.80; —O—CH—$CH_2$—O—, —$CH_2$—, —CH—
3.86; —$CH_2$—
4.30-5.00; —O—CH—O—, —OH
6.50; —NH—CO—
7.16, 7.43; —$C_6H_4$—
8.65, 9.60; —NH—CO—

<Evaluation of Each Sample>
1. The properties of the carboxyl group-modified oligosaccharide-containing polyurethane and the sugar residue-modified oligosaccharide-containing polyurethane of the present invention were evaluated by the following methods (1)-(3).
(1) molecular weight: The weight average molecular weight (Mw) of the polyurethane derivatives produced in the Examples was measured by GPC (gel permeation chromatography) method using DMF (dimethylformamide) as an eluent and RI detector (differential refractometer) with standard polyethylene glycol (PEG) as the standard.
(2) softening point: The softening point of polyurethane produced in the Examples was measured using a melting point measurement apparatus by starting heating from room temperature (5° C./min) and at the temperature at which the sample was dissolved.
(3) solvent solubility: Whether or not various polyurethanes (0.1 g) obtained in the Examples can be dissolved in dimethylacetamide (DMAC, 1 ml) was examined. The results of (1)-(3) are shown in Tables B1 and B2.

<Preparation of Polyurethane-Coated Petri Dish>
Various polyurethanes (30 mg) obtained in the Synthetic Examples were dissolved in dimethylacetamide (10 ml), filtered through a membrane filter to give polyurethane solutions. This solution (1 ml) was placed in a glass petri dish (diameter 35 mm) and dried under reduced pressure at 70° C. for 3 hr to give polyurethane-coated petri dishes.

<Evaluation of Monocyte Trapping by Polyurethane>

(1) Preparation of Mononuclear Cell

The above-mentioned adapter was connected to a winged intravenous injection needle, and a holder was connected to the other end of the adapter. The needle was punctured into an upper arm of a healthy subject, and the blood (about 7.5 ml) was drawn in a lymphocyte isolation tube (vacutainer tube, manufactured by Becton, Dickinson and Company). After blood sampling, 3.8% citric acid solution was added to the vacutainer tube such that blood:citric acid=10:1, and the vacutainer tube was immediately centrifuged at 3000 rpm for 20 min at room temperature. The plasma component was collected, and the mononuclear cell layer was separately collected in a container. Saline (40 ml) was added, and the mixture was centrifuged at 1500 rpm for 5 min at 4° C. This operation was repeated several times to wash the mononuclear cells. The washed mononuclear cells were re-suspended in the plasma collected above to give a lymphocyte suspension having a given concentration.

(2) Interaction with Polyurethane-Coated Petri Dish

Saline (1 ml) was added to various polyurethane-coated petri dishes and the supernatant was removed. This operation was repeated 3 times to wash the petri dishes. Then the mononuclear cell suspension (1 ml) prepared in (1) was added, and the mixture was left standing in an incubator at 37° C., 5% $CO_2$ for 30 min.

(3) Calculation of Monocyte Collection Rate and Purity

After a predetermined time, the supernatant was collected, and the petri dish was washed 3 times with saline (1 ml). Then, 10% mannose solution (1 ml) was added, and the mixture was left standing in an incubator at 37° C., 5% $CO_2$ for 15 min. Thereafter, the monocytes attached to the petri dish were collected by pipetting. The monocyte collection rate was determined by the following formula.

$$\text{monocyte collection rate}(\%) = \frac{\text{number of monocytes collected from petri dish}}{\text{number of monocytes on inoculation}} \times 100 \quad \text{formula (1)}$$

The number of monocytes was obtained by measuring the number of leukocytes in the cell suspension collected from the petri dish by a blood cell counter (KX-21NV, Sysmex Corporation), labeling the cell suspension with a CD14-PE fluorescence antibody (Japan Becton, Dickinson and Company), determining the monocyte ratio by a flow cytometer (BD FACS Canto, Japan Becton, Dickinson and Company), and multiplying the above-mentioned number of leukocytes by the monocyte ratio to be mentioned below. The number of monocytes on inoculation was also determined in the same manner using a cell suspension on inoculation as a target.

The purity of the monocyte was determined by labeling the cell-containing liquid collected from the petri dish with a CD14-PE fluorescence antibody (manufactured by Japan Becton, Dickinson and Company), and measuring the positive rate of monocyte by a flow cytometer (BD FACS Canto, Japan Becton, Dickinson and Company), which was taken as the purity.

The above results are shown in Tables B1-B5.

TABLE B1

| | | Ex. B1 | Ex. B2 | Ex. B3 | Ex. B4 |
|---|---|---|---|---|---|
| molar ratio | MDI | 2 | 2 | 2 | 2 |
| | PPG | PPG4 1 | PPG4 1 | PPG4 1 | PPG4 1 |
| | OLS | TRE 1 | TRE 1 | TRE 1 | TRE 1 |
| | SUC | 3 | 3 | 5 | 5 |
| | GluA | 0 | 0 | 0 | 0 |
| | 2-ManA | 0 | 1 | 0 | 1 |
| collection rate (%) | | 95 | 96 | 96 | 91 |
| Mw (RI) | | 45,600 | 82,000 | — | 40,000 |
| softening point (° C.) | | 105 | 100 | — | 75 |
| DMAc solubility | | dissolved | dissolved | dissolved | dissolved |
| monocyte collection rate (%) | | 51 | 88 | 50 | 86 |
| monocyte purity (%) | | 41 | 80 | 46 | 81 |

TABLE B2

| | | Ex. B5 | Ex. B6 | Ex. B7 | Ex. B8 |
|---|---|---|---|---|---|
| molar ratio | MDI | 2 | 2 | 2 | 2 |
| | PPG | PPG4 1 | PPG4 1 | PPG7 1 | PPG7 1 |
| | OLS | TRE 1 | TRE 1 | TRE 1 | TRE 1 |
| | SUC | 5 | 5 | 3 | 3 |
| | GluA | 0 | 2 | 0 | 0 |
| | 2-ManA | 2 | 0 | 0 | 1 |
| collection rate (%) | | 91 | 96 | 95 | 85 |
| Mw (RI) | | 100,000 | 38,500 | 37,000 | 150,000 |
| softening point (° C.) | | 60 | 60 | 100 | 100 |
| DMAc solubility | | dissolved | dissolved | dissolved | dissolved |
| monocyte collection rate (%) | | 96 | 89 | 46 | 73 |
| monocyte purity (%) | | 85 | 81 | 46 | 82 |

TABLE B3

| | | Ex. B9 | Ex. B10 | Ex. B11 | Ex. B12 |
|---|---|---|---|---|---|
| molar ratio | MDI | 2 | 2 | 2 | 2 |
| | PPG | PPG4 1 | PPG4 1 | PPG4 1 | PPG4 1 |
| | OLS | CTS 1 | CTS 1 | CTS 1 | CTS 1 |
| | SUC | 2 | 2 | 3 | 3 |
| | GluA | 0 | 1.4 | 0 | 2.4 |
| | 2-ManA | 0 | 0 | 0 | 2 |
| collection rate (%) | | 73 | 67 | 70 | 70 |
| Mw (RI) | | — | 17,000 | — | 20,000 |
| softening point (° C.) | | — | 120 | — | 90 |
| DMAc solubility | | dissolved | dissolved | dissolved | dissolved |
| monocyte collection rate (%) | | — | 89 | — | 77 |
| monocyte purity (%) | | — | 74 | — | 78 |

TABLE B4

| | | Ex. B13 | Ex. B14 | Ex. B15 | Ex. B16 |
|---|---|---|---|---|---|
| molar ratio | MDI | 2 | 2 | 2 | 2 |
| | PPG | PPG4 1 | PPG4 1 | PPG4 1 | PPG4 1 |
| | OLS | CTS 1 | CTS 1 | CTS 1 | CTS 1 |
| | SUC | 5 | 5 | 5 | 5 |
| | GluA | 0 | 2 | 4 | 0 |
| | 2-ManA | 0 | 0 | 0 | 3 |
| collection rate (%) | | 60 | 98 | 71 | 99 |
| Mw (RI) | | — | 32,000 | 38,500 | 87,000 |
| softening point (° C.) | | — | 85 | 80 | 95 |
| DMAc solubility | | dissolved | dissolved | dissolved | dissolved |
| monocyte collection rate (%) | | — | 94 | 98 | 90 |
| monocyte purity (%) | | — | 86 | 91 | 81 |

TABLE B5

| | | Ex. B17 | Ex. B18 | Ex. B19 | Ex. B20 |
|---|---|---|---|---|---|
| molar ratio | MDI | 2 | 2 | 2 | 2 |
| | PPG | PPG7 1 | PPG7 1 | PPG7 1 | PPG7 1 |
| | OLS | CTS 1 | CTS 1 | CTS 1 | CTS 1 |
| | SUC | 5 | 5 | 5 | 5 |
| | GluA | 0 | 2 | 3 | 0 |
| | 2-ManA | 0 | 0 | 0 | 2 |
| collection rate (%) | | 87 | 73 | 90 | 80 |
| Mw (RI) | | 39,000 | 47,000 | 190,000 | 56,000 |
| softening point (° C.) | | 120 | 100 | 80 | 95 |
| DMAc solubility | | dissolved | dissolved | dissolved | dissolved |
| monocyte collection rate (%) | | 23 | 90 | 81 | 83 |
| monocyte purity (%) | | 87 | 91 | 84 | 79 |

From the above results, it was found that the sugar residue-modified oligosaccharide-containing polyurethane has superior and selective monocyte trapping capability.

Example B21

Preparation of Dendritic Cell:

A mononuclear cell suspension (1 ml, the number of nuclear cells $2.0 \times 10^6$ cells) prepared according to the method of Example A1(1) was added to a mannose-bound polyurethane derivative (Example B20)-coated petri dish prepared according to the method of Example A1(1), and the mixture was left standing in an incubator at 37° C., 5% $CO_2$ for 30 min. After 30 min, the supernatant was removed, saline (1 ml) was added, the petri dish was stirred slowly, and the supernatant was removed. Untrapped cells were washed by repeating the washing operation 5 times. Then AIM-V (manufactured by GIBCO) medium (1.5 ml) prepared to IL-4: 500 IU/ml, GM-CSF: 500 IU/ml was added, and the cells were cultured for 6 days.

Collection of Dendritic Cell:

After culture for 6 days, the cells floating in the petri dish supernatant were collected, 10% mannose solution (1 ml) was further added to the petri dish, and the mixture was left standing in an incubator at 37° C., 5% $CO_2$ for 15 min. After 15 min, the cells trapped in the petri dish were collected by a pipetting operation, combined with the cells collected earlier, and the total number of the collected cells was determined by a blood cell counting chamber.

Identification of Dendritic Cell:

The cell suspension obtained by a dendritic cell collection operation were taken by 200 μl in a polypropylene test tube, 10 μl each of anti-CD14 antibody (PE-labeled), and anti-HLA-DR antibody (FITC-labeled, manufactured by Becton, Dickinson and Company) was added, and the mixture was left standing in a dark and cold place for 20 min. After a predetermined time, the mixture was centrifuged at 1500 rpm for 5 min, and the supernatant was removed. Then phosphate buffer (1 ml) was added, and the measurement was performed by a flow cytometer. As a result of the measurement, surface antigen CD14+ and HLA-DR+ was taken as monocyte, CD14− and HLA-DR+ was taken as dendritic cell, and the positive rate of each cell was determined.

The recovery rate of the dendritic cell was determined by the following formulas (A) and (B).

number of dendritic cells collected from the petri dish
=total number of cells collected from the petri
dish ×dendritic cell positive rate     formula (A)

dendritic cell recovery rate (%) =(number of dendritic
cells collected from the petri dish/number of
monocytes trapped in petri dish)×100     formula (B)

As a result, the dendritic cell recovery rate was 37.2%.

Since the recovery rate of the dendritic cell in a polystyrene petri dish free of coating with a mannose-bound polyurethane derivative polymer (Comparative Example A2) was 23.6%, the mannose-bound polyurethane derivative polymer was shown to have a high dendritic cell recovery rate.

Example C

Production of Acid-Modified Oligosaccharide-Containing Polyurethane

Now the acid-modified oligosaccharide-containing polyurethane of the present invention is explained in more detail based on the Examples, which are not to be construed as limitative.

The monomer compounds and the like to be used for polymerization are abbreviated as follows.
OLS=oligosaccharide skeleton.
TRE=trehalose
LAC=lactose
MAL=maltose
MDI=diphenylmethanediisocyanate
PPG4=polypropylene glycol (molecular weight 400)
PPG7=polypropylene glycol (molecular weight 700)
Py=pyridyl group Synthetic Example C1

Synthesis of MDI-PPG7-TRE (Molar Ratio 3/2.5/0.5) Polyurethane (Prepolymer Method 1)

Diphenylmethanediisocyanate (4.39 g) and dimethylacetamide (65 ml) were added to a 4-mouth flask (purged with nitrogen gas) equipped with a mechanical stirrer. Polypropylene glycol (average molecular weight 700, 10.23 g) was added at room temperature with stirring, and the mixture was reacted for 1 hr. Then, trehalose (1.00 g) was added to the reaction mixture, and the mixture was reacted at said temperature for 4 hr. The reaction solution was poured into a methanol/water (volume ratio 1/3) mixed solvent to allow precipitation of a product, which was collected by filtration, washed with a methanol/water solvent and vacuum dried to give a product (yield 86%).

The product was confirmed to be the object product by proton NMR.
proton NMR (solvent: dimethyl sulfoxide)
1.05, 1.20; $CH_3$—
3.20-3.80; —O—CH—$CH_2$—O—, —$CH_2$—, —CH—
3.86; —$CH_2$—
4.30-5.00; —O—CH—O—, —OH
7.16, 7.43; —$C_6H_4$—
8.65, 9.60; —NH—CO—

Synthetic Example C2

Synthesis of MDI-PPG7-LAC (Molar Ratio 3/2.5/0.5) Polyurethane (Prepolymer Method 1)

In the same manner as in Synthetic Example C1 and using diphenylmethanediisocyanate (4.39 g), dimethylacetamide (65 ml), polypropylene glycol (average molecular weight 700, 10.23 g) and lactose (1.00 g), a product was obtained (yield 90%).

The product was confirmed to be the object product by proton NMR.

proton NMR (solvent: dimethyl sulfoxide)
1.05, 1.20; $CH_3$—
3.20-3.80; —O—CH—$CH_2$—O—, —$CH_2$—, —CH—
3.86; —$CH_2$—
4.30-5.00; —O—CH—O—, —OH
7.16, 7.43; —$C_6H_4$—
8.65, 9.60; —NH—CO—

Synthetic Example C3

Synthesis of MDI-PPG7-MAL (Molar Ratio 3/2.5/0.5) Polyurethane (Prepolymer Method 1)

In the same manner as in Synthetic Example C1 and using diphenylmethanediisocyanate (4.39 g), dimethylacetamide (65 ml), polypropylene glycol (average molecular weight 700, 10.23 g) and maltose (1.00 g), a product was obtained (yield 93%).

The product was confirmed to be the object product by proton NMR.

proton NMR (solvent: dimethyl sulfoxide)
1.05, 1.20; $CH_3$—
3.20-3.80; —O—CH—$CH_2$—O—, —$CH_2$—, —CH—
3.86; —$CH_2$—
4.30-5.00; —O—CH—O—, —OH
7.16, 70.43; —$C_6H_4$—
8.65, 9.60; —NH—CO—

Synthetic Example C4

Synthesis of MDI-PPG4-TRE (Molar Ratio 2/1/1) Polyurethane (Prepolymer Method 1)

Diphenylmethanediisocyanate (5.85 g) and dimethylacetamide (65 ml) were added to a 4-mouth flask (purged with nitrogen gas) equipped with a mechanical stirrer. Polypropylene glycol (weight average molecular weight 400, 4.68 g) was added at room temperature with stirring, and the mixture was reacted for 1 hr. Then, trehalose (4.00 g) was added to the reaction mixture, and the mixture was reacted at said temperature for 4 hr. The reaction solution was poured into a methanol/water (volume ratio 1/3) mixed solvent to allow precipitation of a product, which was collected by filtration, washed with a methanol/water solvent and vacuum dried to give a product (yield 81%).

The product was confirmed to be the object product by proton NMR.

proton NMR (solvent: dimethyl sulfoxide)
1.05, 1.20; $CH_3$—
3.20-3.80; —O—CH—$CH_2$—O—, —$CH_2$—, —CH—
3.86; —$CH_2$—
4.30-5.00; —O—CH—O—, —OH
7.16, 7.43; —$C_6H_4$—
8.65, 9.60; —NH—CO—

Example C1

Synthesis of MDI-PPG7-TRE (Molar Ratio 3/2.5/0.5)—($SO_3Py$) Polyurethane

Polyurethane (1.00 g) in Synthetic Example C1 and dimethylformamide (50 ml) were added to and dissolved in a 4-mouth flask (purged with nitrogen gas) equipped with a mechanical stirrer. Pyridinesulfur trioxide complex (0.06 g) was added at room temperature with stirring, and the mixture was reacted at room temperature for 24 hr. The reaction solution was concentrated and water was added to allow precipitation of a product, which was collected by filtration, washed with water and vacuum dried to give a product (yield 94%).

The product was confirmed to be the object product by proton NMR and IR spectrum. In addition, from the integration value of pyridyl group in proton NMR, it was found that two sulfuric acid groups were introduced per one oligosaccharide.

proton NMR (solvent: dimethyl sulfoxide)
1.05, 1.20; $CH_3$—
2.50-2.60; —OCO—$CH_2$—$CH_2$—COO
3.20-3.80; —O—CH—$CH_2$—O—, —$CH_2$—, —CH—
3.86; —$CH_2$—
4.30-5.00; —O—CH—O—, —OH
6.50; —NH—CO—
7.16, 7.43; —$C_6H_4$—
8.10-9.00; —$C_5H_5NH$ (pyridyl group)
8.65, 9.60; —NH—CO—
IR (KBr):1040, 1120 $cm^{-1}$ ($SO_3$)

Example C2

Synthesis of MDI-PPG7-LAC (Molar Ratio 3/2.5/0.5)—($SO_3Py$) Polyurethane

Polyurethane (1.00 g) in Synthetic Example C2, dimethylformamide (50 ml) and dimethyl sulfoxide (5 ml) were added to and dissolved in a 4-mouth flask (purged with nitrogen gas) equipped with a mechanical stirrer. Pyridinesulfur trioxide complex (0.06 g) was added at room temperature with stirring, and the mixture was reacted at room temperature for 24 hr. The reaction solution was concentrated and water was added to allow precipitation of a product, which was collected by filtration, washed with water and vacuum dried to give a product (yield 98%).

The product was confirmed to be the object product by proton NMR and IR spectrum. In addition, from the integration value of pyridyl group in proton NMR, it was found that two sulfuric acid groups were introduced per one oligosaccharide.

Example C3

Synthesis of MDI-PPG7-MAL (Molar Ratio 3/2.5/0.5)—($SO_3Py$) Polyurethane

Polyurethane (1.00 g) in Synthetic Example C3, dimethylformamide (50 ml) and dimethyl sulfoxide (5 ml) were added to and dissolved in a 4-mouth flask (purged with nitrogen gas) equipped with a mechanical stirrer.

Pyridinesulfur trioxide complex (0.06 g) was added at room temperature with stirring, and the mixture was reacted at room temperature for 24 hr. The reaction solution was concentrated and water was added to allow precipitation of a product, which was collected by filtration, washed with water and vacuum dried to give a product (yield 98%).

The product was confirmed to be the object product by proton NMR and IR spectrum. In addition, from the integration value of pyridyl group in proton NMR, it was found that two sulfuric acid groups were introduced per one oligosaccharide.

Example C4

Synthesis of MDI-PPG4-TRE (Molar Ratio 2/1/1)-($SO_3Py$) Polyurethane

Polyurethane (1.00 g) in Synthetic Example C4 and dimethylformamide (15 ml) were added to and dissolved in a 4-mouth flask (purged with nitrogen gas) equipped with a mechanical stirrer. Pyridinesulfur trioxide complex (0.15 g) was added at room temperature with stirring, and the mixture was reacted at 40° C. for 6 hr. The reaction solution was concentrated and methanol was added to allow precipitation of a product, which was collected by filtration, washed with methanol and vacuum dried to give a product.

The product was confirmed to be the object product by proton NMR and IR spectrum. In addition, from the integration value of pyridyl group in proton NMR, it was found that two sulfuric acid groups were introduced per one oligosaccharide.

proton NMR (solvent: dimethyl sulfoxide)
1.05, 1.20; $CH_3$—
2.50-2.60; —OCO—$CH_2$—$CH_2$—COO—
3.20-3.80; —O—CH—$CH_2$—O—, —$CH_2$—, —CH—
3.86; —$CH_2$—
4.30-5.00; —O—CH—O—, —OH
6.50; —NH—CO—
7.16, 7.43; —$C_6H_4$—
8.10-9.00; —$C_5H_5$NH (pyridyl group)
8.65, 9.60; —NH—CO—
IR (KBr):1040, 1120 $cm^{-1}$ ($SO_3$)

<Evaluation of Each Sample>
Evaluation Method (2) softening point: The softening point of polyurethane produced in the Examples was measured using a melting point measurement apparatus by starting heating from room temperature (5° C./min) and at the temperature at which the sample was dissolved. (3) solvent solubility: Whether or not various polyurethanes (0.1 g) obtained in the Examples can be dissolved in dimethylacetamide (1 ml) was examined.

The results are shown in Table C1.

TABLE C1

|  |  | Ex. C1 | Ex. C2 | Ex. C3 | Ex. C4 |
|---|---|---|---|---|---|
| molar ratio | MDI | 3 | 3 | 3 | 2 |
|  | PPG | PPG7 2.5 | PPG7 2.5 | PPG7 2.5 | PPG4 1 |
|  | OLS | TRE 0.5 | LAC 0.5 | MAL 0.5 | TRE 1 |
|  | $SO_3$ | 2 | 2 | 2 | 2 |
| Mw (RI) |  | 27,000 | 57,000 | 53,000 | 32,000 |
| softening point (° C.) |  | 80 | 60 | 65 | 95 |
| DMAc solubility |  | dissolved | dissolved | dissolved | dissolved |

From the above results, the acid-modified oligosaccharide-containing polyurethane of the present invention was shown to have thermoplasticity and solvent solubility.

Example D

Acid-Modified Sugar Residue-Modified Oligosaccharide-Containing Polyurethane

Now the acid-modified sugar residue-modified oligosaccharide-containing polyurethane of the present invention is explained in more detail based on the Examples, which are not to be construed as limitative.

The monomer compounds to be used for polymerization are abbreviated as follows.
OLS=oligosaccharide skeleton
TRE=trehalose
MDI=diphenylmethanediisocyanate
PPG4=polypropylene glycol (molecular weight 400)
PPG7=polypropylene glycol (molecular weight 700)
SUC=succinic anhydride
GluA=glucose amine
ManA=mannose amine
Py=pyridyl group Synthetic Example D1

Synthesis of MDI-PPG4-TRE (Molar Ratio 2/1/1) Polyurethane (Prepolymer Method 1)

Diphenylmethanediisocyanate (5.85 g) and dimethylacetamide (65 ml) were added to a 4-mouth flask (purged with nitrogen gas) equipped with a mechanical stirrer. Polypropylene glycol (weight average molecular weight 400, 4.68 g) was added at room temperature with stirring, and the mixture was reacted for 1 hr. Then, trehalose (4.00 g) was added to the reaction mixture, and the mixture was reacted at said temperature for 4 hr. The reaction solution was poured into a methanol/water (volume ratio 1/3) mixed solvent to allow precipitation of a product, which was collected by filtration, washed with a methanol/water solvent and vacuum dried to give a product (yield 81%).

The product was confirmed to be the object product by proton NMR.

proton NMR (solvent: dimethyl sulfoxide)
1.05, 1.20; $CH_3$—
3.20-3.80; —O—CH—$CH_2$—O—, —$CH_2$—, —CH—
3.86; —$CH_2$—
4.30-5.00; —O—CH—O—, —OH
7.16, 7.43; —$C_6H_4$—
8.65, 9.60; —NH—CO—

Synthetic Example D2

Synthesis of MDI-PPG7-TRE (Molar Ratio 2/1/1) Polyurethane (Prepolymer Method 1)

Diphenylmethanediisocyanate (4.39 g) and dimethylacetamide (65 ml) were added to a 4-mouth flask (purged with nitrogen gas) equipped with a mechanical stirrer. Polypropylene glycol (weight average molecular weight 700, 6.14 g) was added at room temperature with stirring, and the mixture was reacted for 1 hr. Then, trehalose (3.00 g) was added to the reaction mixture, and the mixture was reacted at said temperature for 4 hr. The reaction solution was poured into a methanol/water (volume ratio 1/3) mixed solvent to allow precipitation of a product, which was collected by filtration, washed with a methanol/water solvent and vacuum dried to give a product (yield 87%).

The product was confirmed to be the object product by proton NMR.

proton NMR proton (solvent: dimethyl sulfoxide)
1.05, 1.20; $CH_3$—
3.20-3.80; —O—CH—$CH_2$—O—, —$CH_2$—, —CH—
3.86; —$CH_2$—
4.30-5.00; —O—CH—O—, —OH
7.16, 7.43; —$C_6H_4$—
8.65, 9.60; —NH—CO—

Synthetic Example D3

Synthesis of MDI-PPG7-TRE (Molar Ratio 3/2.5/0.5) Polyurethane (Prepolymer Method 1)

Methane diphenyl diisocyanate (4.39 g) and dimethylacetamide (65 ml) were added to a 4-mouth flask (purged with nitrogen gas) equipped with a mechanical stirrer. Polypropylene glycol (average molecular weight 700, 6.14 g) was added at room temperature with stirring, and the mixture was reacted for 1 hr. Then, trehalose (1.00 g) was added to the reaction mixture, and the mixture was reacted at said temperature for 4 hr. The reaction solution was poured into a methanol/water (volume ratio 1/3) mixed solvent to allow precipitation of a product, which was collected by filtration, washed with a methanol/water solvent and vacuum dried to give a product (yield 86%).

The product was confirmed to be the object product by proton NMR.

Synthetic Example D4

Synthesis of MDI-PPG4-TRE (Molar Ratio 2/1/1)-3SUC Polyurethane

Polyurethane (1.00 g) in Synthetic Example 1 and dimethylacetamide (25 ml) were added to a 4-mouth flask (purged with nitrogen gas) equipped with a mechanical stirrer. Succinic anhydride (0.24 g) and 4-dimethylaminopyridine (0.025 g) were added at room temperature with stirring, and the mixture was reacted at 70° C. for 5 hr. The reaction solution was concentrated, poured into water (75 ml) to allow precipitation of a product, and 1M hydrochloric acid (3 drops) was added. The precipitate was collected by filtration, washed with water and vacuum dried to give a product (yield 95%).

The product was confirmed to be the object product by proton NMR.
proton NMR (solvent: dimethyl sulfoxide)
1.05, 1.20; $CH_3$—
2.50-2.60; —OCO—$CH_2$—$CH_2$—COO—
3.20-3.80; —O—CH—$CH_2$—O—, —$CH_2$—, —CH—
3.86; —$CH_2$—
4.30-5.00; —O—CH—O—, —OH
7.16, 7.43; —$C_6H_4$—
8.65, 9.60; —NH—CO—

Synthetic Example D5

Synthesis of MDI-PPG4-TRE (Molar Ratio 2/1/1)-3SUC-1ManA Polyurethane

Polyurethane (1.00 g) in Synthetic Example 4 and dimethylformamide (30 ml) were added to a 4-mouth flask (purged with nitrogen gas) equipped with a mechanical stirrer. 1-Ethyl-3-(3-dimethylaminopropyl)carbodiimide hydrochloride (EDC, 0.57 g), N-hydroxysuccinimide (0.34 g) and triethylamine (0.59 g) were added and dissolved at room temperature by stirring. Then, D-mannose amine hydrochloride (0.53 g) was added to the solution, and the mixture was reacted at said temperature for 24 hr. The reaction solution was concentrated and poured into water to allow precipitation of a product, which was collected by filtration, washed with water and vacuum dried to give a product (yield 96%).

The product was confirmed to be the object product by proton NMR.
proton NMR (solvent: dimethyl sulfoxide)
1.05, 1.20; $CH_3$—
2.50-2.60; —OCO—$CH_2$—$CH_2$—COO—
3.20-3.80; —O—CH—$CH_2$—O—, —$CH_2$—, —CH—
3.86; —$CH_2$—
4.30-5.00; —O—CH—O—, —OH
6.50; —NH—CO—
7.16, 7.43; —$C_6H_4$—
8.65, 9.60; —NH—CO—

Synthetic Example D6

Synthesis of MDI-PPG4-TRE (Molar Ratio 2/1/1)-5SUC Polyurethane

Polyurethane (1.00 g) in Synthetic Example D1 was dissolved at room temperature in dimethylacetamide (25 ml) in a 4-mouth flask (purged with nitrogen gas) equipped with a mechanical stirrer. Dimethylaminopyridine (0.025 g) was added and then succinic anhydride (0.966 g) was added with stirring, and the mixture was reacted at 70° C. for 5 hr. The reaction solution was concentrated, poured into water (75 ml) to allow precipitation of a product, and 1M hydrochloric acid (0.25 ml) was added. The precipitate was collected by filtration, washed with water and vacuum dried at 80° C. to give a product (yield 91%).

The product was confirmed to be the object product by proton NMR.

Synthetic Example D7

Synthesis of MDI-PPG4-TRE (Molar Ratio 2/1/1)-5SUC-2GluA Polyurethane

Polyurethane (1.00 g) in Synthetic Example 5 and dimethylacetamide (35 ml) were added to a 4-mouth flask (purged with nitrogen gas) equipped with a mechanical stirrer. 1-Ethyl-3-(3-dimethylaminopropyl)carbodiimide hydrochloride (0.83 g) and N-hydroxysuccinimide (0.49 g) were added at room temperature with stirring, and the mixture was reacted for 1 hr. Then, D-glucose amine hydrochloride (1.24 g) and triethylamine (1.45 g) were added to the reaction mixture, and the mixture was reacted at said temperature for 24 hr. The reaction solution was concentrated and poured into water to allow precipitation of a product, which was collected by filtration, washed with water and vacuum dried to give a product (yield 96%).

The product was confirmed to be the object product by proton NMR.
proton NMR proton (solvent: dimethyl sulfoxide)
1.05, 1.20; $CH_3$—
2.50-2.60; —OCO—$CH_2$—$CH_2$—COO—
3.20-3.80; —O—CH—$CH_2$—O—, —$CH_2$—, —CH—
3.86; —$CH_2$—
4.30-5.00; —O—CH—O—, —OH
6.50; —NH—CO—
7.16, 7.43; —$C_6H_4$—
8.65, 9.60; —NH—CO—

Synthetic Example D8

Synthesis of MDI-PPG7-TRE (Molar Ratio 2/1/1)-3SUC Polyurethane

Polyurethane (2.00 g) in Synthetic Example D2 and dimethylacetamide (50 ml) were added to a 4-mouth flask (purged with nitrogen gas) equipped with a mechanical stirrer. Succinic anhydride (0.79 g) and 4-dimethylaminopyridine (0.025 g) were added at room temperature with stirring, and the mixture was reacted at 70° C. for 5 hr. The reaction solution was concentrated, poured into water (75 ml) to allow precipitation of a product, and 1M hydrochloric acid (3 drops) was added. The precipitate was collected by filtration, washed with water and vacuum dried to give a product (yield 84%).

The product was confirmed to be the object product by proton NMR.

Synthetic Example D9

Synthesis of MDI-PPG7-TRE (Molar Ratio 2/1/1)-3SUC-1ManA Polyurethane

Polyurethane (1.50 g) in Synthetic Example D8 and dimethylacetamide (50 ml) were added to a 4-mouth flask (purged with nitrogen gas) equipped with a mechanical stirrer. 1-Ethyl-3-(3-dimethylaminopropyl)carbodiimide hydrochloride (0.47 g), N-hydroxysuccinimide (0.28 g) and triethylamine (0.62 g) were added at room temperature with stirring, and the mixture was reacted for 1 hr. Then, D-mannose amine hydrochloride (0.53 g) was added to the reaction mixture, and the mixture was reacted at said temperature for 24 hr. The reaction solution was concentrated and poured into water to allow precipitation of a product, which was collected by filtration, washed with water and vacuum dried to give a product (yield 78%).

The product was confirmed to be the object product by proton NMR.

Synthetic Example D10

Synthesis of MDI-PPG7-TRE (Molar Ratio 3/2.5/0.5)-5SUC Polyurethane

Polyurethane (5.00 g) in Synthetic Example D3 and dimethylacetamide (100 ml) were added to a 4-mouth flask (purged with nitrogen gas) equipped with a mechanical stirrer. Succinic anhydride (1.15 g) and 4-dimethylaminopyridine (0.035 g) were added at room temperature with stirring, and the mixture was reacted at 70° C. for 5 hr. The reaction solution was concentrated, poured into water (75 ml) to allow precipitation of a product, and 1M hydrochloric acid (3 drops) was added. The precipitate was collected by filtration, washed with water and vacuum dried to give a product (yield 98%).

The product was confirmed to be the object product by proton NMR.

Synthetic Example D11

Synthesis of MDI-PPG7-TRE (Molar Ratio 3/2.5/0.5)-5SUC-1ManA Polyurethane

Polyurethane (3.00 g) in Synthetic Example D10 and dimethylacetamide (100 ml) were added to a 4-mouth flask (purged with nitrogen gas) equipped with a mechanical stirrer. 1-Ethyl-3-(3-dimethylaminopropyl)carbodiimide hydrochloride (0.50 g), N-hydroxysuccinimide (0.30 g) and triethylamine (0.66 g) were added at room temperature with stirring, and the mixture was reacted for 1 hr. Then, D-mannose amine hydrochloride (0.28 g) was added to the reaction mixture, and the mixture was reacted at said temperature for 24 hr. The reaction solution was concentrated and poured into water to allow precipitation of a product, which was collected by filtration, washed with water and vacuum dried to give a product (yield 85%).

The product was confirmed to be the object product by proton NMR.

Example D1

Synthesis of MDI-PPG4-TRE (Molar Ratio 2/1/1)-3SUC-1ManA-(SO$_3$Py) Polyurethane Polyurethane (0.100 g) in Synthetic Example D5 and dimethylformamide (15 ml) were added to and dissolved in a 4-mouth flask (purged with nitrogen gas) equipped with a mechanical stirrer. Pyridinesulfur trioxide complex (0.15 g) was added at room temperature with stirring, and the mixture was reacted for 8 hr. The reaction solution was concentrated and water was added to allow precipitation of a product, which was collected by filtration, washed with water and vacuum dried to give a product.

The product was confirmed to be the object product by proton NMR and IR spectrum.

proton NMR (solvent: dimethyl sulfoxide)
1.05, 1.20; $CH_3$—
2.50-2.60; —OCO—$CH_2$—$CH_2$—COO—
3.20-3.80; —O—CH—$CH_2$—O—, —$CH_2$—, —CH—
3.86; —$CH_2$—
4.30-5.00; —O—CH—O—, —OH
6.50; —NH—CO—
7.16, 7.43; —$C_6H_4$—
8.10-9.00; —$C_5H_5$N.H$^+$
8.65, 9.60; —NH—CO—
IR (KBr):1040, 1120 cm$^{-1}$ (SO$_3$)

Example D2

Synthesis of MDI-PPG4-TRE (Molar Ratio 2/1/1)-5SUC-2GluA-2 (SO$_3$Py) Polyurethane Polyurethane (1.00 g) in Synthetic Example D7 and dimethylformamide (15 ml) were added to and dissolved in a 4-mouth flask (purged with nitrogen gas) equipped with a mechanical stirrer. Pyridinesulfur trioxide complex (0.30 g) was added at room temperature with stirring, and the mixture was reacted for 8 hr. The reaction solution was concentrated and water was added to allow precipitation of a product, which was collected by filtration, washed with water and vacuum dried to give a product.

The product was confirmed to be the object product by proton NMR and IR spectrum.

Example D3

Synthesis of MDI-PPG7-TRE (Molar Ratio 3/2.5/0.5)-5SUC-1ManA (SO$_3$Py) Polyurethane Polyurethane (1.00 g) in Synthetic Example D11 and dimethylformamide (50 ml) were added to and dissolved in a 4-mouth flask (purged with nitrogen gas) equipped with a mechanical stirrer. Pyridinesulfur trioxide complex (0.027 g) was added at room temperature with stirring, and the mixture was reacted for 8 hr. The reaction solution was concentrated and water was added to allow precipitation of a product, which was collected by filtration, washed with water and vacuum dried to give a product.

The product was confirmed to be the object product by proton NMR and IR spectrum.

Example D4

Synthesis of MDI-PPG7-TRE (Molar Ratio 3/2.5/0.5)-5SUC-1ManA-2 (SO$_3$Py) Polyurethane Polyurethane (1.00 g) in Synthetic Example 11 and dimethylformamide (50 ml) were added to and dissolved in a 4-mouth flask (purged with nitrogen gas) equipped with a mechanical stirrer. Pyridinesulfur trioxide complex (0.054 g) was added at room temperature with stirring, and the mixture was reacted for 8 hr. The reaction solution was concentrated and water was added to allow precipitation of a product, which was collected by filtration, washed with water and vacuum dried to give a product.

The product was confirmed to be the object product by proton NMR and IR spectrum.

Example D5

Synthesis of MDI-PPG7-TRE (Molar Ratio 2/1/1)-3SUC-1ManA-($SO_3Py$) Polyurethane Polyurethane (1.00 g) in Synthetic Example 8 and dimethylformamide (70 ml) were added to and dissolved in a 4-mouth flask (purged with nitrogen gas) equipped with a mechanical stirrer. Pyridinesulfur trioxide complex (0.078 g) was added at room temperature with stirring, and the mixture was reacted for 8 hr. The reaction solution was concentrated and water was added to allow precipitation of a product, which was collected by filtration, washed with water and vacuum dried to give a product.

The product was confirmed to be the object product by proton NMR and IR spectrum.

<Evaluation of Each Sample>
Evaluation Method
(1) molecular weight: The weight average molecular weight (Mw) of the polyurethane derivatives produced in the Examples was measured using DMF (dimethylformamide) as an eluent and standard polyethylene glycol (PEG) as the standard.
(2) softening point: The softening point of polyurethane produced in the Examples was measured using a melting point measurement apparatus by starting heating from room temperature (5° C./min) and at the temperature at which the sample was dissolved.
(3) solvent solubility: Whether or not various polyurethanes (0.1 g) obtained in the Examples can be dissolved in dimethylacetamide (1 ml) was examined.

The results are shown in Table D1.

TABLE D1

|  |  | Ex. D1 | Ex. D2 | Ex. D3 | Ex. D4 | Ex. D5 |
|---|---|---|---|---|---|---|
| molar ratio | MDI | 2 | 2 | 3 | 3 | 2 |
|  | PPG | PPG4 1 | PPG4 1 | PPG7 2.5 | PPG7 2.5 | PPG7 1 |
|  | OLS | TRE 1 | TRE 1 | TRE 0.5 | TRE 0.5 | TRE 1 |
|  | SUC | 3 | 5 | 5 | 5 | 3 |
|  | GluA | 0 | 2 | 0 | 0 | 0 |
|  | ManA | 1 | 0 | 1 | 1 | 1 |
|  | $SO_3$ | 1 | 2 | 1 | 2 | 1 |
| Mw (RI) |  | 27,000 | 51,000 | 39,000 | 35,000 | 34,000 |
| softening point (° C.) |  | 60 | 50 | 75 | 70 | 70 |
| DMAc solubility |  | dissolved | dissolved | dissolved | dissolved | dissolved |

From the above results, the sugar residue-modified oligosaccharide-containing polyurethane was shown to have thermoplasticity and solvent solubility.

Example E

Evaluation of Lectin Trapping and Isolation by Polyurethane (1) Preparation of Lectin Solution 0.0125, 0.0250, 0.050 mg/ml phosphate buffers (pH 7.2) of FITC-labeled two kinds of lectin ConA-FITC (manufactured by SEIKAGAKU CORPORATION) and WGA-FITC (manufactured by SEIKAGAKU CORPORATION) were prepared.

(2) Preparation of analytical curve: the above-mentioned two kinds of lectin solution were taken in quartz cell, and the fluorescence intensity (apparatus: fluorescence spectrophotometer FP-6500 manufactured by JASCO Corporation, wavelength 519 nm) was plotted against the concentration. It was confirmed that a linear line was obtained.

(3) Preparation of Polyurethane-Coated Petri Dish

Phosphate buffer (pH 7.2, 1 ml) was added to a petri dish coated with the polyurethane obtained in Example B18, and the supernatant was removed. This operation was repeated 3 times to wash the petri dish.

(4) The fluorescence intensity ($I_0$) of 0.050 mg/ml phosphate buffer (pH 7.2) was measured. 3 ml thereof was placed in a glass petri dish coated with the polyurethane obtained in Example B18. After leaving at 20° C. for 30 min, the supernatant was taken in a quartz glass cell, and the fluorescence intensity ($I_1$) was measured.

The lectin trap rate was determined by the following formula.

$$\text{trap rate }(\%)=(I_1-I_0)/(I_0)\times 100$$

The results are respectively shown in the following Table E as Examples E1 and E2. For comparison, petri dishes free of polyurethane coating were subjected to a similar experiment (Comparative Examples E1 and E2).

TABLE E

|  | Ex. E1 | Ex. E2 | Com. Ex. E1 | Com. Ex. E2 |
|---|---|---|---|---|
| polymer | Example B18 |  | none |  |
| lectin type | ConA | WGA | ConA | WGA |
| lectin trap rate (%) | 72 | 8 | 0 | 0 |

Example B18

MDI-PPG7-CTS (Molar Ratio 2/1/1)-5SUC-2GluA Polyurethane

From the above, the sugar residue-modified oligosaccharide-containing polyurethane of the present invention was found to have a superior lectin trapping capability.

The lectin harvested in the present invention can be used as a cell fractionation reagent, a clinical diagnostic reagent, a clinical therapeutic drug and the like, based on its sugar chain binding specificity, blood type specificity, anticancer effect and the like. For such uses, lectin may be directly used as a lectin-isolation device composition.

Industrial Applicability

According to the method of the present invention, a cell such as monocyte and the like or a protein such as lectin and the like can be collected conveniently at high purity and in a high collection rate. Moreover., by inducing monocytes to further differentiate into dendritic cells according to the method of the present invention, dendritic cells can be prepared conveniently and highly efficiently.

In addition, the sugar residue-modified oligosaccharide-containing polyurethane, carboxyl group-modified oligosaccharide-containing polyurethane, acid-modified oligosaccharide-containing polyurethane and acid-modified sugar residue-modified oligosaccharide-containing polyurethane of the present invention are solvent soluble and thermoplastic, and superior in film forming capability. Furthermore, since these polyurethanes are particularly superior in trapping capability of cell (e.g., monocyte and the like), protein, virus and the like, they are useful as highly functional materials used in the fields of isolation, analysis and the like of cells, proteins and viruses, particularly, for use involving contact with blood (e.g., various isolation devices, isolation filters and the like for harvesting blood, cell, monocyte, protein and the like) and the like.

Of these, the acid-modified oligosaccharide-containing polyurethane and acid-modified sugar residue-modified oligosaccharide-containing polyurethane of the present invention are expected to have affinity for particular cells, proteins and viruses, since oligosaccharide or sugar residue is further modified with an acid. Therefore, these polyurethanes are useful as highly functional materials for use in the fields of medicine and livingwares.

This application is based on application Nos 2006-148620, 2006-149031, 2006-163955 and 2006-179690 filed in Japan, the contents of which are incorporated hereinto by reference. In addition, the patent documents and non-patent documents cited in the present specification are hereby incorporated by reference, to the extent that the entire contents have been disclosed herein.

The invention claimed is:

1. An oligosaccharide-containing polyurethane represented by the following formula [1-1]:

$$\text{---}\{[CO\text{---}NH\text{---}R^1\text{---}NH\text{---}CO]\text{---}[O\text{---}R^2\text{---}O]\}_m\text{---}\#$$
$$(O_2C\text{---}R^3\text{---}CO\text{---}NH\text{---}R^4)_p$$
$$\#\text{---}\{[CO\text{---}NH\text{---}R^1\text{---}NH\text{---}CO]\text{---}[O\text{---}OLS\text{---}O]\}_n\text{---}$$
$$(HO_2C\text{---}R^3\text{---}CO_2)_q (OH)_{r-p-q}$$
[1-1]

wherein
$R^1$ is a divalent $C_{1-16}$ hydrocarbon group optionally having substituent(s),
$R^2$ is a divalent group containing the same or different 1 to 100 units in total selected from a $C_{2-12}$ oxyalkylene unit and a divalent $C_{2-12}$ hydrocarbon unit optionally having substituent(s),
$R^3$ is a $C_{2-4}$ alkylene group,
$R^4$ is a monosaccharide- or disaccharide-derived sugar residue,
OLS is an oligosaccharide skeleton having two primary hydroxyl groups,
r shows the total number of secondary hydroxyl groups of oligosaccharide,
p and q are each an integer within the range of $1 \leq p \leq r$, $0 \leq q \leq r-1$, and
m and n are each a repeat unit number, m is an integer of 0-1000 and n is an integer of 1-1000, and n/(m+n) is a number within the range of 0.01-1.00,
the following formula [1-2]:

$$\text{---}\{[CO\text{---}NH\text{---}R^1\text{---}NH\text{---}CO]\text{---}[O\text{---}R^2\text{---}O]\}_m\text{---}\#$$
$$\#\text{---}\{[CO\text{---}NH\text{---}R^1\text{---}NH\text{---}CO]\text{---}[O\text{---}OLS\text{---}O]\}_n\text{---}$$
$$(HO_2C\text{---}R^3\text{---}CO_2)_{p+q} (OH)_{r-p-q}$$
[1-2]

wherein
$R^1$ is a divalent $C_{1-16}$ hydrocarbon group optionally having substituent(s),
$R^2$ is a divalent group containing the same or different 1 to 100 units in total selected from a $C_{2-12}$ oxyalkylene unit and a divalent $C_{2-12}$ hydrocarbon unit optionally having substituent(s),
$R^3$ is a $C_{2-4}$ alkylene group,
OLS is an oligosaccharide skeleton having two primary hydroxyl groups,
r shows the total number of secondary hydroxyl groups of oligosaccharide,
p and q are each an integer within the range of $1 \leq p \leq r$, $0 \leq q \leq r-1$, and
m and n are each a repeat unit number, m is an integer of 0-1000 and n is an integer of 1-1000, and n/(m+n) is a number within the range of 0.01-1.00,
the following formula [2-1]:

$$\text{---}\{[CO\text{---}NH\text{---}R^1\text{---}NH\text{---}CO]\text{---}[O\text{---}R^2\text{---}O]\}_m\text{---}\#$$
$$(OXM)_s$$
$$\#\text{---}\{[CO\text{---}NH\text{---}R^1\text{---}NH\text{---}CO]\text{---}[O\text{---}OLS\text{---}O]\}_n\text{---}$$
$$(OH)_{r-s}$$
[2-1]

wherein
$R^1$ is a divalent $C_{1-16}$ hydrocarbon group optionally having substituent(s),
$R^2$ is a divalent group containing the same or different 1 to 100 units in total selected from a $C_{2-12}$ oxyalkylene unit and a divalent $C_{2-12}$ hydrocarbon unit optionally having substituent(s),
OLS is an oligosaccharide skeleton having two primary hydroxyl groups,
r shows the total number of secondary hydroxyl groups of oligosaccharide,
XM is an acid-containing group wherein M is a hydrogen atom, an alkali metal atom, an ammonium group or an organic amino group, and X is an acid-derived moiety,
s shows the number of the secondary hydroxyl groups of an oligosaccharide modified with an acid-containing group, which is an integer within the range of $1 \leq s \leq r$, and
m and n are each a repeat unit number, m is an integer of 0-1000 and n is an integer of 1-1000, and n/(m+n) is a number within the range of 0.01-1.00, or the following formula [3-1]:

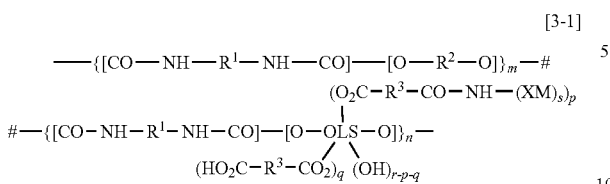

wherein
$R^1$ is a divalent $C_{1-16}$ hydrocarbon optionally having substituent(s),
$R^2$ is a divalent group containing the same or different 1 to 100 units in total selected from a $C_{2-12}$ oxyalkylene unit and a divalent $C_{2-12}$ hydrocarbon unit optionally having substituent(s),
$R^3$ is a $C_{2-4}$ alkylene group,
$R^4$ is a monosaccharide- or disaccharide-derived sugar residue,
XM is an acid-containing group wherein M is a hydrogen atom, an alkali metal atom, an ammonium group or an organic amino group, and X is an acid-derived moiety, s shows the number of hydroxyl groups of a sugar residue $R^4$ modified with an acid-containing group, which is an integer within the range of $1 \leq s \leq 4$,
OLS is an oligosaccharide skeleton having two primary hydroxyl groups,
r shows the total number of secondary hydroxyl groups of oligosaccharide,
p and q are each an integer within the range of $1 \leq p \leq r$, $0 \leq q \leq r-1$, and
m and n are each a repeat unit number, m is an integer of 0-1000 and n is an integer of 1-1000, and n/(m+n) is a number within the range of 0.01-1.00.

2. A physiological material comprising the polyurethane of claim 1.

3. An isolation material comprising the polyurethane of claim 1 at least on a part of a surface thereof.

4. The isolation material of claim 3, which is a cell isolation material, a protein isolation material or a blood isolation material.

5. The isolation material of claim 3, having the form of a filter.

6. An isolation device comprising a container provided with a liquid inlet and/or a liquid outlet, wherein the container comprises the isolation material of claim 3 in at least one part thereof.

7. The isolation device of claim 6, which is a cell isolation device or a protein isolation device.

8. A method of harvesting a cell comprising performing
1) a step for trapping a cell on an isolation material by contacting a body fluid with the isolation material comprising, on at least a part of a surface thereof, a substance having a sugar structure,
2) a step for removing untrapped cells by washing the isolation material with a washing liquid, and
3) a step for collecting a trapped cell from the isolation material, in this order, wherein the substance having a sugar structure is the polyurethane of claim 1.

* * * * *